US006331664B1

(12) United States Patent
Rubin-Wilson et al.

(10) Patent No.: US 6,331,664 B1
(45) Date of Patent: Dec. 18, 2001

(54) ACYL-ACP THIOESTERASE NUCLEIC ACIDS FROM MAIZE AND METHODS OF ALTERING PALMITIC ACID LEVELS IN TRANSGENIC PLANTS THEREWITH

(75) Inventors: Beth Rubin-Wilson, Indianapolis; Lining Guo, Brownsburg; Tom Skokut, Carmel; Scott Young, Indianapolis, all of IN (US); Otto Folkerts, Guilford, CT (US); Katherine Armstrong; Neil M. Cowen, both of Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/064,411

(22) Filed: Apr. 22, 1998

Related U.S. Application Data

(60) Provisional application No. 60/045,827, filed on May 5, 1997.

(51) Int. Cl.[7] .............................. A01H 5/00; C12N 5/14; C12N 9/16; C12N 15/29; C12N 15/82
(52) U.S. Cl. ................... 800/298; 435/196; 435/320.1; 435/419; 435/468; 536/23.2; 536/23.6; 800/281
(58) Field of Search ..................... 536/23.2, 23.6, 536/24.1; 435/320.1, 419, 468, 196; 800/281, 298, 306, 312, 314, 320.1, 322, 323

(56) References Cited

U.S. PATENT DOCUMENTS

| 5,147,792 | 9/1992 | Perchorowicz et al. ............. 435/134 |
| 5,298,421 | 3/1994 | Davies et al. ......................... 435/320 |
| 5,304,481 | 4/1994 | Davies et al. ......................... 435/196 |
| 5,344,771 | 9/1994 | Davies et al. ........................ 435/172.3 |
| 5,455,167 | 10/1995 | Voelker et al. ..................... 435/172.3 |
| 5,498,830 | 3/1996 | Barry et al. ........................... 800/205 |
| 5,500,361 | 3/1996 | Kinney ............................... 435/172.3 |
| 5,512,482 | 4/1996 | Voelker et al. ..................... 435/320.1 |
| 5,639,790 | 6/1997 | Voelker et al. ........................ 514/552 |
| 5,654,495 | 8/1997 | Voelker et al. ........................ 800/250 |
| 5,667,997 | 9/1997 | Voelker et al. ..................... 435/172.3 |
| 5,723,761 | 3/1998 | Voelker et al. ........................ 800/205 |

FOREIGN PATENT DOCUMENTS

| 0 561 569 | 9/1993 | (EP) .............................. C12N/15/82 |
| 91/16421 | 10/1991 | (WO) . |
| 91/18985 | 12/1991 | (WO) . |
| 92/11373 | 7/1992 | (WO) . |
| 92/20236 | 11/1992 | (WO) . |
| 93/18158 | 9/1993 | (WO) . |
| 94/10189 | 5/1994 | (WO) . |
| 94/10288 | 5/1994 | (WO) . |
| 94/29467 | 12/1994 | (WO) . |
| 95/06740 | 3/1995 | (WO) . |
| 95/13390 | 5/1995 | (WO) . |
| WO 96/01905 | 1/1996 | (WO) . |
| 96/06936 | 3/1996 | (WO) . |
| 96/23892 | 8/1996 | (WO) . |
| WO 96/31609 | 10/1996 | (WO) . |
| 96/36719 | 11/1996 | (WO) . |
| 97/12047 | 4/1997 | (WO) . |

OTHER PUBLICATIONS

Davies, et al., "Developmental Induction, Purification, and Further Characterization of 12:0–ACP Thioesterase from Immature Cotyledons of *Umbellularia californica*", Archives of Biochemistry and Biophysics, vol. 290, No. 1, pp. 37–45 (1991).

Dehesh et al., "Production of high levels of 8:0 and 10:0 fatty acids in transgenic canola by overexpression of CH FatB2, a thioesterase cDNA from *Cuphea hookeriana*", The Plant Journal, vol. 9, No. 2, pp. 167–172, (1996).

Dehesh et al., "Two Novel Thioesterases Are Key Determinants of the Bimodal Distribution of Acyl Chain Length of *Cuphe palustris* Seed oil". Plant Physiol, vol. 110, pp. 203–210, (1996).

Dörmann, et al., "Characterization of two acyl–acyl carrier protein thioesterases from developing Cuphea seeds specific for medium–chain–and oleoyl–acyl carrier protein", Planta, vol. 189, pp. 425–432, (1993).

Dörmann, et al., "Cloning and expression in *Escherichia coli* of a cDNA coding for the oleoyl–acyl carrier protein thioesterase from coriander (*Coriandrum sativum* L.)", Biochimcia Et Biiophysica Acta, vol. 1212, pp. 134–136, (1994).

Dörmann, et al., "Cloning and expression in *Escherichia coli* of a novel thioesterase from *Arabidopsis thaliana* specific for long chain acyl–acyl carrier proteins", Arch Biochem Biophys., Jan. 10, vol. 316, No. 1, pp. 612–618 (1995).

Dörmann, et al., "Specificity of the Acyl–Acyl Carrier Protein (ACP) Thioesterase and Glycerol–3–Phosphate Acyltransferase for Octadecenoyl–ACP Isoners", Plant Physiol, vol. 104, pp. 839–844 (1994).

Eccleston, et al., "Medium–chain fatty acid biosynthesis and utilization in *Brassica napus* plants expressing lauroyl–acyl carrier protein thioesterase", Planta, vol. 198, pp. 46–53, (1996).

Grellet et al., "*Arabidopsis thaliana* systematic cDNA sequencing reveals a gene with homology with *Umbellularia californica* C12:0–ACP thioesterase", Plant Physiol Biochem. vol. 31, No. 4, pp. 599–602 (1993).

(List continued on next page.)

Primary Examiner—Amy J. Nelson
(74) Attorney, Agent, or Firm—Donald R. Stuart; Andrea T. Boruki

(57) ABSTRACT

Genes encoding maize oleoyl-ACP and palmitoyl-ACP thioesterase enzymes have been isolated from maize. These genes, when expressed in a plant, can be used to create transgenic plants having altered palmitic acid oil profiles.

16 Claims, No Drawings

OTHER PUBLICATIONS

Griffiths, et al., "Acyl–Thioesterase Activity in Developing Seeds of Cocoa", Phytochemistry, vol. 32, No. 6, pp. 1403–1405, (1993).

Hellyer, et al. "Induction, purification and characterization of acyl–ACP thioesterase from developing seeds of oil seed rape (*Brassica napus*)", Plant Molecular Biology, vol. 20, pp. 763–780, (1992).

Jones, et al., "Palmitoyl–Acyl Carrier Protein (ACP) Thioesterase and the Evolutionary Origin of Plant Acyl–ACP Thioesterases", The Plant Cell, vol. 7, pp. 359–371, (1995).

Joyard, et al., "Characterization of an Acyl–Coenzyme A Thioesterase Associated with the Envelope of Spinach Chloroplasts", Plant Physiol, vol. 65, pp. 1039–1043, (1980).

Kang et al., "Biochemical Characteristics of a Palmitoyl Acyl Carrier Protein Thioesterase Purified from *Iris pseudoacorus*", J. Biochem. Mol. Biol, vol. 29, No. 5, pp. 436–441, ((1996).

Knutzon, et al., "Isolation and Characterization of Two Safflower Oleoyl–Acyl Carrier Protein Thioesterase cDNA Clones", Plant Physiol, vol. 100, pp. 1751–1758, (1992).

Larson, et al., "Isolation and Characterization of an Acyl–CoA Thioesterase From Dark–Green *Euglena gracilis*", Archives of Biochemistry and Biophysics, vol. , No. 1, pp. 27–37 (1985).

Liu, et al., "Discovery of an Epidermal Stearoyl–Acyl Carrier Protein Thioesterase", The Journal of Biological Chemistry, vol. 270, No. 28, pp. 16962–16969, (1995).

Loader, et al., "Isolation and characterization of two *Brassica napus* embryo acyl–ACP thioesterase cDNA clones", Plant Molecular Biology, vol. 23, pp. 769–778, (1993).

McKeon et al., "Purification and Characterization of the Stearoyl–Acyl Carrier Protein Desaturase and the Acyl–Acyl Carrier Protein Thioesterase From Maturing Seeds of Safflower", The Journal of Biological Chemistry, Oct. 25, pp. 12141–12147, (1982).

Ohlrogge et al., "Alteration of Acyl–Acyl Carrier Protein Pools and Acetyl–CoA Carboxylase Expression in *Escherichia coli* by Plant Medium Chain Acyl–Acyl Carrier", Archives of Biochemistry and Biophysics, vol. 317, No. 1, Feb. 20, pp. 185–190, (1995).

Ohlrogge, et al., "Fat Metabolism in Higher Plants, Characterization of Plant Acyl–ACP and Acyl–CoA Hydrolases", Archives of Biochemistry and Biophysics, vol. 189, No. 2, Aug., pp. 382–391, (1978).

Pollard, et al., "A Specific Acyl–ACP Thioesterase Implicated in Medium–Chain Fatty Acid Production in Immature Cotyledons of *Umbellularia californica*", Archives of Biochemistry and Biophysics, vol. 284, No. 2, Feb. 1, pp. 306–312, (1991).

Shine, et al., "Fat Metabolism In Higher Plants, The Function of Acyl Thioesterase in the Metabolism of Acyl–Coenzymes A and Acyl–Acyl Carrier Proteins", Archives of Biochemistry and Biophysics, vol. 172, pp. 110–116, (1976).

Yuan, et al., "The Catalytic Cysteine and Histidine in the Plant Acyl–Acyl Carrier Protein Thioesterases", The Journal of Biological Chemistry, vol. 271, No. 7, Feb. 16, pp. 3417–3419, (1996).

Voelker et al., "Alteration of the Specificity and Regulation of Fatty Acid Synthesis of *Escherichia coli* by Expression of a Plant Medium–Chain Acyl–Acyl Carrier Protein Thioesterase", Journal of Bacteriology, Dec., pp. 7320–7327, (1994).

Voelker et al., "Fatty Acid Biosynthesis Redirected to Medium Chains in Transgenic Oilseed Plant", Science, vol. 257, Jul. 3, pp. 72–74, (1992).

Voelker et al., "Genetic Engineering of a Quantitative Trait, Metabolic and Genetic Parameters Influencing the Accumulation of Laurate in Rapeseed", The Plant Journal, vol. 9, No. 2, pp. 229–241, (1996).

Yuan et al., "Modification of the Substrate Specificity of an Acyl–Acyl Carrier Protein Thioesterase by Protein Engineering", Proc. Natl. Acad. Sci, USA, vol. 92, Nov., pp. 10639–10643,, (1995).

Stam M, et al. "The silence of genes in transgenic plants." Ann. Bot. 79:3–12, 1997.*

Koziel MG, et al. "Optimizing expression of transgenes with an emphasis on post–transcriptional events." Plant Mol. Biol. 32: 393–405, 1996.*

Smith CJS, et al. "Antisense RNA inhibition of polygalacturonase gene expression in transgenic tomatoes." Nature 334: 724–726, Aug. 25, 1988.*

Belanger FC, et al. "Molecular basis for allelic polymorphism of the maize globulin–1 gene." Genetics 129: 863–872, Nov. 1991.*

Davies, et al., "Mechanisms of Chain Length Determination and Medium–Chain Fatty Acid Biosynthesis", The American Society of Plant Physiologists, vol. 9, pp 133–137, (1993).

Voelker, Toni, "Plant Acyl–Acp Thioesterases: Chain–Length Determining Enzymes in Plant Fatty Acid Biosynthesis", Genetic Engineering, vol. 18, pp 111–133 (1996).

Belanger, F. C. and Kriz, A. L.: "sequence of the maize globulin–1 allele, upstream 5' flank", EMBL Sequence Data Library, Nov. 21, 1993, Accession No. L22344.

* cited by examiner

SEQUENCE LISTING (1) GENERAL INFORMATION:

(iii) NUMBER OF SEQUENCES: 49

(2) INFORMATION FOR SEQ ID NO:1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

GTNTTYMGNC ARAAYTT                 17

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

RTTCATCATN ACCCAYTT                18

(2) INFORMATION FOR SEQ ID NO:3:

(i) SEQUENCE CHARACTERISTICS:
      (A) LENGTH: 354 base pairs
      (B) TYPE: nucleic acid
      (C) STRANDEDNESS: single (D) TOPOLOGY: linear (ii) MOLECULE TYPE: DNA (ix) FEATURE:
        (A) NAME/KEY: CDS
        (B) LOCATION: 1..354

(xi) SEQUENCE DESCRIPTION: SEQ ID NO:3:

```
GTG TTC AGG CAG AAC TTC TCC ATT AGG TCC TAC GAG ATT GGG GCA GAT      48
Val Phe Arg Gln Asn Phe Ser Ile Arg Ser Tyr Glu Ile Gly Ala Asp
 1               5                  10                  15

AGG ACG GCA TCT ATA GAG ACG CTG ATG AAC CAT TTG CAG GAA ACG GCA      96
Arg Thr Ala Ser Ile Glu Thr Leu Met Asn His Leu Gln Glu Thr Ala
            20                  25                  30

CTC AAT CAT GTG AAG ACC GCT GGG CTG CTA GGT GAT GGA TTT GGC TCC     144
Leu Asn His Val Lys Thr Ala Gly Leu Leu Gly Asp Gly Phe Gly Ser
        35                  40                  45

ACA CCA GAG ATG AGT AAA CGA AAC TTG TTC TGG GTG GTT AGC CAA ATG     192
Thr Pro Glu Met Ser Lys Arg Asn Leu Phe Trp Val Val Ser Gln Met
    50                  55                  60

CAG GCC ATC ATC GAG CGT TAT CCA TGC TGG GGT GAT ACT GTT GAA GTA     240
Gln Ala Ile Ile Glu Arg Tyr Pro Cys Trp Gly Asp Thr Val Glu Val
65                  70                  75                  80

GAT ACA TGG GTT AGT GCT AAT GGT AAA AAT GGA ATG CGT AGG GAT TGG     288
Asp Thr Trp Val Ser Ala Asn Gly Lys Asn Gly Met Arg Arg Asp Trp
                85                  90                  95

CAT ATA CGT GAT CCT ATA ACA GGC CTC ACG ATA CTG AAG GCA ACA AGT     336
His Ile Arg Asp Pro Ile Thr Gly Leu Thr Ile Leu Lys Ala Thr Ser
            100                 105                 110

AAA TGG GTT ATG ATG AAC                                             354
Lys Trp Val Met Met Asn
        115
```

(2) INFORMATION FOR SEQ ID NO:4:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:4:

```
Val Phe Arg Gln Asn Phe Ser Ile Arg Ser Tyr Glu Ile Gly Ala Asp
 1               5                  10                  15

Arg Thr Ala Ser Ile Glu Thr Leu Met Asn His Leu Gln Glu Thr Ala
            20                  25                  30

Leu Asn His Val Lys Thr Ala Gly Leu Leu Gly Asp Gly Phe Gly Ser
        35                  40                  45

Thr Pro Glu Met Ser Lys Arg Asn Leu Phe Trp Val Val Ser Gln Met
    50                  55                  60

Gln Ala Ile Ile Glu Arg Tyr Pro Cys Trp Gly Asp Thr Val Glu Val
65                  70                  75                  80

Asp Thr Trp Val Ser Ala Asn Gly Lys Asn Gly Met Arg Arg Asp Trp
                85                  90                  95

His Ile Arg Asp Pro Ile Thr Gly Leu Thr Ile Leu Lys Ala Thr Ser
            100                 105                 110

Lys Trp Val Met Met Asn
        115
```

(2) INFORMATION FOR SEQ ID NO:5:

(i) SEQUENCE CHARACTERISTICS:
        (A) LENGTH: 1777 base pairs
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: Zea Mays (ix) FEATURE:
        (A) NAME/KEY: CDS
        (B) LOCATION: 55..1311

(ix) FEATURE:
        (A) NAME/KEY: mat_peptide
        (B) LOCATION: 322..1311

(xi) SEQUENCE DESCRIPTION: SEQ ID NO:5:

```
CCGGATTCAG ACAGGTGCTA CCATTCGATT TGATTTGGCG CGGACCACTT TCCT ATG        57
                                                            Met
                                                            -89

GCC GCC TCC ATC GCG GCC TCG TCC TTC TTT CCA GGG TCA CCG GCG CCG       105
Ala Ala Ser Ile Ala Ala Ser Ser Phe Phe Pro Gly Ser Pro Ala Pro
            -85                 -80                 -75

GCC GCT CCT AAG AAC GGC CTT GGG GAG CGC CCA GAG AGC CTG GAC GTC       153
Ala Ala Pro Lys Asn Gly Leu Gly Glu Arg Pro Glu Ser Leu Asp Val
        -70                 -65                 -60

CGC GGC GTT GCG GCG AAG CCG GGA GCC TCG TCG TCT AGT GCC GTG AGG       201
Arg Gly Val Ala Ala Lys Pro Gly Ala Ser Ser Ser Ser Ala Val Arg
    -55                 -50                 -45

GCG GGC AAG ACG CGC GCC CAC GCT GCG GTC CCC AAG ATG AAC GGT GGG       249
Ala Gly Lys Thr Arg Ala His Ala Ala Val Pro Lys Met Asn Gly Gly
-40                 -35                 -30                 -25

GGC AAG TCC GCG GTG GCG GAT GGG GAG CAC GAA ACC GTA CCT TCT TCG       297
Gly Lys Ser Ala Val Ala Asp Gly Glu His Glu Thr Val Pro Ser Ser
                -20                 -15                 -10

GTG CCG AAG ACT TTC TAC AAC CAG CTT CCC GAC TGG AGC ATG CTC CTT       345
Val Pro Lys Thr Phe Tyr Asn Gln Leu Pro Asp Trp Ser Met Leu Leu
            -5                   1                   5

GCG GCC ATC ACC ACC ATC TTC TTG GCC GCA GAG AAG CAG TGG ACG ATG       393
Ala Ala Ile Thr Thr Ile Phe Leu Ala Ala Glu Lys Gln Trp Thr Met
         10                  15                  20

CTT GAC TGG AAG CCT AGG AGG CCT GAC ATG CTC ACT GAC ACG TTT GGG       441
Leu Asp Trp Lys Pro Arg Arg Pro Asp Met Leu Thr Asp Thr Phe Gly
 25                  30                  35                  40

TTT GGC CGG ATC ATA CAT GAT GGG CTC ATG TTC AGG CAG AAC TTC TCC       489
Phe Gly Arg Ile Ile His Asp Gly Leu Met Phe Arg Gln Asn Phe Ser
                 45                  50                  55

ATT AGG TCC TAC GAG ATT GGG GCA GAT AGG ACG GCA TCT ATA GAG ACG       537
Ile Arg Ser Tyr Glu Ile Gly Ala Asp Arg Thr Ala Ser Ile Glu Thr
                 60                  65                  70

CTG ATG AAC CAT TTG CAG GAA ACG GCA CTC AAT CAT GTG AAG ACC GCT       585
Leu Met Asn His Leu Gln Glu Thr Ala Leu Asn His Val Lys Thr Ala
             75                  80                  85

GGG CTG CTA GGT GAT GGA TTT GGC TCC ACA CCA GAG ATG AGT AAA CGA       633
Gly Leu Leu Gly Asp Gly Phe Gly Ser Thr Pro Glu Met Ser Lys Arg
         90                  95                 100

AAC TTG TTC TGG GTG GTT AGC CAA ATG CAG GCC ATC ATC GAG CGT TAT       681
Asn Leu Phe Trp Val Val Ser Gln Met Gln Ala Ile Ile Glu Arg Tyr
105                 110                 115                 120
```

```
CCA TGC TGG GGT GAT ACT GTT GAA GTA GAT ACA TGG GTT AGT GCT AAT      729
Pro Cys Trp Gly Asp Thr Val Glu Val Asp Thr Trp Val Ser Ala Asn
                125                 130                 135

GGT AAA AAT GGA ATG CGT AGG GAT TGG CAT ATA CGT GAT CCT ATA ACA      777
Gly Lys Asn Gly Met Arg Arg Asp Trp His Ile Arg Asp Pro Ile Thr
            140                 145                 150

GGC CTC ACG ATA CTG AAG GCA ACA AGT AAA TGG GTT ATG ATG AAC AAA      825
Gly Leu Thr Ile Leu Lys Ala Thr Ser Lys Trp Val Met Met Asn Lys
        155                 160                 165

CTC ACT AGG AAG CTT GCA AGA ATT CCA GAT GAA GTG CGG ACT GAA ATA      873
Leu Thr Arg Lys Leu Ala Arg Ile Pro Asp Glu Val Arg Thr Glu Ile
    170                 175                 180

GAG CCA TAC TTT TTT GAG CAT TCT GCT ATT GTT GAC GAA GAC AAC CGC      921
Glu Pro Tyr Phe Phe Glu His Ser Ala Ile Val Asp Glu Asp Asn Arg
185                 190                 195                 200

AAG CTT CCA AAA CTG CCA GAG GGA CAA AGC ACT TCT GTA GCT AAA TAT      969
Lys Leu Pro Lys Leu Pro Glu Gly Gln Ser Thr Ser Val Ala Lys Tyr
                205                 210                 215

GTG AGG ACA GGC CTG ACT CCT CGC TGG GCT GAT CTT GAT ATA AAT CAG     1017
Val Arg Thr Gly Leu Thr Pro Arg Trp Ala Asp Leu Asp Ile Asn Gln
            220                 225                 230

CAT GTC AAT AAT GTT AAA TAC ATT GCG TGG ATC CTT GAG AGT GCA CCC     1065
His Val Asn Asn Val Lys Tyr Ile Ala Trp Ile Leu Glu Ser Ala Pro
        235                 240                 245

ATC TCT ATT CTT GAG AAT CAT GAG CTG GCG AGC ATT GTG CTG GAT TAC     1113
Ile Ser Ile Leu Glu Asn His Glu Leu Ala Ser Ile Val Leu Asp Tyr
    250                 255                 260

AAA AGG GAG TGT GGC CGG GAT AGT GTG CTG CAA TCA CAC ACC TCT GTG     1161
Lys Arg Glu Cys Gly Arg Asp Ser Val Leu Gln Ser His Thr Ser Val
265                 270                 275                 280

CAC ACG GAT TGC AAC AGT GAG TCT GGA GAA ACA ACC TTG CAC TGT GAG     1209
His Thr Asp Cys Asn Ser Glu Ser Gly Glu Thr Thr Leu His Cys Glu
                285                 290                 295

CAT GTG CTG AGC CTT GAA TCA GGC CCG ACC ATG GTG AAG GCC CGG ACC     1257
His Val Leu Ser Leu Glu Ser Gly Pro Thr Met Val Lys Ala Arg Thr
            300                 305                 310

ATG TGG AGG CCT AAG GGA ACC AAG GCC CAA GAA ACA GTG GTT CCA TCT     1305
Met Trp Arg Pro Lys Gly Thr Lys Ala Gln Glu Thr Val Val Pro Ser
        315                 320                 325

TCA ATT TGAATTGTGT GAGACGTTCG GGATGGTGAT TTTGGCAGCA AACTACTACT     1361
Ser Ile
    330

ATTTGCCAAA AAGATCAGAA TGGTTACTAG CGTCCTCTAT TGGAAGCAAG TCACACAGGG  1421

CGAGACCTAA ACTAATTTAA TTATGAAGTG TGAACAATAG AGGAGATATA AATAGTGTGA  1481

ACNATGGACT GGAAGAGACA GAAGCGGGGG GAGANCGAAG ACAAGGGAGC CCTCATGTGC  1541

ATGACAATCT TCGGTCGCAC AAATGGGTGT TGTAAGTATT GATCTGTAAG CTACAAATGT  1601

ATGAAGGGGA GTGAGTGCTT CCCAAACATG TTCCTTCTGG GGCTATGTCC ATATGCTATA  1661

ACCCCCCCGA AAACATTGTC GCAGCCATAT ATTCATTCAG AGGATTTTAA TCTCGTACGT  1721

ATATTGTATT TGCTGATATT AAGATTGATA TTATTACTAA AAAAAAAAAA AAAAAA      1777

(2) INFORMATION FOR SEQ ID NO:6:

(i) SEQUENCE CHARACTERISTICS:
        (A) LENGTH: 1257 base pairs
        (B) TYPE: nucleic acid
        (C) STRANDEDNESS: single
        (D) TOPOLOGY: linear
```

-continued

```
    (ii) MOLECULE TYPE: DNA (vi) ORIGINAL SOURCE:
         (A) ORGANISM: Zea Mays (ix) FEATURE:
         (A) NAME/KEY: CDS
         (B) LOCATION: 1..1257

(ix) FEATURE:
         (A) NAME/KEY: mat_peptide
         (B) LOCATION: 268..1257

(xi) SEQUENCE DESCRIPTION: SEQ ID NO:6:

ATG GCC GCC TCC ATC GCG GCC TCG TCC TTC TTT CCA GGG TCA CCG GCG        48
Met Ala Ala Ser Ile Ala Ala Ser Ser Phe Phe Pro Gly Ser Pro Ala
-89             -85             -80             -75

CCG GCC GCT CCT AAG AAC GGC CTT GGG GAG CGC CCA GAG AGC CTG GAC        96
Pro Ala Ala Pro Lys Asn Gly Leu Gly Glu Arg Pro Glu Ser Leu Asp
            -70             -65             -60

GTC CGC GGC GTT GCG GCG AAG CCG GGA GCC TCG TCG TCT AGT GCC GTG       144
Val Arg Gly Val Ala Ala Lys Pro Gly Ala Ser Ser Ser Ser Ala Val
        -55             -50             -45

AGG GCG GGC AAG ACG CGC GCC CAC GCT GCG GTC CCC AAG ATG AAC GGT       192
Arg Ala Gly Lys Thr Arg Ala His Ala Ala Val Pro Lys Met Asn Gly
    -40             -35             -30

GGG GGC AAG TCC GCG GTG GCG GAT GGG GAG CAC GAA ACC GTA CCT TCT       240
Gly Gly Lys Ser Ala Val Ala Asp Gly Glu His Glu Thr Val Pro Ser
-25             -20             -15             -10

TCG GTG CCG AAG ACT TTC TAC AAC CAG CTT CCC GAC TGG AGC ATG CTC       288
Ser Val Pro Lys Thr Phe Tyr Asn Gln Leu Pro Asp Trp Ser Met Leu
            -5               1               5

CTT GCG GCC ATC ACC ACC ATC TTC TTG GCC GCA GAG AAG CAG TGG ACG       336
Leu Ala Ala Ile Thr Thr Ile Phe Leu Ala Ala Glu Lys Gln Trp Thr
         10              15              20

ATG CTT GAC TGG AAG CCT AGG AGG CCT GAC ATG CTC ACT GAC ACG TTT       384
Met Leu Asp Trp Lys Pro Arg Arg Pro Asp Met Leu Thr Asp Thr Phe
     25              30              35

GGG TTT GGC CGG ATC ATA CAT GAT GGG CTC ATG TTC AGG CAG AAC TTC       432
Gly Phe Gly Arg Ile Ile His Asp Gly Leu Met Phe Arg Gln Asn Phe
 40              45              50                          55

TCC ATT AGG TCC TAC GAG ATT GGG GCA GAT AGG ACG GCA TCT ATA GAG       480
Ser Ile Arg Ser Tyr Glu Ile Gly Ala Asp Arg Thr Ala Ser Ile Glu
             60              65              70

ACG CTG ATG AAC CAT TTG CAG GAA ACG GCA CTC AAT CAT GTG AAG ACC       528
Thr Leu Met Asn His Leu Gln Glu Thr Ala Leu Asn His Val Lys Thr
         75              80              85

GCT GGG CTG CTA GGT GAT GGA TTT GGC TCC ACA CCA GAG ATG AGT AAA       576
Ala Gly Leu Leu Gly Asp Gly Phe Gly Ser Thr Pro Glu Met Ser Lys
     90              95             100

CGA AAC TTG TTC TGG GTG GTT AGC CAA ATG CAG GCC ATC ATC GAG CGT       624
Arg Asn Leu Phe Trp Val Val Ser Gln Met Gln Ala Ile Ile Glu Arg
105             110             115

TAT CCA TGC TGG GGT GAT ACT GTT GAA GTA GAT ACA TGG GTT AGT GCT       672
Tyr Pro Cys Trp Gly Asp Thr Val Glu Val Asp Thr Trp Val Ser Ala
120             125             130             135

AAT GGT AAA AAT GGA ATG CGT AGG GAT TGG CAT ATA CGT GAT CCT ATA       720
Asn Gly Lys Asn Gly Met Arg Arg Asp Trp His Ile Arg Asp Pro Ile
            140             145             150

ACA GGC CTC ACG ATA CTG AAG GCA ACA AGT AAA TGG GTT ATG ATG AAC       768
Thr Gly Leu Thr Ile Leu Lys Ala Thr Ser Lys Trp Val Met Met Asn
        155             160             165
```

```
AAA CTC ACT AGG AAG CTT GCA AGA ATT CCA GAT GAA GTG CGG ACT GAA      816
Lys Leu Thr Arg Lys Leu Ala Arg Ile Pro Asp Glu Val Arg Thr Glu
        170                 175                 180

ATA GAG CCA TAC TTT TTT GAG CAT TCT GCT ATT GTT GAC GAA GAC AAC      864
Ile Glu Pro Tyr Phe Phe Glu His Ser Ala Ile Val Asp Glu Asp Asn
185                 190                 195

CGC AAG CTT CCA AAA CTG CCA GAG GGA CAA AGC ACT TCT GTA GCT AAA      912
Arg Lys Leu Pro Lys Leu Pro Glu Gly Gln Ser Thr Ser Val Ala Lys
200                 205                 210                 215

TAT GTG AGG ACA GGC CTG ACT CCT CGC TGG GCT GAT CTT GAT ATA AAT      960
Tyr Val Arg Thr Gly Leu Thr Pro Arg Trp Ala Asp Leu Asp Ile Asn
                220                 225                 230

CAG CAT GTC AAT AAT GTT AAA TAC ATT GCG TGG ATC CTT GAG AGT GCA     1008
Gln His Val Asn Asn Val Lys Tyr Ile Ala Trp Ile Leu Glu Ser Ala
            235                 240                 245

CCC ATC TCT ATT CTT GAG AAT CAT GAG CTG GCG AGC ATT GTG CTG GAT     1056
Pro Ile Ser Ile Leu Glu Asn His Glu Leu Ala Ser Ile Val Leu Asp
        250                 255                 260

TAC AAA AGG GAG TGT GGC CGG GAT AGT GTG CTG CAA TCA CAC ACC TCT     1104
Tyr Lys Arg Glu Cys Gly Arg Asp Ser Val Leu Gln Ser His Thr Ser
265                 270                 275

GTG CAC ACG GAT TGC AAC AGT GAG TCT GGA GAA ACA ACC TTG CAC TGT     1152
Val His Thr Asp Cys Asn Ser Glu Ser Gly Glu Thr Thr Leu His Cys
280                 285                 290                 295

GAG CAT GTG CTG AGC CTT GAA TCA GGC CCG ACC ATG GTG AAG GCC CGG     1200
Glu His Val Leu Ser Leu Glu Ser Gly Pro Thr Met Val Lys Ala Arg
                300                 305                 310

ACC ATG TGG AGG CCT AAG GGA ACC AAG GCC CAA GAA ACA GTG GTT CCA     1248
Thr Met Trp Arg Pro Lys Gly Thr Lys Ala Gln Glu Thr Val Val Pro
            315                 320                 325

TCT TCA ATT                                                          1257
Ser Ser Ile
        330

(2) INFORMATION FOR SEQ ID NO:7:

(i) SEQUENCE CHARACTERISTICS:
        (A) LENGTH: 419 amino acids
        (B) TYPE: amino acid
        (D) TOPOLOGY: linear (ii) MOLECULE TYPE: protein (xi) SEQUENCE DESCRIPTION: SEQ ID NO:7:

Met Ala Ala Ser Ile Ala Ala Ser Ser Phe Phe Pro Gly Ser Pro Ala
-89             -85                 -80                 -75

Pro Ala Ala Pro Lys Asn Gly Leu Gly Glu Arg Pro Glu Ser Leu Asp
            -70                 -65                 -60

Val Arg Gly Val Ala Ala Lys Pro Gly Ala Ser Ser Ser Ser Ala Val
        -55                 -50                 -45

Arg Ala Gly Lys Thr Arg Ala His Ala Ala Val Pro Lys Met Asn Gly
    -40                 -35                 -30

Gly Gly Lys Ser Ala Val Ala Asp Gly Glu His Glu Thr Val Pro Ser
-25                 -20                 -15                 -10

Ser Val Pro Lys Thr Phe Tyr Asn Gln Leu Pro Asp Trp Ser Met Leu
                -5                   1                   5

Leu Ala Ala Ile Thr Thr Ile Phe Leu Ala Ala Glu Lys Gln Trp Thr
            10                  15                  20

Met Leu Asp Trp Lys Pro Arg Arg Pro Asp Met Leu Thr Asp Thr Phe
    25                  30                  35
```

```
Gly Phe Gly Arg Ile Ile His Asp Gly Leu Met Phe Arg Gln Asn Phe
 40                  45                  50                  55

Ser Ile Arg Ser Tyr Glu Ile Gly Ala Asp Arg Thr Ala Ser Ile Glu
                 60                  65                  70

Thr Leu Met Asn His Leu Gln Glu Thr Ala Leu Asn His Val Lys Thr
             75                  80                  85

Ala Gly Leu Leu Gly Asp Gly Phe Gly Ser Thr Pro Glu Met Ser Lys
         90                  95                 100

Arg Asn Leu Phe Trp Val Val Ser Gln Met Gln Ala Ile Ile Glu Arg
    105                 110                 115

Tyr Pro Cys Trp Gly Asp Thr Val Glu Val Asp Thr Trp Val Ser Ala
120                 125                 130                 135

Asn Gly Lys Asn Gly Met Arg Arg Asp Trp His Ile Arg Asp Pro Ile
                140                 145                 150

Thr Gly Leu Thr Ile Leu Lys Ala Thr Ser Lys Trp Val Met Met Asn
            155                 160                 165

Lys Leu Thr Arg Lys Leu Ala Arg Ile Pro Asp Glu Val Arg Thr Glu
        170                 175                 180

Ile Glu Pro Tyr Phe Phe Glu His Ser Ala Ile Val Asp Glu Asp Asn
    185                 190                 195

Arg Lys Leu Pro Lys Leu Pro Glu Gly Gln Ser Thr Ser Val Ala Lys
200                 205                 210                 215

Tyr Val Arg Thr Gly Leu Thr Pro Arg Trp Ala Asp Leu Asp Ile Asn
                220                 225                 230

Gln His Val Asn Asn Val Lys Tyr Ile Ala Trp Ile Leu Glu Ser Ala
            235                 240                 245

Pro Ile Ser Ile Leu Glu Asn His Glu Leu Ala Ser Ile Val Leu Asp
        250                 255                 260

Tyr Lys Arg Glu Cys Gly Arg Asp Ser Val Leu Gln Ser His Thr Ser
    265                 270                 275

Val His Thr Asp Cys Asn Ser Glu Ser Gly Glu Thr Thr Leu His Cys
280                 285                 290                 295

Glu His Val Leu Ser Leu Glu Ser Gly Pro Thr Met Val Lys Ala Arg
                300                 305                 310

Thr Met Trp Arg Pro Lys Gly Thr Lys Ala Gln Glu Thr Val Val Pro
            315                 320                 325

Ser Ser Ile
        330

(2) INFORMATION FOR SEQ ID NO:8:

(i) SEQUENCE CHARACTERISTICS:
        (A) LENGTH: 990 base pairs
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: Zea Mays (ix) FEATURE:
        (A) NAME/KEY: CDS
        (B) LOCATION: 1..990

(xi) SEQUENCE DESCRIPTION: SEQ ID NO:8:

CTT CCC GAC TGG AGC ATG CTC CTT GCG GCC ATC ACC ACC ATC TTC TTG      48
```

```
Leu Pro Asp Trp Ser Met Leu Leu Ala Ala Ile Thr Thr Ile Phe Leu
 1               5                  10                  15

GCC GCA GAG AAG CAG TGG ACG ATG CTT GAC TGG AAG CCT AGG AGG CCT      96
Ala Ala Glu Lys Gln Trp Thr Met Leu Asp Trp Lys Pro Arg Arg Pro
             20                  25                  30

GAC ATG CTC ACT GAC ACG TTT GGG TTT GGC CGG ATC ATA CAT GAT GGG     144
Asp Met Leu Thr Asp Thr Phe Gly Phe Gly Arg Ile Ile His Asp Gly
             35                  40                  45

CTC ATG TTC AGG CAG AAC TTC TCC ATT AGG TCC TAC GAG ATT GGG GCA     192
Leu Met Phe Arg Gln Asn Phe Ser Ile Arg Ser Tyr Glu Ile Gly Ala
 50                  55                  60

GAT AGG ACG GCA TCT ATA GAG ACG CTG ATG AAC CAT TTG CAG GAA ACG     240
Asp Arg Thr Ala Ser Ile Glu Thr Leu Met Asn His Leu Gln Glu Thr
 65                  70                  75                  80

GCA CTC AAT CAT GTG AAG ACC GCT GGG CTG CTA GGT GAT GGA TTT GGC     288
Ala Leu Asn His Val Lys Thr Ala Gly Leu Leu Gly Asp Gly Phe Gly
             85                  90                  95

TCC ACA CCA GAG ATG AGT AAA CGA AAC TTG TTC TGG GTG GTT AGC CAA     336
Ser Thr Pro Glu Met Ser Lys Arg Asn Leu Phe Trp Val Val Ser Gln
            100                 105                 110

ATG CAG GCC ATC ATC GAG CGT TAT CCA TGC TGG GGT GAT ACT GTT GAA     384
Met Gln Ala Ile Ile Glu Arg Tyr Pro Cys Trp Gly Asp Thr Val Glu
            115                 120                 125

GTA GAT ACA TGG GTT AGT GCT AAT GGT AAA AAT GGA ATG CGT AGG GAT     432
Val Asp Thr Trp Val Ser Ala Asn Gly Lys Asn Gly Met Arg Arg Asp
130                 135                 140

TGG CAT ATA CGT GAT CCT ATA ACA GGC CTC ACG ATA CTG AAG GCA ACA     480
Trp His Ile Arg Asp Pro Ile Thr Gly Leu Thr Ile Leu Lys Ala Thr
145                 150                 155                 160

AGT AAA TGG GTT ATG ATG AAC AAA CTC ACT AGG AAG CTT GCA AGA ATT     528
Ser Lys Trp Val Met Met Asn Lys Leu Thr Arg Lys Leu Ala Arg Ile
                165                 170                 175

CCA GAT GAA GTG CGG ACT GAA ATA GAG CCA TAC TTT TTT GAG CAT TCT     576
Pro Asp Glu Val Arg Thr Glu Ile Glu Pro Tyr Phe Phe Glu His Ser
            180                 185                 190

GCT ATT GTT GAC GAA GAC AAC CGC AAG CTT CCA AAA CTG CCA GAG GGA     624
Ala Ile Val Asp Glu Asp Asn Arg Lys Leu Pro Lys Leu Pro Glu Gly
            195                 200                 205

CAA AGC ACT TCT GTA GCT AAA TAT GTG AGG ACA GGC CTG ACT CCT CGC     672
Gln Ser Thr Ser Val Ala Lys Tyr Val Arg Thr Gly Leu Thr Pro Arg
            210                 215                 220

TGG GCT GAT CTT GAT ATA AAT CAG CAT GTC AAT AAT GTT AAA TAC ATT     720
Trp Ala Asp Leu Asp Ile Asn Gln His Val Asn Asn Val Lys Tyr Ile
225                 230                 235                 240

GCG TGG ATC CTT GAG AGT GCA CCC ATC TCT ATT CTT GAG AAT CAT GAG     768
Ala Trp Ile Leu Glu Ser Ala Pro Ile Ser Ile Leu Glu Asn His Glu
                245                 250                 255

CTG GCG AGC ATT GTG CTG GAT TAC AAA AGG GAG TGT GGC CGG GAT AGT     816
Leu Ala Ser Ile Val Leu Asp Tyr Lys Arg Glu Cys Gly Arg Asp Ser
            260                 265                 270

GTG CTG CAA TCA CAC ACC TCT GTG CAC ACG GAT TGC AAC AGT GAG TCT     864
Val Leu Gln Ser His Thr Ser Val His Thr Asp Cys Asn Ser Glu Ser
            275                 280                 285

GGA GAA ACA ACC TTG CAC TGT GAG CAT GTG CTG AGC CTT GAA TCA GGC     912
Gly Glu Thr Thr Leu His Cys Glu His Val Leu Ser Leu Glu Ser Gly
            290                 295                 300

CCG ACC ATG GTG AAG GCC CGG ACC ATG TGG AGG CCT AAG GGA ACC AAG     960
Pro Thr Met Val Lys Ala Arg Thr Met Trp Arg Pro Lys Gly Thr Lys
305                 310                 315                 320
```

```
GCC CAA GAA ACA GTG GTT CCA TCT TCA ATT                              990
Ala Gln Glu Thr Val Val Pro Ser Ser Ile
            325                 330

(2) INFORMATION FOR SEQ ID NO:9:

(i) SEQUENCE CHARACTERISTICS:
        (A) LENGTH: 330 amino acids
        (B) TYPE: amino acid
        (D) TOPOLOGY: linear (ii) MOLECULE TYPE: protein (xi) SEQUENCE DESCRIPTION: SEQ ID NO:9:

Leu Pro Asp Trp Ser Met Leu Leu Ala Ala Ile Thr Thr Ile Phe Leu
 1               5                  10                  15

Ala Ala Glu Lys Gln Trp Thr Met Leu Asp Trp Lys Pro Arg Arg Pro
             20                  25                  30

Asp Met Leu Thr Asp Thr Phe Gly Phe Gly Arg Ile Ile His Asp Gly
         35                  40                  45

Leu Met Phe Arg Gln Asn Phe Ser Ile Arg Ser Tyr Glu Ile Gly Ala
     50                  55                  60

Asp Arg Thr Ala Ser Ile Glu Thr Leu Met Asn His Leu Gln Glu Thr
 65                  70                  75                  80

Ala Leu Asn His Val Lys Thr Ala Gly Leu Leu Gly Asp Gly Phe Gly
                 85                  90                  95

Ser Thr Pro Glu Met Ser Lys Arg Asn Leu Phe Trp Val Val Ser Gln
            100                 105                 110

Met Gln Ala Ile Ile Glu Arg Tyr Pro Cys Trp Gly Asp Thr Val Glu
        115                 120                 125

Val Asp Thr Trp Val Ser Ala Asn Gly Lys Asn Gly Met Arg Arg Asp
    130                 135                 140

Trp His Ile Arg Asp Pro Ile Thr Gly Leu Thr Ile Leu Lys Ala Thr
145                 150                 155                 160

Ser Lys Trp Val Met Met Asn Lys Leu Thr Arg Lys Leu Ala Arg Ile
                165                 170                 175

Pro Asp Glu Val Arg Thr Glu Ile Glu Pro Tyr Phe Phe Glu His Ser
            180                 185                 190

Ala Ile Val Asp Glu Asp Asn Arg Lys Leu Pro Lys Leu Pro Glu Gly
        195                 200                 205

Gln Ser Thr Ser Val Ala Lys Tyr Val Arg Thr Gly Leu Thr Pro Arg
    210                 215                 220

Trp Ala Asp Leu Asp Ile Asn Gln His Val Asn Asn Val Lys Tyr Ile
225                 230                 235                 240

Ala Trp Ile Leu Glu Ser Ala Pro Ile Ser Ile Leu Glu Asn His Glu
                245                 250                 255

Leu Ala Ser Ile Val Leu Asp Tyr Lys Arg Glu Cys Gly Arg Asp Ser
            260                 265                 270

Val Leu Gln Ser His Thr Ser Val His Thr Asp Cys Asn Ser Glu Ser
        275                 280                 285

Gly Glu Thr Thr Leu His Cys Glu His Val Leu Ser Leu Glu Ser Gly
    290                 295                 300

Pro Thr Met Val Lys Ala Arg Thr Met Trp Arg Pro Lys Gly Thr Lys
305                 310                 315                 320

Ala Gln Glu Thr Val Val Pro Ser Ser Ile
                325                 330
```

(2) INFORMATION FOR SEQ ID NO:10:

(i) SEQUENCE CHARACTERISTICS:
        (A) LENGTH:  32 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:10:

```
ACGTACGTCA TATGCAGCTT CCCGACTGGA GC                                32
```

(2) INFORMATION FOR SEQ ID NO:11:

(i) SEQUENCE CHARACTERISTICS:
        (A) LENGTH:  35 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:11:

```
ACGTACGTCT CGAGTCAAAT TGAAGATGGA ACCAC                             35
```

(2) INFORMATION FOR SEQ ID NO:12:

(i) SEQUENCE CHARACTERISTICS:
        (A) LENGTH: 1024 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 12..1007

(xi) SEQUENCE DESCRIPTION: SEQ ID NO:12:

```
ACGTACGTCA T ATG CAG CTT CCC GAC TGG AGC ATG CTC CTT GCG GCC ATC      50
            Met Gln Leu Pro Asp Trp Ser Met Leu Leu Ala Ala Ile
             1               5                  10

ACC ACC ATC TTC TTG GCC GCA GAG AAG CAG TGG ACG ATG CTT GAC TGG       98
Thr Thr Ile Phe Leu Ala Ala Glu Lys Gln Trp Thr Met Leu Asp Trp
 15                  20                  25

AAG CCT AGG AGG CCT GAC ATG CTC ACT GAC ACG TTT GGG TTT GGC CGG      146
Lys Pro Arg Arg Pro Asp Met Leu Thr Asp Thr Phe Gly Phe Gly Arg
 30              35                  40                  45

ATC ATA CAT GAT GGG CTC ATG TTC AGG CAG AAC TTC TCC ATT AGG TCC      194
Ile Ile His Asp Gly Leu Met Phe Arg Gln Asn Phe Ser Ile Arg Ser
                 50                  55                  60

TAC GAG ATT GGG GCA GAT AGG ACG GCA TCT ATA GAG ACG CTG ATG AAC      242
Tyr Glu Ile Gly Ala Asp Arg Thr Ala Ser Ile Glu Thr Leu Met Asn
             65                  70                  75

CAT TTG CAG GAA ACG GCA CTC AAT CAT GTG AAG ACC GCT GGG CTG CTA      290
His Leu Gln Glu Thr Ala Leu Asn His Val Lys Thr Ala Gly Leu Leu
         80                  85                  90

GGT GAT GGA TTT GGC TCC ACA CCA GAG ATG AGT AAA CGA AAC TTG TTC      338
Gly Asp Gly Phe Gly Ser Thr Pro Glu Met Ser Lys Arg Asn Leu Phe
     95                 100                 105

TGG GTG GTT AGC CAA ATG CAG GCC ATC ATC GAG CGT TAT CCA TGC TGG      386
Trp Val Val Ser Gln Met Gln Ala Ile Ile Glu Arg Tyr Pro Cys Trp
110                 115                 120                 125
```

```
GGT GAT ACT GTT GAA GTA GAT ACA TGG GTT AGT GCT AAT GGT AAA AAT        434
Gly Asp Thr Val Glu Val Asp Thr Trp Val Ser Ala Asn Gly Lys Asn
            130                 135                 140

GGA ATG CGT AGG GAT TGG CAT ATA CGT GAT CCT ATA ACA GGC CTC ACG        482
Gly Met Arg Arg Asp Trp His Ile Arg Asp Pro Ile Thr Gly Leu Thr
        145                 150                 155

ATA CTG AAG GCA ACA AGT AAA TGG GTT ATG ATG AAC AAA CTC ACT AGG        530
Ile Leu Lys Ala Thr Ser Lys Trp Val Met Met Asn Lys Leu Thr Arg
            160                 165                 170

AAG CTT GCA AGA ATT CCA GAT GAA GTG CGG ACT GAA ATA GAG CCA TAC        578
Lys Leu Ala Arg Ile Pro Asp Glu Val Arg Thr Glu Ile Glu Pro Tyr
        175                 180                 185

TTT TTT GAG CAT TCT GCT ATT GTT GAC GAA GAC AAC CGC AAG CTT CCA        626
Phe Phe Glu His Ser Ala Ile Val Asp Glu Asp Asn Arg Lys Leu Pro
190                 195                 200                 205

AAA CTG CCT GAG GGA CAA AGC ACT TCT GTA GCT AAA TAT GTG AGG ACA        674
Lys Leu Pro Glu Gly Gln Ser Thr Ser Val Ala Lys Tyr Val Arg Thr
            210                 215                 220

GGC CTG ACT CCT CGC TGG GCT GAT CTT GAT ATA AAT CAG CAT GTC AAT        722
Gly Leu Thr Pro Arg Trp Ala Asp Leu Asp Ile Asn Gln His Val Asn
        225                 230                 235

AAT GTT AAA TAC ATT GCG TGG ATC CTT GAG AGT GCA CCC ATC TCT ATT        770
Asn Val Lys Tyr Ile Ala Trp Ile Leu Glu Ser Ala Pro Ile Ser Ile
            240                 245                 250

CTT GAG AAT CAT GAG CTG GCG AGC ATT GTG CTG GAT TAC AAA AGG GAG        818
Leu Glu Asn His Glu Leu Ala Ser Ile Val Leu Asp Tyr Lys Arg Glu
        255                 260                 265

TGT GGC CGG GAT AGT GTG CTG CAA TCA CAC ACC TCT GTG CAC ACG GAT        866
Cys Gly Arg Asp Ser Val Leu Gln Ser His Thr Ser Val His Thr Asp
270                 275                 280                 285

TGC AAC AGT GAG TCT GGA GAA ACA ACC TTG CAC TGT GAG CAT GTG CTG        914
Cys Asn Ser Glu Ser Gly Glu Thr Thr Leu His Cys Glu His Val Leu
            290                 295                 300

AGC CTT GAA TCA GGC CCG ACC ATG GTG AAG GCC CGG ACC ATG TGG AGG        962
Ser Leu Glu Ser Gly Pro Thr Met Val Lys Ala Arg Thr Met Trp Arg
        305                 310                 315

CCT AAG GGA ACC AAG GCC CAA GAA ACA GTG GTT CCA TCT TCA ATT           1007
Pro Lys Gly Thr Lys Ala Gln Glu Thr Val Val Pro Ser Ser Ile
            320                 325                 330

TGACTCGAGA CGTACGT                                                     1024
```

(2) INFORMATION FOR SEQ ID NO:13:

(i) SEQUENCE CHARACTERISTICS:
        (A) LENGTH: 332 amino acids
        (B) TYPE: amino acid
        (D) TOPOLOGY: linear (ii) MOLECULE TYPE: protein (xi) SEQUENCE DESCRIPTION: SEQ ID NO:13:

```
Met Gln Leu Pro Asp Trp Ser Met Leu Leu Ala Ala Ile Thr Thr Ile
 1               5                  10                  15

Phe Leu Ala Ala Glu Lys Gln Trp Thr Met Leu Asp Trp Lys Pro Arg
            20                  25                  30

Arg Pro Asp Met Leu Thr Asp Thr Phe Gly Phe Gly Arg Ile Ile His
        35                  40                  45

Asp Gly Leu Met Phe Arg Gln Asn Phe Ser Ile Arg Ser Tyr Glu Ile
     50                  55                  60

Gly Ala Asp Arg Thr Ala Ser Ile Glu Thr Leu Met Asn His Leu Gln
```

```
                 65                  70                  75                  80
Glu Thr Ala Leu Asn His Val Lys Thr Ala Gly Leu Gly Asp Gly
                     85                  90                  95
Phe Gly Ser Thr Pro Glu Met Ser Lys Arg Asn Leu Phe Trp Val Val
                100                 105                 110
Ser Gln Met Gln Ala Ile Ile Glu Arg Tyr Pro Cys Trp Gly Asp Thr
                115                 120                 125
Val Glu Val Asp Thr Trp Val Ser Ala Asn Gly Lys Asn Gly Met Arg
                130                 135                 140
Arg Asp Trp His Ile Arg Asp Pro Ile Thr Gly Leu Thr Ile Leu Lys
145                 150                 155                 160
Ala Thr Ser Lys Trp Val Met Met Asn Lys Leu Thr Arg Lys Leu Ala
                165                 170                 175
Arg Ile Pro Asp Glu Val Arg Thr Glu Ile Glu Pro Tyr Phe Phe Glu
                180                 185                 190
His Ser Ala Ile Val Asp Glu Asp Asn Arg Lys Leu Pro Lys Leu Pro
                195                 200                 205
Glu Gly Gln Ser Thr Ser Val Ala Lys Tyr Val Arg Thr Gly Leu Thr
                210                 215                 220
Pro Arg Trp Ala Asp Leu Asp Ile Asn Gln His Val Asn Asn Val Lys
225                 230                 235                 240
Tyr Ile Ala Trp Ile Leu Glu Ser Ala Pro Ile Ser Ile Leu Glu Asn
                245                 250                 255
His Glu Leu Ala Ser Ile Val Leu Asp Tyr Lys Arg Glu Cys Gly Arg
                260                 265                 270
Asp Ser Val Leu Gln Ser His Thr Ser Val His Thr Asp Cys Asn Ser
                275                 280                 285
Glu Ser Gly Glu Thr Thr Leu His Cys Glu His Val Leu Ser Leu Glu
                290                 295                 300
Ser Gly Pro Thr Met Val Lys Ala Arg Thr Met Trp Arg Pro Lys Gly
305                 310                 315                 320
Thr Lys Ala Gln Glu Thr Val Val Pro Ser Ser Ile
                325                 330

(2) INFORMATION FOR SEQ ID NO:14:

(i) SEQUENCE CHARACTERISTICS:
        (A) LENGTH:  39 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:14:

ACGTACGTGG CCAGAGAGGC CATGGCCGCC TCCATCGCG                         39

(2) INFORMATION FOR SEQ ID NO:15:

(i) SEQUENCE CHARACTERISTICS:
        (A) LENGTH:  42 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:15:

ACGTACGTGG CCATATTGGC CTCAAATTGA AGATGGAACC AC                     42
```

(2) INFORMATION FOR SEQ ID NO:16:

(i) SEQUENCE CHARACTERISTICS:
        (A) LENGTH: 1302 base pairs
        (B) TYPE: nucleic acid
        (C) STRANDEDNESS: single
        (D) TOPOLOGY: linear (ii) MOLECULE TYPE: DNA (iv) ANTI-SENSE: YES (xi) SEQUENCE DESCRIPTION: SEQ ID NO:16:

```
ACGTACGTGG CCATATTGGC CTCAAATTGA AGATGGAACC ACTGTTTCTT GGGCCTTGGT      60
TCCCTTAGGC CTCCACATGG TCCGGGCCTT CACCATGGTC GGGCCTGATT CAAGGCTCAG     120
CACATGCTCA CAGTGCAAGG TTGTTTCTCC AGACTCACTG TTGCAATCCG TGTGCACAGA     180
GGTGTGTGAT TGCAGCACAC TATCCCGGCC ACACTCCCTT TTGTAATCCA GCACAATGCT     240
CGCCAGCTCA TGATTCTCAA GAATAGAGAT GGGTGCACTC TCAAGGATCC ACGCAATGTA     300
TTTAACATTA TTGACATGCT GATTTATATC AAGATCAGCC CAGCGAGGAG TCAGGCCTGT     360
CCTCACATAT TTAGCTACAG AAGTGCTTTG TCCCTCTGGC AGTTTTGGAA GCTTGCGGTT     420
GTCTTCGTCA ACAATAGCAG AATGCTCAAA AAAGTATGGC TCTATTTCAG TCCGCACTTC     480
ATCTGGAATT CTTGCAAGCT TCCTAGTGAG TTTGTTCATC ATAACCCATT TACTTGTTGC     540
CTTCAGTATC GTGAGGCCTG TTATAGGATC ACGTATATGC AATCCCTAC GCATTCCATT      600
TTTACCATTA GCACTAACCC ATGTATCTAC TTCAACAGTA TCACCCCAGC ATGGATAACG     660
CTCGATGATG GCCTGCATTT GGCTAACCAC CCAGAACAAG TTTCGTTTAC TCATCTCTGG     720
TGTGGAGCCA AATCCATCAC CTAGCAGCCC AGCGGTCTTC ACATGATTGA GTGCCGTTTC     780
CTGCAAATGG TTCATCAGCG TCTCTATAGA TGCCGTCCTA TCTGCCCCAA TCTCGTAGGA     840
CCTAATGGAG AAGTTCTGCC TGAACATGAG CCCATCATGT ATGATCCGGC CAAACCCAAA     900
CGTGTCAGTG AGCATGTCAG GCCTCCTAGG CTTCCAGTCA AGCATCGTCC ACTGCTTCTC     960
TGCGGCCAAG AAGATGGTGG TGATGGCCGC AAGGAGCATG CTCCAGTCGG GAAGCTGGTT    1020
GTAGAAAGTC TTCGGCACCG AAGAAGGTAC GGTTTCGTGC TCCCCATCCG CCACCGCGGA    1080
CTTGCCCCCA CCGTTCATCT TGGGGACCGC AGCGTGGGCG CGCGTCTTGC CCGCCCTCAC    1140
GGCACTAGAC GACGAGGCTC CCGGCTTCGC CGCAACGCCG CGGACGTCCA GGCTCTCTGG    1200
GCGCTCCCCA AGGCCGTTCT TAGGAGCGGC CGGCGCCGGT GACCCTGGAA AGAAGGACGA    1260
GGCCGCGATG GAGGCGGCCA TGGCCTCTCT GGCCACGTAC GT                       1302
```

(2) INFORMATION FOR SEQ ID NO:17:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

```
ACGTACGTGG CCATATTGGC CAACCATGGC CGCCTCCATC GCG                       43
```

(2) INFORMATION FOR SEQ ID NO:18:

(i) SEQUENCE CHARACTERISTICS:

(A) LENGTH: 42 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:18:

AGCTAGCTGG CCAGAGAGGC CTCAAATTGA AGATGGAACC AC                               42

(2) INFORMATION FOR SEQ ID NO:19:

(i) SEQUENCE CHARACTERISTICS:
        (A) LENGTH: 1306 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 26..1282

(ix) FEATURE:
        (A) NAME/KEY: mat_peptide
        (B) LOCATION: 293..1282

(xi) SEQUENCE DESCRIPTION: SEQ ID NO:19:

```
ACGTACGTGG CCATATTGGC CAACC ATG GCC GCC TCC ATC GCG GCC TCG TCC              52
                           Met Ala Ala Ser Ile Ala Ala Ser Ser
                           -89                 -85

TTC TTT CCA GGG TCA CCG GCG CCG GCC GCT CCT AAG AAC GGC CTT GGG             100
Phe Phe Pro Gly Ser Pro Ala Pro Ala Ala Pro Lys Asn Gly Leu Gly
-80             -75                 -70                  -65

GAG CGC CCA GAG AGC CTG GAC GTC CGC GGC GTT GCG GCG AAG CCG GGA             148
Glu Arg Pro Glu Ser Leu Asp Val Arg Gly Val Ala Ala Lys Pro Gly
            -60                 -55                 -50

GCC TCG TCG TCT AGT GCC GTG AGG GCG GGC AAG ACG CGC GCC CAC GCT             196
Ala Ser Ser Ser Ser Ala Val Arg Ala Gly Lys Thr Arg Ala His Ala
        -45                 -40                 -35

GCG GTC CCC AAG ATG AAC GGT GGG GGC AAG TCC GCG GTG GCG GAT GGG             244
Ala Val Pro Lys Met Asn Gly Gly Gly Lys Ser Ala Val Ala Asp Gly
        -30                 -25                 -20

GAG CAC GAA ACC GTA CCT TCT TCG GTG CCG AAG ACT TTC TAC AAC CAG             292
Glu His Glu Thr Val Pro Ser Ser Val Pro Lys Thr Phe Tyr Asn Gln
    -15                 -10                  -5

CTT CCC GAC TGG AGC ATG CTC CTT GCG GCC ATC ACC ACC ATC TTC TTG             340
Leu Pro Asp Trp Ser Met Leu Leu Ala Ala Ile Thr Thr Ile Phe Leu
 1               5                  10                  15

GCC GCA GAG AAG CAG TGG ACG ATG CTT GAC TGG AAG CCT AGG AGG CCT             388
Ala Ala Glu Lys Gln Trp Thr Met Leu Asp Trp Lys Pro Arg Arg Pro
            20                  25                  30

GAC ATG CTC ACT GAC ACG TTT GGG TTT GGC CGG ATC ATA CAT GAT GGG             436
Asp Met Leu Thr Asp Thr Phe Gly Phe Gly Arg Ile Ile His Asp Gly
            35                  40                  45

CTC ATG TTC AGG CAG AAC TTC TCC ATT AGG TCC TAC GAG ATT GGG GCA             484
Leu Met Phe Arg Gln Asn Phe Ser Ile Arg Ser Tyr Glu Ile Gly Ala
        50                  55                  60

GAT AGG ACG GCA TCT ATA GAG ACG CTG ATG AAC CAT TTG CAG GAA ACG             532
Asp Arg Thr Ala Ser Ile Glu Thr Leu Met Asn His Leu Gln Glu Thr
 65                 70                  75                  80

GCA CTC AAT CAT GTG AAG ACC GCT GGG CTG CTA GGT GAT GGA TTT GGC             580
Ala Leu Asn His Val Lys Thr Ala Gly Leu Leu Gly Asp Gly Phe Gly
                85                  90                  95
```

```
TCC ACA CCA GAG ATG AGT AAA CGA AAC TTG TTC TGG GTG GTT AGC CAA        628
Ser Thr Pro Glu Met Ser Lys Arg Asn Leu Phe Trp Val Val Ser Gln
            100                 105                 110

ATG CAG GCC ATC ATC GAG CGT TAT CCA TGC TGG GGT GAT ACT GTT GAA        676
Met Gln Ala Ile Ile Glu Arg Tyr Pro Cys Trp Gly Asp Thr Val Glu
            115                 120                 125

GTA GAT ACA TGG GTT AGT GCT AAT GGT AAA AAT GGA ATG CGT AGG GAT        724
Val Asp Thr Trp Val Ser Ala Asn Gly Lys Asn Gly Met Arg Arg Asp
        130                 135                 140

TGG CAT ATA CGT GAT CCT ATA ACA GGC CTC ACG ATA CTG AAG GCA ACA        772
Trp His Ile Arg Asp Pro Ile Thr Gly Leu Thr Ile Leu Lys Ala Thr
145                 150                 155                 160

AGT AAA TGG GTT ATG ATG AAC AAA CTC ACT AGG AAG CTT GCA AGA ATT        820
Ser Lys Trp Val Met Met Asn Lys Leu Thr Arg Lys Leu Ala Arg Ile
                165                 170                 175

CCA GAT GAA GTG CGG ACT GAA ATA GAG CCA TAC TTT TTT GAG CAT TCT        868
Pro Asp Glu Val Arg Thr Glu Ile Glu Pro Tyr Phe Phe Glu His Ser
            180                 185                 190

GCT ATT GTT GAC GAA GAC AAC CGC AAG CTT CCA AAA CTG CCA GAG GGA        916
Ala Ile Val Asp Glu Asp Asn Arg Lys Leu Pro Lys Leu Pro Glu Gly
            195                 200                 205

CAA AGC ACT TCT GTA GCT AAA TAT GTG AGG ACA GGC CTG ACT CCT CGC        964
Gln Ser Thr Ser Val Ala Lys Tyr Val Arg Thr Gly Leu Thr Pro Arg
        210                 215                 220

TGG GCT GAT CTT GAT ATA AAT CAG CAT GTC AAT AAT GTT AAA TAC ATT       1012
Trp Ala Asp Leu Asp Ile Asn Gln His Val Asn Asn Val Lys Tyr Ile
225                 230                 235                 240

GCG TGG ATC CTT GAG AGT GCA CCC ATC TCT ATT CTT GAG AAT CAT GAG       1060
Ala Trp Ile Leu Glu Ser Ala Pro Ile Ser Ile Leu Glu Asn His Glu
                245                 250                 255

CTG GCG AGC ATT GTG CTG GAT TAC AAA AGG GAG TGT GGC CGG GAT AGT       1108
Leu Ala Ser Ile Val Leu Asp Tyr Lys Arg Glu Cys Gly Arg Asp Ser
            260                 265                 270

GTG CTG CAA TCA CAC ACC TCT GTG CAC ACG GAT TGC AAC AGT GAG TCT       1156
Val Leu Gln Ser His Thr Ser Val His Thr Asp Cys Asn Ser Glu Ser
            275                 280                 285

GGA GAA ACA ACC TTG CAC TGT GAG CAT GTG CTG AGC CTT GAA TCA GGC       1204
Gly Glu Thr Thr Leu His Cys Glu His Val Leu Ser Leu Glu Ser Gly
        290                 295                 300

CCG ACC ATG GTG AAG GCC CGG ACC ATG TGG AGG CCT AAG GGA ACC AAG       1252
Pro Thr Met Val Lys Ala Arg Thr Met Trp Arg Pro Lys Gly Thr Lys
305                 310                 315                 320

GCC CAA GAA ACA GTG GTT CCA TCT TCA ATT TGAGGCCTCT CTGGCCAGCT         1302
Ala Gln Glu Thr Val Val Pro Ser Ser Ile
                325                 330

AGCT                                                                  1306
```

(2) INFORMATION FOR SEQ ID NO:20:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

TTTTCTAGAA AGCTTGCCGA GTGCCATCCT TGGACACTC                              39

(2) INFORMATION FOR SEQ ID NO:21:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

```
TTTCCATGGT GTAGTGTCAC TGTGATATGC TCGGGTGTG                    39
```

(2) INFORMATION FOR SEQ ID NO:22:

(i) SEQUENCE CHARACTERISTICS:
        (A) LENGTH: 1267 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

```
TTTTCTAGAA AGCTTGCCGA GTGCCATCCT TGGACACTCG ATAAAGTATA TTTTATTTTT    60
TTTATTTTGC CAACCAAACT TTTTGTGGTA TGTTCCTACA CTATGTAGAT CTACATGTAC   120
CATTTTGGCA CAATTACAAA AATGTTTTCT ATAACTATTA GATTTAGTTC GTTTATTTGA   180
ATTTCTTCGG AAAATTCACA TATGAACTGC AAGTCACTCG AAACATGAAA AACCGTGCAT   240
GCAAAATAAA TGATATGCAT GTTATCTAGC ACAAGTTACG ACCGATTTCA GAAGCAGACC   300
AGAATCTTCA AGCACCATGC TCACTAAACA TGACCGTGAA CTTGTTATCC AGTTGTTTAA   360
AAATTGTATA AAACACAAAT AAAGTCAGAA ATTAATGAAA CTTGTCCACA TGTCATGATA   420
TCATATATAG AGGTTGTGAT AAAAATTTGA TATTGTTTCG GTAAAGTTGT GACGTACTAT   480
GTGTAGAAAC CTAAGTGACC TACACATAAA ATCATAGAGT TTCAATGTAG TTCACTCGAC   540
AAAGACTTTG TCAAGTGTCC GATAAAAAGT ATTCAGCAAA GAAGCCGTTG TCGATTTACT   600
GTTCGTCGAG ATCTCTTTGC CGAGTGTCAC ACTAGGCAAA GTCTTTACGG AGTGTTTTTC   660
AGGCTTTGAC ACTCGGCAAA GCGCTCGATT CCAGTAGTGA CAGTAATTTG CATCAAAAAT   720
AGCCGAGAGA TTTAAAATGA GTCAACTAAT AGACCAACTA ATTATTAGCT ATTAGTCGTT   780
AGCTTCTTTA ATCTAAGCTA AAACCAACTA ATAGCTTATT TGTTGAATTA CAATTAGCTC   840
AACGGAATTC TCTGTTTTTT CTATAAAAAA GGGAAACTGC CCCTCATTTA CAGCAAACTG   900
TCCGCTGCCT GTCGTCCAGA TACAATGAAC GTACCTAGTA GGAACTCTTT TACACGCTCG   960
GTCGCTCGCC GCGGATCGGA GTCCCAGGAA CACGACACCA CTGTGGAACA CGACAAAGTC  1020
TGCTCAGAGG CGGCCACACC CTGGCGTGCA CCGAGCCGGA GCCCGGATAA GCACGGTAAG  1080
GAGAGTACGG CGGGACGTGG CGACCCGTGT GTCTGCTGCC ACGCAGCCTT CCTCCACGTA  1140
GCCGCGCGGC CGCGCCACGT ACCAGGGCCC GGCGCTGGTA TAAATGCGCG CCACCTCCGC  1200
TTTAGTTCTG CATACAGCCA ACCCAACACA CACCCGAGCA TATCACAGTG ACACTACACC  1260
ATGGAAA                                                            1267
```

(2) INFORMATION FOR SEQ ID NO:23:

(i) SEQUENCE CHARACTERISTICS:
        (A) LENGTH: 1456 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

| | | | | | |
|---|---|---|---|---|---|
| TTTTCTAGAA | AGCTTGCCGA | GTGCCATCCT | TGGACACTCG | ATAAAGTATA | TTTTATTTTT | 60 |
| TTTATTTTGC | CAACCAAACT | TTTTGTGGTA | TGTTCCTACA | CTATGTAGAT | CTACATGTAC | 120 |
| CATTTTGGCA | CAATTACATA | TTTACAAAAA | TGTTTTCTAT | AAATATTAGA | TTTAGTTCGT | 180 |
| TTATTTGAAT | TTCTTCGGAA | AATTCACATT | TAAACTGCAA | GTCACTCGAA | ACATGGAAAA | 240 |
| CCGTGCATGC | AAAATAAATG | ATATGCATGT | TATCTAGCAC | AAGTTACGAC | CGATTTCAGA | 300 |
| AGCAGACCAG | AATCTTCAAG | CACCATGCTC | ACTAAACATG | ACCGTGAACT | TGTTATCTAG | 360 |
| TTGTTTAAAA | ATTGTATAAA | ACACAAATAA | AGTCAGAAAT | TAATGAAACT | TGTCCACATG | 420 |
| TCATGATATC | ATATATAGAG | GTTGTGATAA | AAATTTGATA | ATGTTTCGGT | AAAGTTGTGA | 480 |
| CGTACTATGT | GTAGAAACCT | AAGTGACCTA | CACATAAAAT | CATAGAGTTT | CAATGTAGTT | 540 |
| CACTCGACAA | AGACTTTGTC | AAGTGTCCGA | TAAAAGTAC  | TCGACAAAGA | AGCCGTTGTC | 600 |
| GATGTACTGT | TCGTCGAGAT | CTCTTTGTCG | AGTGTCACAC | TAGGCAAAGT | CTTTACGGAG | 660 |
| TGTTTTTCAG | GCTTTGACAC | TCGGCAAAGC | GCTCGATTCC | AGTAGTGACA | GTAATTTGCA | 720 |
| TCAAAAATAG | CTGAGAGATT | TAGGCCCCGT | TTCAATCTCA | CGGGATAAAG | TTTAGCTTCC | 780 |
| TGCTAAACTT | TAGCTATATG | AATTGAAGTG | CTAAAGTTTA | GTTTCAATTA | CCACCATTAG | 840 |
| CTCTCCTGTT | TAGATTACAA | ATGGCTAAAA | GTAGCTAAAA | AATAGCTGCT | AAAGTTTATC | 900 |
| TCGCGAGATT | GAAACAGGGC | CTTAAAATGA | GTCAACTAAT | AGACCAACTA | ATTATTAGCT | 960 |
| ATTAGTCGTT | AGCTTCTTTA | ATCTAAGCTA | AAACCAACTA | ATAGCTTATT | TGTTGAATTA | 1020 |
| CAATTAGCTC | AACGGAATTC | TCTGTTTTTT | CTATAAAAAA | AGGGAAACTG | CCCCTCATTT | 1080 |
| ACAGCAAATT | GTCCGCTGCC | TGTCGTCCAG | ATACAATGAA | CGTACCTAGT | AGGAACTCTT | 1140 |
| TTACACGCTC | GGTCGCTCGC | CGCGGATCGG | AGTCCCAGGA | ACACGACACC | ACTGTGTAAC | 1200 |
| ACGACAAAGT | CTGCTCAGAG | GCGGCCACAC | CCTGGCGTGC | ACCGAGCCGG | AGCCCGGATA | 1260 |
| AGCACGGTAA | GGAGAGTACG | GCGGGACGTG | GCGACCCGTG | TGTCTGCTGC | CACGCAGCCT | 1320 |
| TCCTCCACGT | AGCCGCGCGG | CCGCGCCACG | TACCAGGGCC | CGGCGCTGGT | ATAAATGCGC | 1380 |
| GCTACCTCCG | CTTTAGTTCT | GCATACAGTC | AACCTAACAC | ACCCGAGCAT | ATCACAGTGA | 1440 |
| CACTACACCA | TGGAAA     |            |            |            |            | 1456 |

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

CCATGGCCGC CTCCATCGC                                                19

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

CAGGCCCGAC GATGGTGAAG G                                                    21

(2) INFORMATION FOR SEQ ID NO:26:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:26:

CCTTCACCAT CGTCGGGCCT G                                                    21

(2) INFORMATION FOR SEQ ID NO:27:

(i) SEQUENCE CHARACTERISTICS:
            (A) LENGTH: 1197 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: CDS
            (B) LOCATION: 3..1196

(ix) FEATURE:
            (A) NAME/KEY: mat_peptide
            (B) LOCATION: 270..1196

(xi) SEQUENCE DESCRIPTION: SEQ ID NO:27:

```
CC ATG GCC GCC TCC ATC GCG GCC TCG TCC TTC TTT CCA GGG TCA CCG              47
   Met Ala Ala Ser Ile Ala Ala Ser Ser Phe Phe Pro Gly Ser Pro
   -89             -85                 -80                 -75

GCG CCG GCC GCT CCT AAG AAC GGC CTT GGG GAG CGC CCA GAG AGC CTG             95
Ala Pro Ala Ala Pro Lys Asn Gly Leu Gly Glu Arg Pro Glu Ser Leu
                -70                 -65                 -60

GAC GTC CGC GGC GTT GCG GCG AAG CCG GGA GCC TCG TCG TCT AGT GCC            143
Asp Val Arg Gly Val Ala Ala Lys Pro Gly Ala Ser Ser Ser Ser Ala
            -55                 -50                 -45

GTG AGG GCG GGC AAG ACG CGC GCC CAC GCT GCG GTC CCC AAG ATG AAC            191
Val Arg Ala Gly Lys Thr Arg Ala His Ala Ala Val Pro Lys Met Asn
        -40                 -35                 -30

GGT GGG GGC AAG TCC GCG GTG GCG GAT GGG GAG CAC GAA ACC GTA CCT            239
Gly Gly Gly Lys Ser Ala Val Ala Asp Gly Glu His Glu Thr Val Pro
    -25                 -20                 -15

TCT TCG GTG CCG AAG ACT TTC TAC AAC CAG CTT CCC GAC TGG AGC ATG            287
Ser Ser Val Pro Lys Thr Phe Tyr Asn Gln Leu Pro Asp Trp Ser Met
-10                 -5                   1                   5

CTC CTT GCG GCC ATC ACC ACC ATC TTC TTG GCC GCA GAG AAG CAG TGG            335
Leu Leu Ala Ala Ile Thr Thr Ile Phe Leu Ala Ala Glu Lys Gln Trp
                 10                  15                  20

ACG ATG CTT GAC TGG AAG CCT AGG AGG CCT GAC ATG CTC ACT GAC ACG            383
Thr Met Leu Asp Trp Lys Pro Arg Arg Pro Asp Met Leu Thr Asp Thr
             25                  30                  35

TTT GGG TTT GGC CGG ATC ATA CAT GAT GGG CTC ATG TTC AGG CAG AAC            431
Phe Gly Phe Gly Arg Ile Ile His Asp Gly Leu Met Phe Arg Gln Asn
         40                  45                  50

TTC TCC ATT AGG TCC TAC GAG ATT GGG GCA GAT AGG ACG GCA TCT ATA            479
```

```
Phe Ser Ile Arg Ser Tyr Glu Ile Gly Ala Asp Arg Thr Ala Ser Ile
 55                  60                  65                  70

GAG ACG CTG ATG AAC CAT TTG CAG GAA ACG GCA CTC AAT CAT GTG AAG         527
Glu Thr Leu Met Asn His Leu Gln Glu Thr Ala Leu Asn His Val Lys
             75                  80                  85

ACC GCT GGG CTG CTA GGT GAT GGA TTT GGC TCC ACA CCA GAG ATG AGT         575
Thr Ala Gly Leu Leu Gly Asp Gly Phe Gly Ser Thr Pro Glu Met Ser
                 90                  95                 100

AAA CGA AAC TTG TTC TGG GTG GTT AGC CAA ATG CAG GCC ATC ATC GAG         623
Lys Arg Asn Leu Phe Trp Val Val Ser Gln Met Gln Ala Ile Ile Glu
            105                 110                 115

CGT TAT CCA TGC TGG GGT GAT ACT GTT GAA GTA GAT ACA TGG GTT AGT         671
Arg Tyr Pro Cys Trp Gly Asp Thr Val Glu Val Asp Thr Trp Val Ser
120                 125                 130

GCT AAT GGT AAA AAT GGA ATG CGT AGG GAT TGG CAT ATA CGT GAT CCT         719
Ala Asn Gly Lys Asn Gly Met Arg Arg Asp Trp His Ile Arg Asp Pro
135                 140                 145                 150

ATA ACA GGC CTC ACG ATA CTG AAG GCA ACA AGT AAA TGG GTT ATG ATG         767
Ile Thr Gly Leu Thr Ile Leu Lys Ala Thr Ser Lys Trp Val Met Met
                155                 160                 165

AAC AAA CTC ACT AGG AAG CTT GCA AGA ATT CCA GAT GAA GTG CGG ACT         815
Asn Lys Leu Thr Arg Lys Leu Ala Arg Ile Pro Asp Glu Val Arg Thr
            170                 175                 180

GAA ATA GAG CCA TAC TTT TTT GAG CAT TCT GCT ATT GTT GAC GAA GAC         863
Glu Ile Glu Pro Tyr Phe Phe Glu His Ser Ala Ile Val Asp Glu Asp
            185                 190                 195

AAC CGC AAG CTT CCA AAA CTG CCA GAG GGA CAA AGC ACT TCT GTA GCT         911
Asn Arg Lys Leu Pro Lys Leu Pro Glu Gly Gln Ser Thr Ser Val Ala
200                 205                 210

AAA TAT GTG AGG ACA GGC CTG ACT CCT CGC TGG GCT GAT CTT GAT ATA         959
Lys Tyr Val Arg Thr Gly Leu Thr Pro Arg Trp Ala Asp Leu Asp Ile
215                 220                 225                 230

AAT CAG CAT GTC AAT AAT GTT AAA TAC ATT GCG TGG ATC CTT GAG AGT        1007
Asn Gln His Val Asn Asn Val Lys Tyr Ile Ala Trp Ile Leu Glu Ser
                235                 240                 245

GCA CCC ATC TCT ATT CTT GAG AAT CAT GAG CTG GCG AGC ATT GTG CTG        1055
Ala Pro Ile Ser Ile Leu Glu Asn His Glu Leu Ala Ser Ile Val Leu
            250                 255                 260

GAT TAC AAA AGG GAG TGT GGC CGG GAT AGT GTG CTG CAA TCA CAC ACC        1103
Asp Tyr Lys Arg Glu Cys Gly Arg Asp Ser Val Leu Gln Ser His Thr
            265                 270                 275

TCT GTG CAC ACG GAT TGC AAC AGT GAG TCT GGA GAA ACA ACC TTG CAC        1151
Ser Val His Thr Asp Cys Asn Ser Glu Ser Gly Glu Thr Thr Leu His
280                 285                 290

TGT GAG CAT GTG CTG AGC CTT GAA TCA GGC CCG ACG ATG GTG AAG            1196
Cys Glu His Val Leu Ser Leu Glu Ser Gly Pro Thr Met Val Lys
295                 300                 305

G                                                                      1197
```

(2) INFORMATION FOR SEQ ID NO:28:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 3..83

(xi) SEQUENCE DESCRIPTION: SEQ ID NO:28:

```
CA GGC CCG ACG ATG GTG AAG GCC CGG ACC ATG TGG AGG CCT AAG GGA        47
   Gly Pro Thr Met Val Lys Ala Arg Thr Met Trp Arg Pro Lys Gly
   310             315             320

ACC AAG GCC CAA GAA ACA GTG GTT CCA TCT TCA ATT TGACTCGAGA            93
Thr Lys Ala Gln Glu Thr Val Val Pro Ser Ser Ile
325             330             335

CGTACGT                                                               100
```

(2) INFORMATION FOR SEQ ID NO:29:

(i) SEQUENCE CHARACTERISTICS:
        (A) LENGTH: 1276 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 3..1259

(ix) FEATURE:
        (A) NAME/KEY: mat_peptide
        (B) LOCATION: 270..1259

(xi) SEQUENCE DESCRIPTION: SEQ ID NO:29:

```
CC ATG GCC GCC TCC ATC GCG GCC TCG TCC TTC TTT CCA GGG TCA CCG        47
   Met Ala Ala Ser Ile Ala Ala Ser Ser Phe Phe Pro Gly Ser Pro
   -89             -85             -80             -75

GCG CCG GCC GCT CCT AAG AAC GGC CTT GGG GAG CGC CCA GAG AGC CTG       95
Ala Pro Ala Ala Pro Lys Asn Gly Leu Gly Glu Arg Pro Glu Ser Leu
                -70             -65             -60

GAC GTC CGC GGC GTT GCG GCG AAG CCG GGA GCC TCG TCG TCT AGT GCC       143
Asp Val Arg Gly Val Ala Ala Lys Pro Gly Ala Ser Ser Ser Ser Ala
            -55             -50             -45

GTG AGG GCG GGC AAG ACG CGC GCC CAC GCT GCG GTC CCC AAG ATG AAC       191
Val Arg Ala Gly Lys Thr Arg Ala His Ala Ala Val Pro Lys Met Asn
        -40             -35             -30

GGT GGG GGC AAG TCC GCG GTG GCG GAT GGG GAG CAC GAA ACC GTA CCT       239
Gly Gly Gly Lys Ser Ala Val Ala Asp Gly Glu His Glu Thr Val Pro
    -25             -20             -15

TCT TCG GTG CCG AAG ACT TTC TAC AAC CAG CTT CCC GAC TGG AGC ATG       287
Ser Ser Val Pro Lys Thr Phe Tyr Asn Gln Leu Pro Asp Trp Ser Met
-10             -5              1               5

CTC CTT GCG GCC ATC ACC ACC ATC TTT TTG GCC GCA GAG AAG CAG TGG       335
Leu Leu Ala Ala Ile Thr Thr Ile Phe Leu Ala Ala Glu Lys Gln Trp
            10              15              20

ACG ATG CTT GAC TGG AAG CCT AGG AGG CCT GAC ATG CTC ACT GAC ACG       383
Thr Met Leu Asp Trp Lys Pro Arg Arg Pro Asp Met Leu Thr Asp Thr
        25              30              35

TTT GGG TTT GGC CGG ATC ATA CAT GAT GGG CTC ATG TTC AGG CAG AAC       431
Phe Gly Phe Gly Arg Ile Ile His Asp Gly Leu Met Phe Arg Gln Asn
    40              45              50

TTC TCC ATT AGG TCC TAC GAG ATT GGG GCA GAT AGG ACG GCA TCT ATA       479
Phe Ser Ile Arg Ser Tyr Glu Ile Gly Ala Asp Arg Thr Ala Ser Ile
55              60              65              70

GAG ACG CTG ATG AAC CAT TTG CAG GAA ACG GCA CTC AAT CAT GTG AAG       527
Glu Thr Leu Met Asn His Leu Gln Glu Thr Ala Leu Asn His Val Lys
            75              80              85

ACC GCT GGG CTG CTA GGT GAT GGA TTT GGC TCC ACA CCA GAG ATG AGT       575
```

```
Thr Ala Gly Leu Leu Gly Asp Gly Phe Gly Ser Thr Pro Glu Met Ser
            90                  95                 100

AAA CGA AAC TTG TTC TGG GTG GTT AGC CAA ATG CAG GCC ATC ATC GAG      623
Lys Arg Asn Leu Phe Trp Val Val Ser Gln Met Gln Ala Ile Ile Glu
            105                 110                115

CGT TAT CCA TGC TGG GGT GAT ACT GTT GAA GTA GAT ACA TGG GTT AGT      671
Arg Tyr Pro Cys Trp Gly Asp Thr Val Glu Val Asp Thr Trp Val Ser
    120                 125                 130

GCT AAT GGT AAA AAT GGA ATG CGT AGG GAT TGG CAT ATA CGT GAT CCT      719
Ala Asn Gly Lys Asn Gly Met Arg Arg Asp Trp His Ile Arg Asp Pro
135                 140                 145                 150

ATA ACA GGC CTC ACG ATA CTG AAG GCA ACA AGT AAA TGG GTT ATG ATG      767
Ile Thr Gly Leu Thr Ile Leu Lys Ala Thr Ser Lys Trp Val Met Met
                155                 160                 165

AAC AAA CTC ACT AGG AAG CTT GCA AGA ATT CCA GAT GAA GTG CGG ACT      815
Asn Lys Leu Thr Arg Lys Leu Ala Arg Ile Pro Asp Glu Val Arg Thr
            170                 175                 180

GAA ATA GAG CCA TAC TTT TTT GAG CAT TCT GCT ATT GTT GAC GAA GAC      863
Glu Ile Glu Pro Tyr Phe Phe Glu His Ser Ala Ile Val Asp Glu Asp
                185                 190                 195

AAC CGC AAG CTT CCA AAA CTG CCA GAG GGA CAA AGC ACT TCT GTA GCT      911
Asn Arg Lys Leu Pro Lys Leu Pro Glu Gly Gln Ser Thr Ser Val Ala
    200                 205                 210

AAA TAT GTG AGG ACA GGC CTG ACT CCT CGC TGG GCT GAT CTT GAT ATA      959
Lys Tyr Val Arg Thr Gly Leu Thr Pro Arg Trp Ala Asp Leu Asp Ile
215                 220                 225                 230

AAT CAG CAT GTC AAT AAT GTT AAA TAC ATT GCG TGG ATC CTT GAG AGT     1007
Asn Gln His Val Asn Asn Val Lys Tyr Ile Ala Trp Ile Leu Glu Ser
                235                 240                 245

GCA CCC ATC TCT ATT CTT GAG AAT CAT GAG CTG GCG AGC ATT GTG CTG     1055
Ala Pro Ile Ser Ile Leu Glu Asn His Glu Leu Ala Ser Ile Val Leu
            250                 255                 260

GAT TAC AAA AGG GAG TGT GGC CGG GAT AGT GTG CTG CAA TCA CAC ACC     1103
Asp Tyr Lys Arg Glu Cys Gly Arg Asp Ser Val Leu Gln Ser His Thr
                265                 270                 275

TCT GTG CAC ACG GAT TGC AAC AGT GAG TCT GGA GAA ACA ACC TTG CAC     1151
Ser Val His Thr Asp Cys Asn Ser Glu Ser Gly Glu Thr Thr Leu His
            280                 285                 290

TGT GAG CAT GTG CTG AGC CTT GAA TCA GGC CCG ACG ATG GTG AAG GCC     1199
Cys Glu His Val Leu Ser Leu Glu Ser Gly Pro Thr Met Val Lys Ala
295                 300                 305                 310

CGG ACC ATG TGG AGG CCT AAG GGA ACC AAG GCC CAA GAA ACA GTG GTT     1247
Arg Thr Met Trp Arg Pro Lys Gly Thr Lys Ala Gln Glu Thr Val Val
                315                 320                 325

CCA TCT TCA ATT TGACTCGAGA CGTACGT                                   1276
Pro Ser Ser Ile
            330

(2) INFORMATION FOR SEQ ID NO:30:

(i) SEQUENCE CHARACTERISTICS:
        (A) LENGTH:  34 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:30:

TTTTGGTACC GCCGAGTGCC ATCCTTGGAC ACTC                                   34
```

(2) INFORMATION FOR SEQ ID NO:31:

(i) SEQUENCE CHARACTERISTICS:
        (A) LENGTH: 1262 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

```
TTTTGGTACC GCCGAGTGCC ATCCTTGGAC ACTCGATAAA GTATATTTTA         50
TTTTTTTTAT TTTGCCAACC AAACTTTTTG TGGTATGTTC CTACACTATG        100
TAGATCTACA TGTACCATTT TGGCACAATT ACAAAAATGT TTTCTATAAC        150
TATTAGATTT AGTTCGTTTA TTTGAATTTC TTCGGAAAAT TCACATATGA        200
ACTGCAAGTC ACTCGAAACA TGAAAAACCG TGCATGCAAA ATAAATGATA        250
TGCATGTTAT CTAGCACAAG TTACGACCGA TTTCAGAAGC AGACCAGAAT        300
CTTCAAGCAC CATGCTCACT AAACATGACC GTGAACTTGT TATCCAGTTG        350
TTTAAAAATT GTATAAAACA CAAATAAAGT CAGAAATTAA TGAAACTTGT        400
CCACATGTCA TGATATCATA TATAGAGGTT GTGATAAAAA TTTGATATTG        450
TTTCGGTAAA GTTGTGACGT ACTATGTGTA GAAACCTAAG TGACCTACAC        500
ATAAAATCAT AGAGTTTCAA TGTAGTTCAC TCGACAAAGA CTTTGTCAAG        550
TGTCCGATAA AAAGTATTCA GCAAAGAAGC CGTTGTCGAT TTACTGTTCG        600
TCGAGATCTC TTTGCCGAGT GTCACACTAG GCAAAGTCTT TACGGAGTGT        650
TTTTCAGGCT TTGACACTCG GCAAAGCGCT CGATTCCAGT AGTGACAGTA        700
ATTTGCATCA AAAATAGCCG AGAGATTTAA AATGAGTCAA CTAATAGACC        750
AACTAATTAT TAGCTATTAG TCGTTAGCTT CTTTAATCTA AGCTAAAACC        800
AACTAATAGC TTATTTGTTG AATTACAATT AGCTCAACGG AATTCTCTGT        850
TTTTTCTATA AAAAAGGGAA ACTGCCCCTC ATTTACAGCA AACTGTCCGC        900
TGCCTGTCGT CCAGATACAA TGAACGTACC TAGTAGGAAC TCTTTTACAC        950
GCTCGGTCGC TCGCCGCGGA TCGGAGTCCC AGGAACACGA CACCACTGTG       1000
GAACACGACA AAGTCTGCTC AGAGGCGGCC ACACCCTGGC GTGCACCGAG       1050
CCGGAGCCCG GATAAGCACG GTAAGGAGAG TACGGCGGGA CGTGGCGACC       1100
CGTGTGTCTG CTGCCACGCA GCCTTCCTCC ACGTAGCCGC GCGGCCGCGC       1150
CACGTACCAG GGCCCGGCGC TGGTATAAAT GCGCGCCACC TCCGCTTTAG       1200
TTCTGCATAC AGCCAACCCA ACACACACCC GAGCATATCA CAGTGACACT       1250
ACACCATGGA AA                                               1262
```

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

```
TAYGARGTNG GNATHAAYAA                                          20
```

(2) INFORMATION FOR SEQ ID NO:33:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..324

(xi) SEQUENCE DESCRIPTION: SEQ ID NO:33:

```
TAC GAG GTG GGG ATC AAC AAG ACG GCC ACC GTT GAG ACC ATC GCC AAT        48
Tyr Glu Val Gly Ile Asn Lys Thr Ala Thr Val Glu Thr Ile Ala Asn
                335                 340                 345

CTC CTC CAG GAG GTA GGA TGT AAC CAT GCA CAA AGT GTT GGG TTC TCC        96
Leu Leu Gln Glu Val Gly Cys Asn His Ala Gln Ser Val Gly Phe Ser
        350                 355                 360

ACT GAT GGC TTC GCC ACG ACC ACT ACA ATG AGA AAA CTT GGT CTT ATT       144
Thr Asp Gly Phe Ala Thr Thr Thr Thr Met Arg Lys Leu Gly Leu Ile
    365                 370                 375

TGG GTG ACG AAC AGA ATG CAC ATT GAG ATC TAC AAG TAC CCA GCT TGG       192
Trp Val Thr Asn Arg Met His Ile Glu Ile Tyr Lys Tyr Pro Ala Trp
380                 385                 390

GGT GAT GTT GTT GAG ATC GAA ACA TGG TGC CAA GAA GAT GGA AGA ATT       240
Gly Asp Val Val Glu Ile Glu Thr Trp Cys Gln Glu Asp Gly Arg Ile
395                 400                 405                 410

GGT ACC CGT CGT GAT TGG ATC CTC AAG GAC CTA GCT AAT GGT GAA GTT       288
Gly Thr Arg Arg Asp Trp Ile Leu Lys Asp Leu Ala Asn Gly Glu Val
                415                 420                 425

ATT GGC AGA GCT ACC AGC AAG TGG GTC ATG ATG AAC                       324
Ile Gly Arg Ala Thr Ser Lys Trp Val Met Met Asn
                430                 435
```

(2) INFORMATION FOR SEQ ID NO:34:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO:34:

```
Tyr Glu Val Gly Ile Asn Lys Thr Ala Thr Val Glu Thr Ile Ala Asn
  1               5                  10                  15

Leu Leu Gln Glu Val Gly Cys Asn His Ala Gln Ser Val Gly Phe Ser
             20                  25                  30

Thr Asp Gly Phe Ala Thr Thr Thr Thr Met Arg Lys Leu Gly Leu Ile
         35                  40                  45

Trp Val Thr Asn Arg Met His Ile Glu Ile Tyr Lys Tyr Pro Ala Trp
     50                  55                  60

Gly Asp Val Val Glu Ile Glu Thr Trp Cys Gln Glu Asp Gly Arg Ile
 65                  70                  75                  80

Gly Thr Arg Arg Asp Trp Ile Leu Lys Asp Leu Ala Asn Gly Glu Val
                 85                  90                  95

Ile Gly Arg Ala Thr Ser Lys Trp Val Met Met Asn
            100                 105
```

-continued (2) INFORMATION FOR SEQ ID NO:35:

(i) SEQUENCE CHARACTERISTICS:
        (A) LENGTH: 1287 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 38..1135

(ix) FEATURE:
        (A) NAME/KEY: mat_peptide
        (B) LOCATION: 140..1135

(xi) SEQUENCE DESCRIPTION: SEQ ID NO:35:

```
AGCCACGAGC CTTCTCGAAC CGACGCATCC GCCACCC ATG CTG CGC TGC CAC ACG        55
                                        Met Leu Arg Cys His Thr
                                        -34             -30

CCA CCG CAA TGC GCC CGC GCG CCG CTC CGC CAC CAC GGA AGG TGG GAG        103
Pro Pro Gln Cys Ala Arg Ala Pro Leu Arg His His Gly Arg Trp Glu
        -25             -20             -15

TCG CCT CCG GCG GCG GCG CCC GCG GTG GTA GTG CGG TGC GCG CGG GGT        151
Ser Pro Pro Ala Ala Ala Pro Ala Val Val Val Arg Cys Ala Arg Gly
    -10             -5                  1

GCG CCG CAG GTG TCC GGG ATC GAG GCG GCT TCG CCG GGC CAC GCG GCT        199
Ala Pro Gln Val Ser Gly Ile Glu Ala Ala Ser Pro Gly His Ala Ala
 5              10              15                  20

GTC ACG GCG GCG TTA GCT AAG GCG GAA GGG GGT GAC GCG CGG CCC AGC        247
Val Thr Ala Ala Leu Ala Lys Ala Glu Gly Gly Asp Ala Arg Pro Ser
            25              30              35

CTG GCC GAG CGG CTG CGG TTG GGG AAC CTC CTG GAG GAC GGG CTA TCG        295
Leu Ala Glu Arg Leu Arg Leu Gly Asn Leu Leu Glu Asp Gly Leu Ser
        40              45              50

TAC AAG GAG AGT TTC ATC GTG CGC TGC TAC GAG GTG GGG ATC AAC AAG        343
Tyr Lys Glu Ser Phe Ile Val Arg Cys Tyr Glu Val Gly Ile Asn Lys
            55              60              65

ACG GCC ACC GTT GAG ACC ATC GCC AAT CTC CTC CAG GAG GTA GGA TGT        391
Thr Ala Thr Val Glu Thr Ile Ala Asn Leu Leu Gln Glu Val Gly Cys
 70              75              80

AAC CAT GCA CAA AGT GTT GGG TTC TCC ACT GAT GGC TTC GCC ACG ACC        439
Asn His Ala Gln Ser Val Gly Phe Ser Thr Asp Gly Phe Ala Thr Thr
 85              90              95                  100

ACT ACA ATG AGA AAA CTT GGT CTT ATT TGG GTG ACG AAC AGA ATG CAC        487
Thr Thr Met Arg Lys Leu Gly Leu Ile Trp Val Thr Asn Arg Met His
            105             110             115

ATT GAG ATC TAC AAG TAC CCA GCT TGG GGT GAT GTT GTT GAG ATC GAA        535
Ile Glu Ile Tyr Lys Tyr Pro Ala Trp Gly Asp Val Val Glu Ile Glu
            120             125                 130

ACA TGG TGC CAA GAA GAT GGA AGA ATT GGT ACC CGT CGT GAT TGG ATC        583
Thr Trp Cys Gln Glu Asp Gly Arg Ile Gly Thr Arg Arg Asp Trp Ile
        135             140             145

CTC AAG GAC CTA GCT AAT GGT GAA GTT ATT GGC AGA GCT ACC AGC AAG        631
Leu Lys Asp Leu Ala Asn Gly Glu Val Ile Gly Arg Ala Thr Ser Lys
        150             155             160

TGG GTC ATG ATG AAC CAA AAT ACA CGG AGA CTT CAG CGG GTC AGT GAT        679
Trp Val Met Met Asn Gln Asn Thr Arg Arg Leu Gln Arg Val Ser Asp
165             170             175             180

GAC GTG AGG GAT GAG GTG TTT ATG CAC TGT CCA AAG GCT CCA AGA TTA        727
Asp Val Arg Asp Glu Val Phe Met His Cys Pro Lys Ala Pro Arg Leu
                185             190             195
```

-continued

```
GCA TTC CCA GAG GAA AAT AAT GGC AGT TTG AAG AAG ATT CCG AAT CTT        775
Ala Phe Pro Glu Glu Asn Asn Gly Ser Leu Lys Lys Ile Pro Asn Leu
            200                 205                 210

TCA GAC CCT GCA GAA TAT TCA AGA CTT GGA CTA GTG CCA AGA AGA GCT        823
Ser Asp Pro Ala Glu Tyr Ser Arg Leu Gly Leu Val Pro Arg Arg Ala
            215                 220                 225

GAC CTG GAC ATG AAC CAA CAT GTC AAT AAT GTT ACT TAC ATA GGT TGG        871
Asp Leu Asp Met Asn Gln His Val Asn Asn Val Thr Tyr Ile Gly Trp
            230                 235                 240

GTC CTC GAA AGT ATA CCT CAA GAT ATA ATT GAT ACA CAC GAG TTA CAA        919
Val Leu Glu Ser Ile Pro Gln Asp Ile Ile Asp Thr His Glu Leu Gln
245                 250                 255                 260

ACA ATC ACT CTC GAC TAC AGA AGG GAG TGT CAA CAG GAT GAT ATA GTT        967
Thr Ile Thr Leu Asp Tyr Arg Arg Glu Cys Gln Gln Asp Asp Ile Val
            265                 270                 275

GAT TCT CTT ACT TGC ATA GAG GAA GGA GAG GAG AAA AGC ATG AAC GGC       1015
Asp Ser Leu Thr Cys Ile Glu Glu Gly Glu Glu Lys Ser Met Asn Gly
            280                 285                 290

TCT GCT TCT GCA GCA GCG CCT CAC AAA GAA GAG CGG CAG CAG TTC CTG       1063
Ser Ala Ser Ala Ala Ala Pro His Lys Glu Glu Arg Gln Gln Phe Leu
            295                 300                 305

CAT TGC TTG AGA TTT GCA GCC AAC GGA CAC GAG ATC AAC CGT GGC CGT       1111
His Cys Leu Arg Phe Ala Ala Asn Gly His Glu Ile Asn Arg Gly Arg
    310                 315                 320

ACC GTG TGG AGG AAG CTA GCT AGA TAAAAGTGTT CTTTCGTCAT AAATGATCTC      1165
Thr Val Trp Arg Lys Leu Ala Arg
325                 330

CTCCATTTCT CTGCTCACGG CTGGCGGCCC TTGTACCACA ATTTTGTGAT GTATTGTTGC     1225

CCTTTGGAAT GTACTCAGCC ATGTATCGGT GCCGATTTGT GACAAAAAAA AAAAAAAAAA     1285

AA                                                                   1287
```

(2) INFORMATION FOR SEQ ID NO:36:

(i) SEQUENCE CHARACTERISTICS:
        (A) LENGTH: 1098 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..1098

(ix) FEATURE:
        (A) NAME/KEY: mat_peptide
        (B) LOCATION: 103..1098

(xi) SEQUENCE DESCRIPTION: SEQ ID NO:36:

```
ATG CTG CGC TGC CAC ACG CCA CCG CAA TGC GCC CGC GCG CCG CTC CGC         48
Met Leu Arg Cys His Thr Pro Pro Gln Cys Ala Arg Ala Pro Leu Arg
-34             -30                 -25                 -20

CAC CAC GGA AGG TGG GAG TCG CCT CCG GCG GCG GCG CCC GCG GTG GTA         96
His His Gly Arg Trp Glu Ser Pro Pro Ala Ala Ala Pro Ala Val Val
            -15                 -10                 -5

GTG CGG TGC GCG CGG GGT GCG CCG CAG GTG TCC GGG ATC GAG GCG GCT        144
Val Arg Cys Ala Arg Gly Ala Pro Gln Val Ser Gly Ile Glu Ala Ala
                1               5                   10

TCG CCG GGC CAC GCG GCT GTC ACG GCG GCG TTA GCT AAG GCG GAA GGG        192
Ser Pro Gly His Ala Ala Val Thr Ala Ala Leu Ala Lys Ala Glu Gly
15                  20                  25                  30
```

```
GGT GAC GCG CGG CCC AGC CTG GCC GAG CGG CTG CGG TTG GGG AAC CTC        240
Gly Asp Ala Arg Pro Ser Leu Ala Glu Arg Leu Arg Leu Gly Asn Leu
                 35                  40                  45

CTG GAG GAC GGG CTA TCG TAC AAG GAG AGT TTC ATC GTG CGC TGC TAC        288
Leu Glu Asp Gly Leu Ser Tyr Lys Glu Ser Phe Ile Val Arg Cys Tyr
             50                  55                  60

GAG GTG GGG ATC AAC AAG ACG GCC ACC GTT GAG ACC ATC GCC AAT CTC        336
Glu Val Gly Ile Asn Lys Thr Ala Thr Val Glu Thr Ile Ala Asn Leu
         65                  70                  75

CTC CAG GAG GTA GGA TGT AAC CAT GCA CAA AGT GTT GGG TTC TCC ACT        384
Leu Gln Glu Val Gly Cys Asn His Ala Gln Ser Val Gly Phe Ser Thr
     80                  85                  90

GAT GGC TTC GCC ACG ACC ACT ACA ATG AGA AAA CTT GGT CTT ATT TGG        432
Asp Gly Phe Ala Thr Thr Thr Thr Met Arg Lys Leu Gly Leu Ile Trp
 95                 100                 105                 110

GTG ACG AAC AGA ATG CAC ATT GAG ATC TAC AAG TAC CCA GCT TGG GGT        480
Val Thr Asn Arg Met His Ile Glu Ile Tyr Lys Tyr Pro Ala Trp Gly
                115                 120                 125

GAT GTT GTT GAG ATC GAA ACA TGG TGC CAA GAA GAT GGA AGA ATT GGT        528
Asp Val Val Glu Ile Glu Thr Trp Cys Gln Glu Asp Gly Arg Ile Gly
            130                 135                 140

ACC CGT CGT GAT TGG ATC CTC AAG GAC CTA GCT AAT GGT GAA GTT ATT        576
Thr Arg Arg Asp Trp Ile Leu Lys Asp Leu Ala Asn Gly Glu Val Ile
        145                 150                 155

GGC AGA GCT ACC AGC AAG TGG GTC ATG ATG AAC CAA AAT ACA CGG AGA        624
Gly Arg Ala Thr Ser Lys Trp Val Met Met Asn Gln Asn Thr Arg Arg
    160                 165                 170

CTT CAG CGG GTC AGT GAT GAC GTG AGG GAT GAG GTG TTT ATG CAC TGT        672
Leu Gln Arg Val Ser Asp Asp Val Arg Asp Glu Val Phe Met His Cys
175                 180                 185                 190

CCA AAG GCT CCA AGA TTA GCA TTC CCA GAG GAA AAT AAT GGC AGT TTG        720
Pro Lys Ala Pro Arg Leu Ala Phe Pro Glu Glu Asn Asn Gly Ser Leu
                195                 200                 205

AAG AAG ATT CCG AAT CTT TCA GAC CCT GCA GAA TAT TCA AGA CTT GGA        768
Lys Lys Ile Pro Asn Leu Ser Asp Pro Ala Glu Tyr Ser Arg Leu Gly
            210                 215                 220

CTA GTG CCA AGA AGA GCT GAC CTG GAC ATG AAC CAA CAT GTC AAT AAT        816
Leu Val Pro Arg Arg Ala Asp Leu Asp Met Asn Gln His Val Asn Asn
        225                 230                 235

GTT ACT TAC ATA GGT TGG GTC CTC GAA AGT ATA CCT CAA GAT ATA ATT        864
Val Thr Tyr Ile Gly Trp Val Leu Glu Ser Ile Pro Gln Asp Ile Ile
    240                 245                 250

GAT ACA CAC GAG TTA CAA ACA ATC ACT CTC GAC TAC AGA AGG GAG TGT        912
Asp Thr His Glu Leu Gln Thr Ile Thr Leu Asp Tyr Arg Arg Glu Cys
255                 260                 265                 270

CAA CAG GAT GAT ATA GTT GAT TCT CTT ACT TGC ATA GAG GAA GGA GAG        960
Gln Gln Asp Asp Ile Val Asp Ser Leu Thr Cys Ile Glu Glu Gly Glu
                275                 280                 285

GAG AAA AGC ATG AAC GGC TCT GCT TCT GCA GCA GCG CCT CAC AAA GAA       1008
Glu Lys Ser Met Asn Gly Ser Ala Ser Ala Ala Ala Pro His Lys Glu
            290                 295                 300

GAG CGG CAG CAG TTC CTG CAT TGC TTG AGA TTT GCA GCC AAC GGA CAC       1056
Glu Arg Gln Gln Phe Leu His Cys Leu Arg Phe Ala Ala Asn Gly His
        305                 310                 315

GAG ATC AAC CGT GGC CGT ACC GTG TGG AGG AAG CTA GCT AGA              1098
Glu Ile Asn Arg Gly Arg Thr Val Trp Arg Lys Leu Ala Arg
    320                 325                 330
```

(2) INFORMATION FOR SEQ ID NO:37:

(i) SEQUENCE CHARACTERISTICS:
    (A) LENGTH: 366 amino acids
    (B) TYPE: amino acid
    (D) TOPOLOGY: linear (ii) MOLECULE TYPE: protein (xi) SEQUENCE DESCRIPTION: SEQ ID NO:37:

```
Met Leu Arg Cys His Thr Pro Pro Gln Cys Ala Arg Ala Pro Leu Arg
-34         -30                 -25                 -20

His His Gly Arg Trp Glu Ser Pro Pro Ala Ala Ala Pro Ala Val Val
            -15                 -10                 -5

Val Arg Cys Ala Arg Gly Ala Pro Gln Val Ser Gly Ile Glu Ala Ala
            1               5                   10

Ser Pro Gly His Ala Ala Val Thr Ala Ala Leu Ala Lys Ala Glu Gly
15                  20                  25                  30

Gly Asp Ala Arg Pro Ser Leu Ala Glu Arg Leu Arg Leu Gly Asn Leu
                35                  40                  45

Leu Glu Asp Gly Leu Ser Tyr Lys Glu Ser Phe Ile Val Arg Cys Tyr
            50                  55                  60

Glu Val Gly Ile Asn Lys Thr Ala Thr Val Glu Thr Ile Ala Asn Leu
            65                  70                  75

Leu Gln Glu Val Gly Cys Asn His Ala Gln Ser Val Gly Phe Ser Thr
        80                  85                  90

Asp Gly Phe Ala Thr Thr Thr Thr Met Arg Lys Leu Gly Leu Ile Trp
95                  100                 105                 110

Val Thr Asn Arg Met His Ile Glu Ile Tyr Lys Tyr Pro Ala Trp Gly
                115                 120                 125

Asp Val Val Glu Ile Glu Thr Trp Cys Gln Glu Asp Gly Arg Ile Gly
                130                 135                 140

Thr Arg Arg Asp Trp Ile Leu Lys Asp Leu Ala Asn Gly Glu Val Ile
            145                 150                 155

Gly Arg Ala Thr Ser Lys Trp Val Met Met Asn Gln Asn Thr Arg Arg
160                 165                 170

Leu Gln Arg Val Ser Asp Asp Val Arg Asp Glu Val Phe Met His Cys
175                 180                 185                 190

Pro Lys Ala Pro Arg Leu Ala Phe Pro Glu Glu Asn Asn Gly Ser Leu
                195                 200                 205

Lys Lys Ile Pro Asn Leu Ser Asp Pro Ala Glu Tyr Ser Arg Leu Gly
            210                 215                 220

Leu Val Pro Arg Arg Ala Asp Leu Asp Met Asn Gln His Val Asn Asn
            225                 230                 235

Val Thr Tyr Ile Gly Trp Val Leu Glu Ser Ile Pro Gln Asp Ile Ile
240                 245                 250

Asp Thr His Glu Leu Gln Thr Ile Thr Leu Asp Tyr Arg Arg Glu Cys
255                 260                 265                 270

Gln Gln Asp Asp Ile Val Asp Ser Leu Thr Cys Ile Glu Glu Gly Glu
                275                 280                 285

Glu Lys Ser Met Asn Gly Ser Ala Ser Ala Ala Pro His Lys Glu
            290                 295                 300

Glu Arg Gln Gln Phe Leu His Cys Leu Arg Phe Ala Ala Asn Gly His
            305                 310                 315

Glu Ile Asn Arg Gly Arg Thr Val Trp Arg Lys Leu Ala Arg
320                 325                 330
```

(2) INFORMATION FOR SEQ ID NO:38:

(i) SEQUENCE CHARACTERISTICS:
        (A) LENGTH: 996 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..996

(xi) SEQUENCE DESCRIPTION: SEQ ID NO:38:

```
TGC GCG CGG GGT GCG CCG CAG GTG TCC GGG ATC GAG GCG GCT TCG CCG        48
Cys Ala Arg Gly Ala Pro Gln Val Ser Gly Ile Glu Ala Ala Ser Pro
 1               5                  10                  15

GGC CAC GCG GCT GTC ACG GCG GCG TTA GCT AAG GCG GAA GGG GGT GAC        96
Gly His Ala Ala Val Thr Ala Ala Leu Ala Lys Ala Glu Gly Gly Asp
             20                  25                  30

GCG CGG CCC AGC CTG GCC GAG CGG CTG CGG TTG GGG AAC CTC CTG GAG       144
Ala Arg Pro Ser Leu Ala Glu Arg Leu Arg Leu Gly Asn Leu Leu Glu
         35                  40                  45

GAC GGG CTA TCG TAC AAG GAG AGT TTC ATC GTG CGC TGC TAC GAG GTG       192
Asp Gly Leu Ser Tyr Lys Glu Ser Phe Ile Val Arg Cys Tyr Glu Val
 50                  55                  60

GGG ATC AAC AAG ACG GCC ACC GTT GAG ACC ATC GCC AAT CTC CTC CAG       240
Gly Ile Asn Lys Thr Ala Thr Val Glu Thr Ile Ala Asn Leu Leu Gln
 65                  70                  75                  80

GAG GTA GGA TGT AAC CAT GCA CAA AGT GTT GGG TTC TCC ACT GAT GGC       288
Glu Val Gly Cys Asn His Ala Gln Ser Val Gly Phe Ser Thr Asp Gly
             85                  90                  95

TTC GCC ACG ACC ACT ACA ATG AGA AAA CTT GGT CTT ATT TGG GTG ACG       336
Phe Ala Thr Thr Thr Thr Met Arg Lys Leu Gly Leu Ile Trp Val Thr
        100                 105                 110

AAC AGA ATG CAC ATT GAG ATC TAC AAG TAC CCA GCT TGG GGT GAT GTT       384
Asn Arg Met His Ile Glu Ile Tyr Lys Tyr Pro Ala Trp Gly Asp Val
        115                 120                 125

GTT GAG ATC GAA ACA TGG TGC CAA GAA GAT GGA AGA ATT GGT ACC CGT       432
Val Glu Ile Glu Thr Trp Cys Gln Glu Asp Gly Arg Ile Gly Thr Arg
130                 135                 140

CGT GAT TGG ATC CTC AAG GAC CTA GCT AAT GGT GAA GTT ATT GGC AGA       480
Arg Asp Trp Ile Leu Lys Asp Leu Ala Asn Gly Glu Val Ile Gly Arg
145                 150                 155                 160

GCT ACC AGC AAG TGG GTC ATG ATG AAC CAA AAT ACA CGG AGA CTT CAG       528
Ala Thr Ser Lys Trp Val Met Met Asn Gln Asn Thr Arg Arg Leu Gln
                165                 170                 175

CGG GTC AGT GAT GAC GTG AGG GAT GAG GTG TTT ATG CAC TGT CCA AAG       576
Arg Val Ser Asp Asp Val Arg Asp Glu Val Phe Met His Cys Pro Lys
            180                 185                 190

GCT CCA AGA TTA GCA TTC CCA GAG GAA AAT AAT GGC AGT TTG AAG AAG       624
Ala Pro Arg Leu Ala Phe Pro Glu Glu Asn Asn Gly Ser Leu Lys Lys
        195                 200                 205

ATT CCG AAT CTT TCA GAC CCT GCA GAA TAT TCA AGA CTT GGA CTA GTG       672
Ile Pro Asn Leu Ser Asp Pro Ala Glu Tyr Ser Arg Leu Gly Leu Val
        210                 215                 220

CCA AGA AGA GCT GAC CTG GAC ATG AAC CAA CAT GTC AAT AAT GTT ACT       720
Pro Arg Arg Ala Asp Leu Asp Met Asn Gln His Val Asn Asn Val Thr
225                 230                 235                 240

TAC ATA GGT TGG GTC CTC GAA AGT ATA CCT CAA GAT ATA ATT GAT ACA       768
Tyr Ile Gly Trp Val Leu Glu Ser Ile Pro Gln Asp Ile Ile Asp Thr
```

```
                  245                 250                 255
CAC GAG TTA CAA ACA ATC ACT CTC GAC TAC AGA AGG GAG TGT CAA CAG           816
His Glu Leu Gln Thr Ile Thr Leu Asp Tyr Arg Arg Glu Cys Gln Gln
            260                 265                 270

GAT GAT ATA GTT GAT TCT CTT ACT TGC ATA GAG GAA GGA GAG GAG AAA           864
Asp Asp Ile Val Asp Ser Leu Thr Cys Ile Glu Glu Gly Glu Glu Lys
            275                 280                 285

AGC ATG AAC GGC TCT GCT TCT GCA GCA GCG CCT CAC AAA GAA GAG CGG           912
Ser Met Asn Gly Ser Ala Ser Ala Ala Ala Pro His Lys Glu Glu Arg
            290                 295                 300

CAG CAG TTC CTG CAT TGC TTG AGA TTT GCA GCC AAC GGA CAC GAG ATC           960
Gln Gln Phe Leu His Cys Leu Arg Phe Ala Ala Asn Gly His Glu Ile
305                 310                 315                 320

AAC CGT GGC CGT ACC GTG TGG AGG AAG CTA GCT AGA                           996
Asn Arg Gly Arg Thr Val Trp Arg Lys Leu Ala Arg
            325                 330
```

(2) INFORMATION FOR SEQ ID NO:39:

(i) SEQUENCE CHARACTERISTICS:
        (A) LENGTH: 332 amino acids
        (B) TYPE: amino acid
        (D) TOPOLOGY: linear (ii) MOLECULE TYPE: protein (xi) SEQUENCE DESCRIPTION: SEQ ID NO:39:

```
Cys Ala Arg Gly Ala Pro Gln Val Ser Gly Ile Glu Ala Ala Ser Pro
1               5                   10                  15

Gly His Ala Ala Val Thr Ala Ala Leu Ala Lys Ala Glu Gly Gly Asp
            20                  25                  30

Ala Arg Pro Ser Leu Ala Glu Arg Leu Arg Leu Gly Asn Leu Leu Glu
        35                  40                  45

Asp Gly Leu Ser Tyr Lys Glu Ser Phe Ile Val Arg Cys Tyr Glu Val
    50                  55                  60

Gly Ile Asn Lys Thr Ala Thr Val Glu Thr Ile Ala Asn Leu Leu Gln
65                  70                  75                  80

Glu Val Gly Cys Asn His Ala Gln Ser Val Gly Phe Ser Thr Asp Gly
                85                  90                  95

Phe Ala Thr Thr Thr Met Arg Lys Leu Gly Leu Ile Trp Val Thr
            100                 105                 110

Asn Arg Met His Ile Glu Ile Tyr Lys Tyr Pro Ala Trp Gly Asp Val
            115                 120                 125

Val Glu Ile Glu Thr Trp Cys Gln Glu Asp Gly Arg Ile Gly Thr Arg
130                 135                 140

Arg Asp Trp Ile Leu Lys Asp Leu Ala Asn Gly Glu Val Ile Gly Arg
145                 150                 155                 160

Ala Thr Ser Lys Trp Val Met Met Asn Gln Asn Thr Arg Arg Leu Gln
                165                 170                 175

Arg Val Ser Asp Asp Val Arg Asp Glu Val Phe Met His Cys Pro Lys
            180                 185                 190

Ala Pro Arg Leu Ala Phe Pro Glu Glu Asn Asn Gly Ser Leu Lys Lys
        195                 200                 205

Ile Pro Asn Leu Ser Asp Pro Ala Glu Tyr Ser Arg Leu Gly Leu Val
    210                 215                 220

Pro Arg Arg Ala Asp Leu Asp Met Asn Gln His Val Asn Asn Val Thr
225                 230                 235                 240
```

```
Tyr Ile Gly Trp Val Leu Glu Ser Ile Pro Gln Asp Ile Ile Asp Thr
            245                 250                 255

His Glu Leu Gln Thr Ile Thr Leu Asp Tyr Arg Arg Glu Cys Gln Gln
            260                 265                 270

Asp Asp Ile Val Asp Ser Leu Thr Cys Ile Glu Glu Gly Glu Glu Lys
            275                 280             285

Ser Met Asn Gly Ser Ala Ser Ala Ala Pro His Lys Glu Glu Arg
        290             295             300

Gln Gln Phe Leu His Cys Leu Arg Phe Ala Ala Asn Gly His Glu Ile
305         310             315                 320

Asn Arg Gly Arg Thr Val Trp Arg Lys Leu Ala Arg
            325             330
```

(2) INFORMATION FOR SEQ ID NO:40:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:40:

```
Xaa Ala Xaa Gly Ala Pro Gln Val Ser Gly Ile Glu Ala Ala
                5                   10
Ser Pro Gly
15
```

(2) INFORMATION FOR SEQ ID NO:41:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

ACGTACGTCC ATGGCTTCGC CGGGCCAC                                            28

(2) INFORMATION FOR SEQ ID NO:42:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

ACGTACGTGA GCTCTTATCT AGCTAGCTTC CTCCA                               35

(2) INFORMATION FOR SEQ ID NO:43:

(i) SEQUENCE CHARACTERISTICS:
        (A) LENGTH: 987 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 11..970

(xi) SEQUENCE DESCRIPTION: SEQ ID NO:43:

```
ACGTACGTCC ATG GCT TCG CCG GGC CAC GCG GCT GTC ACG GCG GCG TTA        49
           Met Ala Ser Pro Gly His Ala Ala Val Thr Ala Ala Leu
           1               5                   10

GCT AAG GCG GAA GGG GGT GAC GCG CGG CCC AGC CTG GCC GAG CGG CTG        97
Ala Lys Ala Glu Gly Gly Asp Ala Arg Pro Ser Leu Ala Glu Arg Leu
    15              20                  25

CGG TTG GGG AAC CTC CTG GAG GAC GGG CTA TCG TAC AAG GAG AGT TTC       145
Arg Leu Gly Asn Leu Leu Glu Asp Gly Leu Ser Tyr Lys Glu Ser Phe
30                  35                  40                  45

ATC GTG CGC TGC TAC GAG GTG GGG ATC AAC AAG ACG GCC ACC GTT GAG       193
Ile Val Arg Cys Tyr Glu Val Gly Ile Asn Lys Thr Ala Thr Val Glu
                50                  55                  60

ACC ATC GCC AAT CTC CTC CAG GAG GTA GGA TGT AAC CAT GCA CAA AGT       241
Thr Ile Ala Asn Leu Leu Gln Glu Val Gly Cys Asn His Ala Gln Ser
            65                  70                  75

GTT GGG TTC TCC ACT GAT GGC TTC GCC ACG ACC ACT ACA ATG AGA AAA       289
Val Gly Phe Ser Thr Asp Gly Phe Ala Thr Thr Thr Thr Met Arg Lys
                80                  85                  90

CTT GGT CTT ATT TGG GTG ACG AAC AGA ATG CAC ATT GAG ATC TAC AAG       337
Leu Gly Leu Ile Trp Val Thr Asn Arg Met His Ile Glu Ile Tyr Lys
    95                  100                 105

TAC CCA GCT TGG GGT GAT GTT GTT GAG ATC GAA ACA TGG TGC CAA GAA       385
Tyr Pro Ala Trp Gly Asp Val Val Glu Ile Glu Thr Trp Cys Gln Glu
110                 115                 120                 125

GAT GGA AGA ATT GGT ACC CGT CGT GAT TGG ATC CTC AAG GAC CTA GCT       433
Asp Gly Arg Ile Gly Thr Arg Arg Asp Trp Ile Leu Lys Asp Leu Ala
                130                 135                 140

AAT GGT GAA GTT ATT GGC AGA GCT ACC AGC AAG TGG GTC ATG ATG AAC       481
Asn Gly Glu Val Ile Gly Arg Ala Thr Ser Lys Trp Val Met Met Asn
            145                 150                 155

CAA AAT ACA CGG AGA CTT CAG CGG GTC AGT GAT GAC GTG AGG GAT GAG       529
Gln Asn Thr Arg Arg Leu Gln Arg Val Ser Asp Asp Val Arg Asp Glu
                160                 165                 170

GTG TTT ATG CAC TGT CCA AAG GCT CCA AGA TTA GCA TTC CCA GAG GAA       577
Val Phe Met His Cys Pro Lys Ala Pro Arg Leu Ala Phe Pro Glu Glu
    175                 180                 185

AAT AAT GGC AGT TTG AAG AAG ATT CCG AAT CTT TCA GAC CCT GCA GAA       625
Asn Asn Gly Ser Leu Lys Lys Ile Pro Asn Leu Ser Asp Pro Ala Glu
190                 195                 200                 205

TAT TCA AGA CTT GGA CTA GTG CCA AGA AGA GCT GAC CTG GAC ATG AAC       673
Tyr Ser Arg Leu Gly Leu Val Pro Arg Arg Ala Asp Leu Asp Met Asn
                210                 215                 220

CAA CAT GTC AAT AAT GTT ACT TAC ATA GGT TGG GTC CTC GAA AGT ATA       721
Gln His Val Asn Asn Val Thr Tyr Ile Gly Trp Val Leu Glu Ser Ile
            225                 230                 235

CCT CAA GAT ATA ATT GAT ACA CAC GAG TTA CAA ACA ATC ACT CTC GAC       769
Pro Gln Asp Ile Ile Asp Thr His Glu Leu Gln Thr Ile Thr Leu Asp
                240                 245                 250

TAC AGA AGG GAG TGT CAA CAG GAT GAT ATA GTT GAT TCT CTT ACT TGC       817
Tyr Arg Arg Glu Cys Gln Gln Asp Asp Ile Val Asp Ser Leu Thr Cys
    255                 260                 265

ATA GAG GAA GGA GAG GAG AAA AGC ATG AAC GGC TCT GCN TCT GCA GCA       865
Ile Glu Glu Gly Glu Glu Lys Ser Met Asn Gly Ser Ala Ser Ala Ala
270                 275                 280                 285

GCG CCT CAC AAA GAA GAG CGG CAG CAG TTC CTG CAT TGC TTG AGA TTT       913
Ala Pro His Lys Glu Glu Arg Gln Gln Phe Leu His Cys Leu Arg Phe
                290                 295                 300
```

```
GCA GCC AAC GGA CAC GAG ATC AAC CGT GGC CGT ACC GTG TGG AGG AAG        961
Ala Ala Asn Gly His Glu Ile Asn Arg Gly Arg Thr Val Trp Arg Lys
        305                 310                 315

CTA GCT AGA TAAGAGCTCA CGTACGT                                         987
Leu Ala Arg
        320

(2) INFORMATION FOR SEQ ID NO:44:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO:44:

Met Ala Ser Pro Gly His Ala Ala Val Thr Ala Ala Leu Ala Lys Ala
 1               5                  10                  15

Glu Gly Gly Asp Ala Arg Pro Ser Leu Ala Glu Arg Leu Arg Leu Gly
            20                  25                  30

Asn Leu Leu Glu Asp Gly Leu Ser Tyr Lys Glu Ser Phe Ile Val Arg
        35                  40                  45

Cys Tyr Glu Val Gly Ile Asn Lys Thr Ala Thr Val Glu Thr Ile Ala
    50                  55                  60

Asn Leu Leu Gln Glu Val Gly Cys Asn His Ala Gln Ser Val Gly Phe
65                  70                  75                  80

Ser Thr Asp Gly Phe Ala Thr Thr Thr Met Arg Lys Leu Gly Leu
                85                  90                  95

Ile Trp Val Thr Asn Arg Met His Ile Glu Ile Tyr Lys Tyr Pro Ala
                100                 105                 110

Trp Gly Asp Val Val Glu Ile Glu Thr Trp Cys Gln Glu Asp Gly Arg
            115                 120                 125

Ile Gly Thr Arg Arg Asp Trp Ile Leu Lys Asp Leu Ala Asn Gly Glu
        130                 135                 140

Val Ile Gly Arg Ala Thr Ser Lys Trp Val Met Met Asn Gln Asn Thr
145                 150                 155                 160

Arg Arg Leu Gln Arg Val Ser Asp Asp Val Arg Asp Glu Val Phe Met
                165                 170                 175

His Cys Pro Lys Ala Pro Arg Leu Ala Phe Pro Glu Glu Asn Asn Gly
            180                 185                 190

Ser Leu Lys Lys Ile Pro Asn Leu Ser Asp Pro Ala Glu Tyr Ser Arg
        195                 200                 205

Leu Gly Leu Val Pro Arg Arg Ala Asp Leu Asp Met Asn Gln His Val
    210                 215                 220

Asn Asn Val Thr Tyr Ile Gly Trp Val Leu Glu Ser Ile Pro Gln Asp
225                 230                 235                 240

Ile Ile Asp Thr His Glu Leu Gln Thr Ile Thr Leu Asp Tyr Arg Arg
                245                 250                 255

Glu Cys Gln Gln Asp Asp Ile Val Asp Ser Leu Thr Cys Ile Glu Glu
            260                 265                 270

Gly Glu Glu Lys Ser Met Asn Gly Ser Ala Ser Ala Ala Pro His
        275                 280                 285

Lys Glu Glu Arg Gln Gln Phe Leu His Cys Leu Arg Phe Ala Ala Asn
    290                 295                 300

Gly His Glu Ile Asn Arg Gly Arg Thr Val Trp Arg Lys Leu Ala Arg
305                 310                 315                 320
```

(2) INFORMATION FOR SEQ ID NO:45:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

```
ACGTACGTGG CCATATTGGC CTCTAGCTAG CTTCCTCCAC A                 41
```

(2) INFORMATION FOR SEQ ID NO:46:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:46:

```
ACGTACGTGG CCAGAGAGGC CATGCTGCGC TGCCACACG                    39
```

(2) INFORMATION FOR SEQ ID NO:47:

(i) SEQUENCE CHARACTERISTICS:
        (A) LENGTH: 1140 base pairs
        (B) TYPE: nucleic acid
        (C) STRANDEDNESS: single
        (D) TOPOLOGY: linear (ii) MOLECULE TYPE: DNA (iv) ANTI-SENSE: YES (xi) SEQUENCE DESCRIPTION: SEQ ID NO:47:

```
ACGTACGTGG CCATATTGGC CTCTAGCTAG CTTCCTCCAC ACGTACGGC CACGGTTGAT    60
CTCGTGTCCG TTGGCTGCAA ATCTCAAGCA ATGCAGGAAC TGCTGCCGCT CTTCTTTGTG   120
AGGCGCTGCT GCAGAAGCAG AGCCGTTCAT GCTTTTCTCC TCTCCTTCCT CTATGCAAGT   180
AAGAGAATCA ACTATATCAT CCTGTTGACA CTCCCTTCTG TAGTCGAGAG TGATTGTTTG   240
TAACTCGTGT GTATCAATTA TATCTTGAGG TATACTTTCG AGGACCCAAC CTATGTAAGT   300
AACATTATTG ACATGTTGGT TCATGTCCAG GTCAGCTCTT CTTGGCACTA GTCCAAGTCT   360
TGAATATTCT GCAGGGTCTG AAAGATTCGG AATCTTCTTC AAACTGCCAT TATTTTCCTC   420
TGGGAATGCT AATCTTGGAG CCTTTGGACA GTGCATAAAC ACCTCATCCC TCACGTCATC   480
ACTGACCCGC TGAAGTCTCC GTGTATTTTG GTTCATCATG ACCCACTTGC TGGTAGCTCT   540
GCCAATAACT TCACCATTAG CTAGGTCCTT GAGGATCCAA TCACGACGGG TACCAATTCT   600
TCCATCTTCT TGGCACCATG TTTCGATCTC AACAACATCA CCCCAAGCTG GTACTTGTA    660
GATCTCAATG TGCATTCTGT TCGTCACCCA AATAAGACCA AGTTTTCTCA TTGTAGTGGT   720
CGTGGCGAAG CCATCAGTGG AGAACCCAAC ACTTTGTGCA TGGTTACATC CTACCTCCTG   780
GAGGAGATTG GCGATGGTCT CAACGGTGGC CGTCTTGTTG ATCCCCACCT CGTAGCAGCG   840
CACGATGAAA CTCTCCTTGT ACGATAGCCC GTCCTCCAGG AGGTTCCCCA ACCGCAGCCG   900
CTCGGCCAGG CTGGGCCGCG CGTCACCCCC TTCCGCCTTA GCTAACGCCG CCGTGACAGC   960
CGCGTGGCCC GGCGAAGCCG CCTCGATCCC GGACACCTGC GGCGCACCCC GCGCGCACCG  1020
```

```
CACTACCACC GCGGGCGCCG CCGCCGGAGG CGACTCCCAC CTTCCGTGGT GGCGGAGCGG    1080

CGCGCGGGCG CATTGCGGTG GCGTGTGGCA GCGCAGCATG GCCTCTCTGG CCACGTACGT    1140

(2) INFORMATION FOR SEQ ID NO:48:

(i) SEQUENCE CHARACTERISTICS:
         (A) LENGTH:  20 amino acids
         (B) TYPE:    amino acids
         (D) TOPOLOGY: linear (ii) MOLECULE TYPE:  peptide (xi) SEQUENCE DESCRIPTION:  SEQ ID NO:48:

Arg Gln Gln Phe Leu His Cys Leu Arg Phe Ala Ala Asn Gly His
                 5                  10                  15
Glu Ile Asn Arg Gly
                20

(2) INFORMATION FOR SEQ ID NO:49:

(i) SEQUENCE CHARACTERISTICS:
         (A) LENGTH:  102 base pairs
         (B) TYPE:    nucleic acid
         (C) STRANDEDNESS: single
         (D) TOPOLOGY: linear (ii) MOLECULE TYPE:  DNA (xi) SEQUENCE DESCRIPTION:  SEQ ID NO:49:

ATG CTG CGC TGC CAC ACG CCA CCG CAA TGC GCC CGC GCG CCG               42
Met Leu Arg Cys His Thr Pro Pro Gln Cys Ala Arg Ala Pro
 1               5                  10

CTC CGC CAC CAC GGA AGG TGG GAG TCG CCT CCG GCG GCG GCG               84
Leu Arg His His Gly Arg Trp Glu Ser Pro Pro Ala Ala Ala
 15                 20                  25

CCC GCG GTG GTA GTG CGG                                              102
Pro Ala Val Val Val Arg
    30
```

ACYL-ACP THIOESTERASE NUCLEIC ACIDS FROM MAIZE AND METHODS OF ALTERING PALMITIC ACID LEVELS IN TRANSGENIC PLANTS THEREWITH

This application claims the benefit of U.S. provisional Application No. 60/045,827, filed May 5, 1997.

FIELD OF INVENTION

This invention relates to the preparation and use of nucleic acid fragments or genes encoding acyl-acyl carrier protein thioesterase enzymes to create transgenic plants having altered oil profiles.

BACKGROUND OF THE INVENTION

Oils produced by plants can be found in a wide variety of products including soaps, lubricants, and foods. Interestingly, different plant species synthesize various oil types. For example, coconut and palm plants produce oils that are abundant in fatty acids having medium chain lengths (10–12 carbon atoms). These oils are used in the manufacture of soaps, detergents and surfactants and represent a US market size greater than $350 million per year. Other plants, such as rape, produce oils abundant in long chain fatty acids (22 carbon atoms) and are used as lubricants and anti-slip agents. Additional applications of plant oils include their use in plasticizers, coatings, paints, varnishes and cosmetics (Volker et al., (1992) Science 257:72–74; Ohlrogge, (1994) Plant Physiol. 104:821–826). However, the predominant use of plant oils is in the production of food and food products.

The characteristics of oils are determined predominately by the number of carbon atoms comprising the fatty acid chain. Most oils derived from plants are composed of varying amounts of palmitic (16:0), stearic (18:0), oleic (18:1), linoleic (18:2) and linolenic (18:3) fatty acids. Palmitic and stearic acids are 16- and 18-carbon long saturated fatty acids, respectively. Conventionally, they are designated as "saturated" since the fatty acid chains have no double bonds and therefore contain the maximal number of hydrogen atoms possible. Saturated fatty acids are linear molecules and tend to form self-stacked structures thereby resulting in high melting temperatures. For example, animal fats, which are solid at room temperature, are typically high in saturated fatty acids. The other predominant fatty acids found in plant oils, oleic, linoleic, and linolenic, are 18-carbon long fatty acid chains having one, two, and three double bonds therein, respectively. Oleic acid is typically considered a mono-unsaturated fatty acid, whereas linoleic and linolenic are considered to be poly-unsaturated fatty acids. These fatty acid chains are nonlinear due to bending induced by the insertion of the double bond in the cis conformation. Double bond insertion decreases melting point due to the inability of the fatty acid molecules to self-stack. For example, vegetable oils, which are typically liquid at room temperature, are high in unsaturated fatty acids.

Over the years, vegetable oils have gradually replaced animal-derived oils and fats as the major source of dietary fat intake. However, saturated fat in most industrialized nations has remained at 15 to 20% of total caloric intake. The United States Department of Agriculture has recently recommended that saturated fats make up less than 10% of daily caloric intake. To facilitate consumer awareness, current labeling guidelines issued by the United States Food and Drug Administration now require total saturated fatty acid levels be less than 1.0 g per 14 g serving to receive the "low-sat" label and less than 0.5 g per 14 g serving to receive the "no-sat" label. This means that the saturated fatty acid content of plant oils would need be less than 7% and 1.75% to receive the "low sat" and "no sat" label, respectively. Therefore, there has been a surge in increased consumer demand for "low-sat" oils. To date, this has been met principally with canola oil, and to a much lesser degree with sunflower, and safflower oils.

The total saturated fatty acid level of corn oil, approximately 13.9%, does not meet the labeling guidelines discussed above. On average, corn oil is comprised of 11.5% palmitic acid, 2.2% stearic acid, 26.6% oleic acid, 58.7% linoleic acid, and 0.8% linolenic acid. Corn oil also contains 0.2% arachidic acid, a twenty-carbon saturated fatty acid (Dunlap et. al., (1995) J. Amer. Oil Chem. Soc. 72:981–987). The fatty acid composition of corn oil instills it with properties that are most desirable in edible oils. These include properties such as heat stability, flavor, and long shelf life. However, consumer demand for "low sat" oils has resulted in a significant decrease in corn oil utilization and thus market size. Therefore, a corn oil with low levels of saturated fatty acids is highly desirable, in that it would meet the consumer demand for healthier oils while having most or all of the properties that made corn oil popular in the past and a preferred oil for many uses.

Although corn oil with low levels of saturated fatty acids is desirable, there is also a demand for corn oil having high levels of saturated fatty acids. For example, about half of all consumption of vegetable oils is in the form of margarine and shortening. However, the use of corn oil for these products requires chemical modification of the oil due to its low melting point. Typically, an increased melting point is achieved through catalytic hydrogenation which increases the level of saturated fatty acids. In this process, hydrogen atoms are added at double bonds found in the fatty acid through the use of a catalyst. An additional side reaction that occurs during hydrogenation is the substantial conversion of the naturally occurring cis double bonds to the trans isomer, which are more stable. There have been some controversies regarding health risks associated with intake of oils containing trans double bonds. In a recent study, it was shown that a diet high in trans isomer consumption actually raised serum lipoprotein profiles and cholesterol levels (Mensink and Katan (1990) N. Eng. J. Med. 323:439–445). Therefore, production of oil containing a higher content of saturated fatty acids would reduce the need for hydrogenation in margarine and shortening production thereby reducing the content of trans isomers in the diet. In addition, partial hydrogenation typically increases cost an additional 2 to 3 cents per pound of oil. Therefore, a corn oil with naturally high saturates levels is also highly desirable for production of margarine and shortening since this would fulfill a market need while reducing manufacture cost.

Corn is typically not considered to be an oil crop as compared to soybean, canola, sunflower and the like. In fact, the oil produced by corn is considered to be a byproduct of the wet milling process used to extract starch. Because of this, there has been little interest in modification of saturate levels of corn oil until that disclosed herein.

SUMMARY OF THE INVENTION

In the present invention, acyl-acyl carrier protein thioesterases (acyl-ACP thioesterases) from maize have been isolated and cloned. The saturate level of oils found in plant cells can be altered by modifying the expression and activity levels of acyl-ACP thioesterases within the cell.

One aspect of the disclosed invention is genes and nucleic acid fragments encoding maize acyl-ACP thioesterases. More specifically, the isolated genes and nucleic acid fragments herein encode maize palmitoyl-ACP thioesterase, hereinafter PTE, and maize oleoyl-ACP thioesterase, hereinafter OTE. Maize PTE and OTE hydrolyze acyl-ACP units into free fatty acids and ACP in somewhat a selective although not specific manner.

Another aspect of the invention relates to altering saturate levels within a cell by modifying expression levels of PTE and OTE. The genes and nucleic acid fragments disclosed herein can be used to alter saturate levels by placing said genes and fragments in the antisense orientation. Plants being transformed with PTE in the antisense orientation results in the oils of said plants having lowered 16:0 and lowered total saturate levels. Plants being transformed with OTE in the antisense orientation results in the oils of said plant having increased 16:0 and increased total saturate levels. Results similar to those disclosed herein with antisense can also be produced through the use of ribozymes designed specifically for PTE and OTE.

Another aspect of the invention relates to altering saturate levels within a cell by modifying expression levels of PTE and OTE through expressing the genes and nucleic acid fragments thereof in the sense orientation. Expression of said genes and fragments thereof in the sense orientation can result in cosuppression effects. Plants being transformed with PTE in the sense orientation producing cosuppression effects produce plant oils having lowered 16:0 and lowered total saturate levels. Plants being transformed with OTE in the sense orientation producing cosuppression effects produce plant oils having increased 16:0 and increased total saturate levels.

In yet a further aspect, the genes and fragments disclosed herein can alter the saturate levels of plant oils when in the sense orientation by over-expressing the proteins encoded thereby. Over-expressing PTE in a plant can produce oils having increased 16:0 and increased total saturate levels. Over-expressing OTE in a plant can produce oils having lowered 16:0 and lowered total saturate levels.

An additional aspect of the present invention is the production of a chimeric gene using the genes and nucleic acid fragments disclosed herein in combination with promoter regulatory elements and the use of said chimeric genes within a plant cell.

Yet an additional aspect of the present invention is the transformation of plant species disclosed herein with said chimeric genes.

A further aspect of the present invention is changes in the rates of acyl-ACP hydrolysis associated with PTE and OTE thus altering 16:0 and total saturate levels of plants containing said genes through mutagenesis Other aspects, embodiments, advantages, and features of the present invention will become apparent from the following specification.

DETAILED DESCRIPTION OF THE INVENTION

The present invention relates to methods and compositions for obtaining plant oils having altered saturate levels. The following phrases and terms are defined below:

By "altered saturate levels" is meant that the level of total saturated fatty acids of a plant oil produced by a modified plant is different from that of a normal or non-modified plant. Alterations in total saturate levels can be achieved by either increasing saturated fatty acid thereby resulting in a decrease in unsaturated fatty acids, or by increasing unsaturated fatty acids thereby decreasing saturated fatty acids.

By "antisense RNA" is meant an RNA transcript that comprises sequences complementary to a target RNA and/or mRNA or portions thereof and that blocks the expression of a target gene by interfering with the processing, transport, and/or translation of its primary transcript and/or mRNA. The complementarity may exist with any part of the target RNA, i.e., at the 5' non-coding sequences, 3' non-coding sequence, introns, or the coding sequence. Antisense RNA is typically a complement (mirror image) of the sense RNA.

By "cDNA" is meant DNA that is complementary to and derived from a mRNA.

By "chimeric DNA construction" is meant a recombinant DNA containing genes or portions thereof from one or more species in either the sense or antisense orientation.

By "complementarity" is meant a nucleic acid that can form hydrogen bond(s) with other nucleic acid sequences either through traditional Watson-Crick or other non-traditional types of base paired interactions.

By "constitutive promoter" is meant promoter elements that direct continuous gene expression in all cell types and at all times (i.e., actin, ubiquitin, CaMV 35S, 35T, and the like).

By "cosuppression" is meant the introduction of a foreign gene having substantial homology to an endogenous gene, and in a plant cell causes the reduction in activity of the foreign gene and/or the endogenous protein product.

By "degenerate variations thereof" is meant the changing of a DNA sequence using the degenerate nature of the genetic code to encode proteins having the same amino acid sequence yet having a different DNA sequence.

By "developmental specific" promoter is meant promoter elements responsible for gene expression at specific plant developmental stages, such as in early or late embryogenesis.

By "enhancer" is meant nucleotide sequence elements which can stimulate promoter activity such as those from maize streak virus (MSV) and alcohol dehydrogenase intron 1.

By "enzymatic nucleic acid molecule" is meant all nucleic acid molecules with enzymatic activity having complimentarily in a substrate binding region to a specified gene target, and which is able to specifically cleave that target. The term enzymatic nucleic acid is used interchangeably with phrases such as ribozymes, catalytic RNA, enzymatic RNA, catalytic DNA, nucleozyme, DNAzyme, RNA enzyme, and the like. All of these terminologies describe nucleic acid molecules with enzymatic activity.

By "expression" as used herein, is meant the transcription and stable accumulation of the enzymatic nucleic acid molecules, mRNA, and/or the antisense RNA inside a plant cell. Expression of genes also involves transcription of the gene and translation of the mRNA into precursor or mature proteins.

By "foreign" or "heterologous gene" is meant a gene encoding a protein whose exact amino acid sequence is not normally found in the host cell, but is introduced by standard gene transfer techniques.

By "gene" is meant to include all genetic material involved in protein expression including chimeric DNA constructions, genes, plant genes and portions thereof.

By "genome" is meant genetic material contained in each cell of an organism and/or virus.

By "inducible promoter" is meant promoter elements which are responsible for expression of genes in response to a specific signal, such as: physical stimuli (heat shock genes); light (RUBP carboxylase); hormone (Em); metabolites and stress.

By "inhibit" is meant that the activity of enzymes such as maize embryo acyl-ACP thioesterase or level of mRNAs encoded by these genes is below that observed in the absence of the inhibitor.

By "modified plant" is meant a plant wherein the mRNA, protein levels or protein specific activity levels of maize acyl-ACP thioesterases have been altered relative to that seen in a unmodified plant. Modification can be achieved by methods such as antisense, cosuppression, over-expression, ribozymes, or chemical mutagenesis.

By "plant" is meant a photosynthetic organism including both eukaryotes and prokaryotes.

By "promoter regulatory element" is meant nucleotide sequence elements within a nucleic fragment or gene which controls the expression of that nucleic acid fragment or gene. Promoter sequences provide the recognition for. RNA polymerase and other transcriptional factors required for efficient transcription. Promoter regulatory elements from a variety of sources can be used efficiently in plant cells to express sense and antisense gene constructs. They can also be used to express ribozymes. Promoter regulatory elements are also meant to include constitutive, tissue-specific, developmental-specific, inducible promoters and the like. Promoter regulatory elements may also include certain enhancer sequence elements that improve transcriptional efficiency.

By "tissue-specific" promoter is meant promoter elements responsible for gene expression in specific cell or tissue types, such as the leaves or seeds (i.e., zein, oleosin, napin, ACP, globulin and like).

By "transgenic plant" is meant a plant expressing a chimeric gene introduced through transformation efforts.

In nature, maize acyl-ACP thioesterases catalyze the hydrolytic cleavage of palmitic acid, stearic acid, and oleic acid from ACP in a somewhat selective although not specific manner. It has been found herein that changes in RNA levels, protein levels or protein specific activity levels of maize acyl-ACP thioesterases in plant cells alters fatty acid profiles thereby altering saturate levels in plant oils.

In corn seed oil, the predominant fatty acids are linoleic acid (18:2 at about 59%), oleic acid (18:1 at about 26%) and palmitic (16:0 at about 11%), with stearic acid (18:0) generally comprising at about 2.5% or less (Glover and Mertz, (1987) in: Nutritional Quality of Cereal Grains: genetic and agronomic improvement., p.183–336, (eds. Olson, R. A. and Frey, K. J.) Amer. Soc. Agronomy, Inc., Madison, Wis.; Fitch-Haumann, (1985) J. Am. Oil. Chem. Soc. 62:1524–1531). In plants, biosynthesis of fatty acids is initiated in the plastids where they are synthesized as thioesters of acyl carrier protein (ACP) by a fatty acid synthase complex. More specifically, fatty acid production is accomplished by a series of condensation reactions involving addition of malonyl-ACP sequentially to a growing fatty acid acyl chain. Most fatty acid-ACP units reach carbon chain lengths of 16 or 18, with the majority of C18 fatty acids then becoming desaturated at the C9 position to produce oleic acid.

Both saturated and unsaturated fatty acid-ACP units are hydrolyzed by acyl-ACP thioesterases to produce free fatty acids. These free fatty acids then cross the plastid membrane to the cytosol where they are incorporated into plant oils (Somerville and Browse, (1991) Science 252:80–87; Browse and Sommerville (1991) Annu. Rev. Plant Physiol. Plant Mol. Biol. 42:467–506; Harwood (1989) Critical Reviews in Plant Sci. 8:1–43; Chasan (1995) Plant Cell 7:235–237). Although acyl-ACP thioesterases are selective, they are not substrate specific. Instead, OTE affects the level of 18:1 as well as 16:0 and PTE affects the level of 16:0 and other fatty acids. Therefore, increasing or reducing levels of acyl-ACP thioesterases (PTE and OTE) in plants or altering enzymatic specific activity of said thioesterases will alter the overall rates of fatty acid-ACP hydrolysis. Thus, these changes will alter both saturate and unsaturate levels in the oil produced by said plant.

As further described herein, PTE and OTE may be used to modify the saturate levels in oils produced by transgenic plants. Preferably, genes and nucleic fragments encoding for PTE and OTE are isolated from maize. More preferably, the PTE sequences are those disclosed herein as SEQ ID NO:4, SEQ ID NO:5, SEQ ID NO:6, SEQ ID NO:8, SEQ ID NO:12, SEQ ID NO:16, SEQ ID NO:19, SEQ ID NO:27, SEQ ID NO:28, and SEQ ID NO:29. In addition, the more preferred OTE sequences are those disclosed herein as SEQ ID NO:33, SEQ ID NO:35, SEQ ID NO:36, SEQ ID NO:38, SEQ ID NO:43, and SEQ ID NO:47.

By altering maize acyl-ACP thioesterase gene expression or the level of the protein's activity, the saturate levels of a plant oil may be modified. Alterations in maize acyl-ACP thioesterase gene expression levels can be achieved using antisense techniques. Antisense inhibition has been used to inhibit a variety of plant target genes (van der Krol et al., (1988) Gene 72:45–50; Ecker et al., (1986) Proc. Natl. Acad. Sci. USA 83:5372–5376; van der Krol et al., (1988) Biotechniques 6:958–976; Knutzon et al.,(1992) Proc. Natl. Acad. Sci. 89:2624). Typically, an antisense probe can be made using polymerase chain reaction techniques, hereinafter PCR, wherein small oligonucleotide primers are used to make an DNA molecule in the 5' to 3' direction that is the complement (mirror image) of the coding or sense strand of said DNA. The DNA encoding the antisense RNA molecule is typically placed 3' to a desired promoter regulatory element and plant cells of interest are transformed as described herein. The general methods and teachings of antisense have been disclosed in Shewmaker et al., in U.S. Pat. Nos. 5,107,065 and 5,453,566, which are incorporated by reference.

The length of the antisense portion needed to produce a phenotypic effect can vary. For example, phenotypic effects due to antisense have been shown using complete cDNA sequences (Sheehy et al., Proc. Natl. Acad. Sci. USA (1988) 85:8805–8809) as well as partial cDNA sequences (Cannon et al., Plant Molec. Biol. (1990) 15:39–47). There is also evidence that the 3' noncoding sequences and fragments of 5' coding sequences containing as few as 41 base pairs can both have utility in producing antisense effects (Ch'ng et al., (1989) Proc. Natl. Acad. Sci. USA, 86:10006–10010; Cannon et al., Plant Molec. Biol. (1990) 15:39–47).

It is expected that genomic DNA sequences associated with maize acyl-ACP thioesterases, including the 5' and 3' noncoding regions and intron sequences, can be used to create chimeric genes constructs encoding for antisense RNA. Isolation and cloning of said genomic DNA encoding maize acyl-ACP thioesterases can be performed using a variety of methods detailed in Sambrook et al., (Molecular Cloning, A Laboratory Manual, $2^{nd}$ Ed. (1989) Cold Spring Harbor Laboratory Press), which is incorporated herein by reference.

As further described herein, the nucleic acid fragments and genes encoding maize PTE are cloned in the antisense orientation. Preferably, the maize globulin and maize ubiquitin promoters can be used to produce the chimeric genes for plant transformation. Maize tissues transformed with maize PTE genes and fragments in the antisense orientation can produce plant oils having altered fatty acid profiles relative to nontransformed controls. When using the PTE gene or fragments in the antisense orientation, it is most desirable to decrease 16:0 levels within the oils produced by the transgenic plant. Typically, as stated previously, the 16:0 levels in maize oil are about 11.0%; however, when using the PTE gene or fragments thereof in the antisense orientation, the 16:0 levels in maize plants range from about 4.8 to about 9.5%; preferably from about 4.8 to about 7.0%; more preferably from about 4.8 to about 4.9%, and most preferred 3.0%. The total saturate levels range from about 3.0 to about 8.3%; more preferably about 3.0 to about 6.8%, and most preferred 3.0%.

Another aspect of the present invention is nucleic acid fragments and genes encoding maize OTE cloned in the antisense orientation. Maize tissues transformed with maize OTE genes and fragments in the antisense orientation can produce plant oils having altered fatty acid profiles relative to nontransformed controls. When using OTE genes or nucleic acid fragments in the antisense orientation, it is most desirable to increase 16:0 levels within the oils produced by transgenic plants. When using these genes or fragments, the 16:0 levels in maize transgenic plants range from about 18 to about 28.3%; preferably from about 23.9 to about 28.3%; and more preferred about 28.3%. The total saturate levels range from about 18.0 to about 23.9%; more preferably from about 24.0 to about 28.9%, and most preferred 28.9%.

In addition to antisense, another way to manipulate gene or nucleic acid expression is with cosuppression. The use of cosuppression to alter expression of endogenous plant genes is well described in the art. Typically, a genomic clone, a cDNA clone, or portions thereof are inserted in the sense orientation 3' to the promoter regulatory element of choice. Cosuppression of endogenous genes has been demonstrated using entire cDNA sequences (Napoli et al., (1990) Plant Cell 2:279–289; van der Krol et al., (1990) 2:291–299) as well as a partial cDNA sequence (Smith et al., (1990) Mol. Gen. Genetics 224:477–481). Endogenous genes can also be inhibited by the introduction of noncoding regions of a gene of interest into a cell (Brusslan et. al., (1993) Plant Cell 5:667–677; Matzke et al., (1993) Plant Molecular Biology 16:821–830) In a related aspect, promoter regulatory elements corresponding to the endogenous gene of interest have also been shown to be suitable agents for inducing cosuppression events and are included herein (Brusslan et al., (1993) Plant Cell 5:667–677; Kinney (1996) Development of genetically engineered oilseeds. 12$^{th}$ International Symposium on Plant Lipids, Toronto, Canada Jul. 7–12, 1996). Therefore, another aspect of the present invention is the altering of saturate levels in plant oil composition through inhibition of genes expressing maize acyl-ACP thioesterase using cosuppression techniques.

For cosuppression, the nucleic acid fragments and genes encoding maize PTE are cloned in the sense orientation. Maize tissues transformed with maize PTE genes and fragments in the sense orientation can produce plant oils having altered fatty acid profiles relative to nontransformed controls. When using the PTE gene or fragments in the sense orientation resulting in a cosuppression effect, it is most desirable to decrease 16:0 levels within the oils produced by the transgenic plant. Typically, as stated previously, the 16:0 levels are about 11.0%; however, when using the PTE gene or fragments thereof in the sense orientation resulting in a cosuppression effect, the 16:0 levels in maize transgenic plants range from about 4.8 to about 9.5%; preferably from about 4.8 to about 7.0%; more preferably from about 4.8 to about 4.9%, and most preferred 3.0. The total saturate levels range from about 3.0 to about 8.3%; more preferably about 3.0 to about 6.8%, and most preferred 3.0%.

Another aspect of the present invention is nucleic acid fragments and genes encoding maize OTE cloned in the sense orientation to produce cosuppression effects. Maize tissues transformed with maize OTE genes and fragments in the sense orientation can produce plant oils having altered fatty acid profiles relative to nontransformed controls. When using OTE genes or nucleic acid fragments in the sense orientation producing a cosuppression event, it is most desirable to increase 16:0 levels within the oils produced by the transgenic plant. When using these genes or fragments, the 16:0 levels in maize transgenic plants range from about 18 to about 28.3%; preferably from about 23.9 to about 28.3%; and more preferred about 28.3%. The total saturate levels range from about 18.0 to about 23.9%; more preferably about 24.0 to about 28.9%, and most preferred 28.9%.

Yet another aspect of the present invention is the altering of saturate levels in plant oils by inhibiting expression of maize acyl-ACP thioesterases using ribozymes. Ribozymes can be targeted to virtually any RNA transcript and efficient cleavage has been achieved in vivo and in vitro (Zaug et al., (1986) Nature 324:429; Kim et al., (1987) Proc. Natl. Acad. Sci. USA 84:8788; Dreyfus, (1988) Einstein Quarterly J. Bio. Med. 6:92; Haselof and Gerlach (1988) Nature 334:585; Cech (1988) J. Amer. Med. Assoc. 260:3030; and Jefferies et al., (1989) Nucl. Acids. Res. 17:1371). Because of their sequence-specificity, ribozymes may be used as efficient tools to modulate gene expression in a variety of organisms (Usman and McSwiggen, (1995) Ann. Rep. Med. Chem. 30:285–294; and Christoffersen and Marr, (1995) J. Med. Chem. 38:2023–2037). Methods of producing ribozymes against targets is disclosed in the PCT publication WO97/10328, which is incorporated herein by reference. Expressing ribozymes targeted to RNA encoding maize acyl-ACP thioesterases genes or fragments is another mechanism for down regulation of mRNA levels, decreasing protein levels and subsequent alterations in the saturate levels of plant oils.

Another mechanism by which plant oils can be modified is by over-expressing maize PTE or maize OTE. This can be achieved by placing the genes or nucleic acid fragments for these proteins in the sense orientation 3' to the promoter regulatory element of choice. These chimeric genes can then be transformed into plants, thereby producing plant oils having altered saturate levels relative to nontransformed controls. Over-expression of PTE will result in transgenic plants having increased 16:0 levels which range from about 18 to about 28.3%; preferably from about 23.9 to about 28.3%; and more preferred about 28.3%. The total saturate levels range from about 18.0 to about 23.9%; more preferably about 24.0 to about 28.9%, and most preferred 28.9%. Obviously, the over-expression of OTE will result in transgenic plants producing oils having lowered 16:0 levels and saturate levels.

In addition to using these genes and nucleic fragments for maize, other plant species which may be modified include but are not limited to soybean, Brassicaceae sp., canola, rape, sunflower, flax, safflower, coconut, palm, olive, peanut, cotton, castor bean, coriander, Crambe sp., Cuphea sp., Euphorbia sp., Oenothera sp., jojoba, Lesquerella sp., marigold, Limnanthes sp., Vernonia sp., *Sinapis alba*, and cocoa, with maize being most preferred. Most if not all of these plant species have been previously transformed by those skilled in the art.

In order to produce transgenic plants having altered oil compositions described herein, vectors containing chimeric genes or fragments of maize acyl-ACP thioesterases, in either the sense or antisense orientation, or ribozymes as described herein, are inserted into the plant genome. Preferably, these recombinant vectors are capable of stable integration into the plant genome and selection of transformed plant lines expressing selectable agents are expressed either by constitutive or inducible promoters in the plant cell. The chimeric genes containing maize acyl-ACP thioesterase genes or fragments, either in the sense, or antisense orientation, or genes encoding ribozymes designed against maize acyl-ACP thioesterase genes are expressed in the plant cells under the control of a constitutive, tissue-specific, developmental, or inducible promoter and the like.

Several techniques exist for introducing foreign recombinant vectors into plant cells, and for obtaining plants that stably maintain and express the introduced gene. Such techniques include acceleration of genetic material coated onto microparticles directly into cells (U.S. Pat. No. 4,945,050 to Cornell and U.S. Pat. No. 5,141,131 to DowElanco). Plants may be transformed using Agrobacterium technology, see U.S. Pat. No. 5,177,010 to University of Toledo, U.S. Pat. No. 5,104,310 to Texas A&M, European Patent Application 0131624B1, European Patent Applications 120516, 159418B1 and 176,112 to Schilperoot, U.S. Pat. Nos. 5,149,645, 5,469,976, 5,464,763 and 4,940,838 and 4,693,976 to Schilperoot, European Patent Applications 116718, 290799, 320500 all to Max Planck, European Patent Applications 604662,627752 and U.S. Pat. No. 5,591,616 to Japan Tobacco, European Patent Applications 0267159, and 0292435 and U.S. Pat. No. 5,231,019 all to Ciba Geigy, U.S. Pat. Nos. 5,463,174 and 4,762,785 both to Calgene, and U.S. Pat. Nos. 5,004,863 and 5,159,135 both to Agracetus. Other transformation technology includes whiskers technology, see U.S. Pat. Nos. 5,302,523 and 5,464,765 both to Zeneca. Electroporation technology has also been used to transform plants, see WO 87/06614 to Boyce Thompson Institute, U.S. Pat. Nos. 5,472,869 and 5,384,253 both to Dekalb, WO9209696 and WO9321335 both to Plant Genetic Systems. All of these transformation patents and publications are incorporated by reference.

In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during dedifferentiation using appropriate techniques described herein.

Another variable is the choice of a selectable marker. The preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialophos); imidazolinones, sulfonylureas and triazolopyrimidine herbicides, such as chlorosulfuron; bromoxynil, dalapon and the like.

In addition to a selectable marker, it may be desirous to use a reporter gene. In some instances a reporter gene may be used without a selectable marker. Reporter genes are genes which are typically not present or expressed in the recipient organism or tissue. The reporter gene typically encodes for a protein which provides for some phenotypic change or enzymatic property. Examples of such genes are provided in K. Weising et al. Ann. Rev. Genetics, 22, 421 (1988), which is incorporated herein by reference. A preferred reporter gene is the beta-glucuronidase (GUS) gene.

Regardless of transformation technique, the gene encoding said maize PTE or maize OTE or fragments thereof in either the sense or antisense orientation or ribozymes thereof is preferably incorporated into a gene transfer vector adapted to express the said gene in a plant cell by including in the vector a plant promoter regulatory element. In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see PCT/US96/1682; WO 97/13402 published Apr. 17, 1997) and the like may be used. Plant promoter regulatory elements include, but are not limited to ribulose-1,6-bisphosphate (RUBP) carboxylase small subunit (ssu), beta-conglycinin promoter, phaseolin promoter, ADH promoter, heat-shock promoters and tissue specific promoters.

Promoter regulatory elements may also contain certain enhancer sequence elements that may improve the transcription efficiency. Typical enhancers include but are not limited to Adh-intron 1 and Adh-intron 6. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active during a certain stage of the plants' development as well as active in plant tissues and organs. Examples of such include but are not limited to pollen-specific, embryo specific, corn silk specific, cotton fiber specific, root specific, seed endosperm specific promoter regulatory elements and the like. Under certain circumstances it may be desirable to use an inducible promoter regulatory element, which is responsible for expression of genes in response to a specific signal, such as: physical stimulus (heat shock genes); light (RUBP carboxylase); hormone (Em); metabolites; and stress. Other desirable transcription and translation elements that function in plants may be used. Numerous plant-specific gene transfer vectors are known to the art.

One of the issues regarding exploiting transgenic plants having altered saturate levels is the expression of multiple chimeric genes at once. European Patent Application 0400246A1 describes transformation of two Bt genes in a plant; however, these could be any two genes or fragments thereof in either the sense or antisense orientation. The options could include but are not limited to genes and fragments encoding PTE in the antisense orientation with OTE in the sense orientations to create oils having unusually high levels of saturates, other oil modifying genes such as stearoyl-ACP desaturase and the like, as well as genes to impart insect control or herbicide resistance. Another way to produce a transgenic plant having multiple traits is to produce two plants, with each plant containing the oil modifying gene of interest. These plants can then be backcrossed using traditional plant breeding techniques to produce plants wherein phenotypic characteristics are related to the presence of more than one chimeric gene.

Plant oils can be further modified by altering the genes or fragments disclosed herein by mutagenesis. By performing mutagenesis on said genes, fragments, or plant cells containing said genes or fragments, the amino acid sequence of the protein can be altered. In some cases, these alterations will result in a protein having higher than normal levels of activity, thus increasing the rate of acyl-ACP hydrolysis. In other cases, the levels of activity will be decreased, resulting in decreased rates of acyl-ACP hydrolysis. Changes in acyl-ACP hydrolysis rates will alter saturate levels of oils within a cell, as disclosed herein. Therefore, one aspect of the present invention is mutagenesis of maize acyl-ACP thioesterase genes in plants.

A variety of methods can be used to mutagenize genes and nucleic acid fragments contained within plant cells. For example, chemical mutagenesis by treatment of pollen in paraffin oil or treatment of seed with ethyl methanesulfonate and the like is an efficient way to create maize mutants as described by Neuffer and Chang (1989) Science for Plant Breeding. Proc of the XII Congress of EUCARPIA, Gottingen, Germany 16:165–178; Neuffer (1982) Mutant induction in maize. In Sheridan WF (ed) Maize for Biological Research, Plant Mol. Biol. Assoc. Charlottesville, Va. pp.61–64; Neuffer (1994) Mutagenesis. In Freeling M and Walbot V. (eds) The Maize Handbook, Springer-Verlag, New York, N.Y. pp 212–219, and Wong et al., in U.S. Pat. Nos. 5,387,758, 5,545,821, and 5,434,283, which are incorporated herein by reference. The progeny of plants being mutagenized by chemical and other methods disclosed herein can be screened to select those plants having mutated maize acyl-ACP thioesterase genes. Mutations can be determined by gene sequencing methods and the like, as well as by screening for said plants having increased or decrease protein levels using antibodies and the like. Other methods include biochemical analysis of maize acyl-thioesterase proteins activity levels to screen for those having increased or decreased rates of acyl-ACP hydrolysis or for those having altered substrate specificities. Those plant having mutated acyl-ACP thioesterase proteins will then produce oils having altered saturate levels. Mutagenesis of acyl-ACP thioesterase genes can also be achieved through site directed integration as described by Offriga et al, (U.S. Pat. No. 5,501,967) and Hiei and Komari (U.S. Pat. No. 5,591,616).

The particular embodiments of this invention are further exemplified in the Examples. However, those skilled in the art will readily appreciate that the specific experiments detailed are only illustrative of the invention as described more fully in the claims which follow thereafter.

EXAMPLE 1

Isolation and Cloning of a cDNA Encoding Maize Palmitoyl-Acyl Carrier Protein Thioesterase A cDNA clone encoding maize PTE was obtained from a cDNA library derived from maize kernels of inbred CS608 (Mycogen Seeds, San Diego, Calif.) that had been grown in a greenhouse and hand pollinated. The cDNA library was prepared from said kernels harvested at 20 days after pollination, hereinafter 20-DAP. Embryos from said kernels were immediately collected, frozen on dry ice, and stored at −70° C. RNA was extracted by grinding to a fine powder said embryos (2.5 g) in liquid nitrogen. Ten mL of extraction buffer [50 mM Tris-HCl, pH 8.0, 4% para-amino salicyclic acid (Sigma Chemical Co., St. Louis, Mo.), 1% tri-isopropylnaphtalenesulfonic acid (Eastman Kodak Co., Rochester, N.Y.), 10 mM dithiothreitol (DTT) (Bethesda Research Labs, Gaithersburg, Md.) and 10 mM sodium meta-bisulfite (Sigma Chemical Co.)] was then added and the mixture was homogenized for 1 min using a TEKMAR TISSUMIZER (Tekmar Co., Cincinnati, Ohio). The homogenate was extracted with an equal volume of phenol equilibrated with 0.1 M Tris-HCl, pH 8.0. Organic and aqueous phases were separated by centrifugation at 4° C. The aqueous phase was removed and extracted with an equal volume of chloroform/octanol (24:1). The supernatant was then transferred, centrifuged, transferred again and a one-half volume of 7.5 M ammonium acetate (pH 8.0) was added. RNA was then precipitated on ice for 30 min.

Precipitated RNA was collected by centrifugation and dissolved in 1 mL of diethylpyrocarbonate-treated water (0.1% v/v), hereinafter DEPC-water. One-half volume of 7.5 M ammonium acetate (pH 8.0) and two volumes of 100% ethanol were added followed by RNA precipitation at −20° C. for 30 min. The precipitate was collected by centrifugation, washed in ice-cold 70% ethanol, air dried, and dissolved in 0.5 mL DEPC-treated water.

PolyA+ mRNA was purified on oligo dT-cellulose (Collaborative Biomedical Products, Bedford, Mass.) columns. Type 3 oligo-dT cellulose (0.1 g) was equilibrated in 5 mL of buffer 1 for 30 min, wherein buffer 1 is loading buffer with 0.5 M NaCl and loading buffer is 20 mM Tris-HCl, pH 7.6, 1 mM ethylenediaminetetraacetic acid (EDTA), and 0.1% sodium lauryl sulfate (SDS). The poured column was washed with 3 volumes of DEPC-water, 3 volumes of wash buffer [0.1 N NaOH, 5 mM EDTA], 3 volumes of DEPC-water, and 5 volumes of buffer 1. The dissolved RNA pellet was heated at 65° C. for 5 min, diluted 2× with buffer 2 [2× loading buffer] and then applied to the oligo-dT column. The flow through material was collected, reheated, and reapplied to the column. The column was then washed with 10 volumes of buffer 1 followed by 10 volumes of buffer 3 [loading buffer having 0.1 M NaCl]. PolyA$^+$ RNA was eluted with 3 volumes of elution buffer [10 mM Tris-HCl, pH 7.5, 1 mM EDTA, 0.05% SDS] and collected in 0.5 mL fractions. RNA fractions were combined, buffered to 0.3 M sodium acetate pH 5.2, and precipitated at −20° C. for 16 h after addition of 2.2 volumes of 100% ethanol. The precipitate was collected by centrifugation, washed with 70% ethanol, dried, and dissolved in 50 µL DEPC-treated water. This material was then repurified on a fresh oligo-dT column as described herein to produce highly-enriched polyA$^+$ mRNA. RNA concentrations were determined by measuring $OD_{260\ nm}$.

Five µg of polyA$^+$ RNA was converted to cDNA and cloned into the LAMBDA UNI-ZAP vector using the Lambda ZAP-cDNA synthesis and cloning kit according to the manufacturers protocols (Stratagene, La Jolla, Calif.). The resulting library had an original titer of $3.38 \times 10^{10}$ plaque forming units/mL (pfu/mL), greater than 95% recombinants and an average insert size of 1.35 kb. The cDNA library was amplified according to Sambrook et al., (Molecular Cloning, A Laboratory Manual, $2^{nd}$ Ed. (1989) Cold Spring Harbor Laboratory Press) and had a titer of $6.0 \times 10^6$ pfu/mL. Total library cDNA was batch rescued and isolated as follows: 5 mL of XL1 Blue E. coli cells (Stratagene) at $OD_{600\ nm}=1.0$ in 10 mM $MgSO_4$ were mixed with 8.3 µL ($5 \times 10^8$ pfu) of amplified embryo cDNA library phage-stock, and 100 µL EXASSIST helper phage (Stratagene) and incubated at 37° C. for 20 min. Twenty-five mL of TY medium, pH 7.8 [8.0 g/L tryptone, 5.0 g/L yeast extract, and 2.5 g/L NaCl] was added and cells were incubated at 37° C. for 3 h while shaking. Afterwards, the bacterial cells were heat killed at 68° C. for 15 min and the supernatant was recovered. Five hundred µL supernatant was mixed with 14.5 mL of SOLR cells (Stratagene) ($OD_{600\ nm}$=1.5), incubated at 37° C. for 15 min, added to 500 mL LB [10 g/L tryptone, 10 g/L NaCl, and 5 g/L yeast extract containing Ampicillin (50 µg/mL), and grown overnight. Afterwards, plasmid DNA was obtained by alkaline lysis/CsCl purification, according to Sambrook et al (Molecular Cloning, A Laboratory Manual, $2^{nd}$ Ed. (1989) Cold Spring Harbor Laboratory Press) and analyzed by agarose gel electrophoresis following digestion with EcoRI/XhoI. A smear ranging from 0.5 to 3.0 kb was observed following electrophoresis.

To isolate a clone encoding maize PTE, a DNA fragment was amplified using polymerase chain reaction technology, hereinafter PCR, to produce a probe which could be used to isolate a full length cDNA. A 5' primer with 256-fold degeneracy and a 3' primer with 16-fold degeneracy, entered herein as SEQ ID NO:1 and SEQ ID NO:2, respectively, were synthesized on an Applied Biosystems High-Throughput DNA Synthesizer Model 394 (Foster City, Calif.). Batch-rescued maize embryo cDNA was used as template. PCR amplification was performed as follows: 500 ng template DNA, 5 µL 10× reaction buffer, hereinafter 10× RB, [100 mM Tris-HCl pH 8.3, 500 mM KCl, 15 mM $MgCl_2$, 0.01% (w/v) gelatin], 5 µL of 2 mM deoxyribose nucleotides triphosphate (dNTPs), 50 pmole primers (SEQ ID NO:1 and SEQ ID NO:2), 2.5 units AMPLITAQ DNA Polymerase (Perkin-Elmer, Norwalk, Conn.) and water (total volume=50 µL). A DNA Thermal Cycler (Perkin-Elmer Cetus Model #480) was programmed as follows: 96° C. for 1 min; [94° C. (1 min), 55° C. (2 min), and 72° C. (3 min)] for forty cycles; followed by a 7 min (72° C.). A DNA product of 354 base pairs, hereinafter bp, was obtained, sequenced as described below, and entered herein as SEQ ID NO:3.

The DNA (SEQ ID NO:3) was blunt end cloned into the Sma I site of pBC phagemid vector (Stratagene) according to Wang et al., ((1994) BioTechniques 17:236–238). Blunt ending was done with T4 polymerase (New England BioLabs, Beverly, Mass.) followed by gel purification on a 1% preparative SEAKEM GTG agarose gel (FMC, Rockland, Me.) in TAE (0.04 M Tris-acetate pH 8.1, 0.002 M EDTA). DNA was extracted from agarose using QIAEX (Qiagen, Santa Clarita, Calif.) according to the manufacturer. Ligations and transformations were performed as described in Sambrook et al (Molecular Cloning, A Laboratory Manual, $2^{nd}$ Ed. (1989) Cold Spring Harbor Laboratory Press). Transformations were plated on LB-agar plates containing 35 µg/mL chloramphenicol and 50 µg/mL 5-bromo-4-chloro-3-indolyl-beta-D-galactopyranoside, hereinafter X-gal and allowed to grow overnight at 37° C. Colonies were isolated and grown in 5 mL of TB [1.2% tryptone, 2.4% yeast extract, 0.4% glycerol, 0.17 M $KH_2PO_4$, and 0.72 M $K_2HPO_4$] with 35 µg/mL chloramphenicol and plasmid DNA was extracted using PERFECT-PREP (5 Prime 3 Prime, Boulder, Colo.) according to the manufacturer. Plasmids were selected using restriction digest to screen for a 354 bp insert.

Recombinant clones were sequenced by dideoxy chain termination using PRISM AMPLITAQ READY REACTION DYEDEOXY Terminator cycle sequencing kit #401384 according to the manufacturer (Perkin-Elmer Applied Biosystems Division, Foster City, Calif.). Samples were run on an ABI373A automated DNA sequencer (Perkin-Elmer, Applied Biosystems Division). DNA sequence analysis of SEQ ID NO:3 was performed using MACVECTOR v. 4.1.4 (Oxford Molecular, Campbell, Ky.), which gave theoretical translations and alignments thus generating the amino acid sequence entered herein as SEQ ID NO:4.

A DNA fragment (SEQ ID NO:3) was used to screen the CS608 embryo cDNA library described herein to obtain full length clones encoding maize PTE. Probe DNA was obtained by growing a 30 mL culture of the pBC phagemid vector (Stratagene) containing the DNA fragment (SEQ ID NO:3) and was extracted using a MidiPrep Tip 500 (Qiagen). Twenty µg of plasmid DNA was digested with PstI and BamHI, run on a preparative 1% agarose gel, and the DNA fragment (SEQ ID NO:3) was excised and extracted with QIAEX (Qiagen, Inc.) according to manufacturer. An [$\alpha^{32}$P]-deoxyribocytosine triphosphate (dCTP)-labeled probe was generated using HIGHPRIME Random Labeling kit (Boehringer Mannheim, Indianapolis, Ind.) according to the manufacturer using 5 µL of [$\alpha^{32}$P]-dCTP (3000 Ci/mmole, 10 µCi/µL, DuPont, NEN Life Science Products, Boston, Mass.). Afterwards. the labeling reaction was applied to a NICK column (Pharmacia, Piscataway, N.J.) equilibrated with TE (10 mM Tris-HCl, pH 8.0, 1 mM EDTA). Labeled DNA was eluted with 2 volumes of TE (400 µL each). The probe was heat denatured before being added to hybridization buffer as described herein.

Methods for phage titering, plating, coring and rescuing are in the LAMBDA ZAP II Library (Stratagene) instruction manual and were used herein. The cDNA library described herein was plated (85,000 pfu/plate) on two 24.3×24.3 cm NUNC assay plates (Nunc Inc. Roskilde, Denmark). Duplicate phage lifts were taken from each plate using 0.45 µm MAGNAGRAPH-NT nylon membrane (MSI, Westborough, Mass.). Filters were as follows: 5 min with 0.5 N NaOH/1.5 M NaCl, pH 12.8; 5 min air dry; 5 min with 0.5 M Tris, pH 7.6/1.5 M NaCl; and 5 min air dry. DNA was cross-linked to the membranes while on filter paper dampened with 2×SSC [1×SSC is 0.15 M NaCl, 0.015 M sodium citrate, pH 7.0] using a STRATALINKER UV Crosslinker (Stratagene).

Filter prehybridization was performed at 42° C. in 150 mL hybridization buffer containing 50% (v/v) formamide, 6×SSC, 10× Denhardt's solution [1× Denhardt's solution is 0.02% Ficoll (Type 400, Pharmacia), 0.02% polyvinylpyrollidone, and 0.02% bovine serum albumin], 0.1% (w/v) SDS, and 200 µg/mL sheared and denatured salmon sperm DNA. After 3 h, used hybridization buffer was replaced with 100 mL of fresh hybridization buffer containing labeled probe (specific activity=5×10⁸ dpm/µg). Hybridization continued for 18–20 h at 42° C. with gentle rotation. Afterwards, filters were washed twice at 55–60° C. for 40 min. in 1 L of wash solution containing 0.2×SSC and 0.1% SDS. Filters were then exposed to Kodak XOMAT-AR Film (Eastman Kodak Company, Rochester, N.Y.) with intensifying screens (Lightening Plus, DuPont CRONEX, DuPont, Wilmington Del.) for 16 h at −70° C. Examination of films allowed the identification of positive plaques.

Positive plaques were cored out and stored in 1 mL SM buffer [5.8 g/L NaCl, 2 g/L $MgSO_4$, 20 mM Tris-HCl, pH 7.5, 5 mL/L of 2% (w/v) gelatin] with 50 µL chloroform. Phage were plated for secondary screening using 50 µL of a 1:1000 dilution of the primary phage stock. Positive plaques from the secondary screening were cored out and stored in 500 µL of SM buffer. Phage from these stocks were then plated for tertiary screenings using amounts ranging from 5

μL of undiluted secondary stock to 20 μL of 1:100 dilution in SM buffer. All subsequent hybridizations were performed as described above. Isolates were rescued into phagemid form according to the LAMBDA-ZAP II Library Instruction Manual (Stratagene). Rescued phagemid were plated by combining 200 μL SOLR cells (Stratagene) grown to $OD_{600nm}$=0.5 to 1.0 with 50–100 μL phagemid and incubating for 15 min at 37° C. Cells containing phagemid were streaked on LB agar containing Ampicillin (75 μg/mL) and grown overnight at 37° C. DNA was extracted from 4 mL liquid cultures grown overnight at 37° C. in TB [1.2% tryptone, 2.4% yeast extract, 0.4% glycerol, 0.17 M $KH_2PO_4$, and 0.72 M $K_2HPO_4$] using the alkaline lysis/polyethylene glycol protocol described in the PRISM READY REACTION DYEDEOXY Terminator Cycle Sequencing Kit Protocol#401388 Rev. B (Perkin-Elmer, Applied Biosystems Division)

The maize PTE cDNA contained 1777 bp (SEQ ID NO:5) and had an open reading frame of 1257 bp (SEQ ID NO:6) encoding a 419 amino acid protein (SEQ ID NO:7). The chloroplast transit peptide was deduced to include the first 90 amino acids (Tobin and Karlin-Neumann (1986) EMBO J. 5:9–13). The DNA sequence and amino acid sequence for the mature protein are entered herein as SEQ ID NO:8 and SEQ ID NO:9, respectively

EXAMPLE 2

Expression, Purification, and Analysis of E. coli Produced Maize Palmitoyl-Acyl Carrier Protein Thioesterase A vector to express mature maize PTE protein upon induction in E. coli (pDAB378) was constructed by ligating a DNA insert encoding the mature PTE peptide into the NdeI and XhoI sites of pET-26b (Novagen, Madison, Wis.). The insert (SEQ ID NO:12) was made using PCR techniques described herein as follows: a 5' primer (SEQ ID NO:10) and a 3' primer (SEQ ID NO:11) were used to add NdeI and XhoI sites, respectively, to the DNA (SEQ ID NO:5). The PCR reaction was as follows: 100 ng PTE phagemid cDNA (SEQ ID NO:5), 10 μL of 10×RB, 10 μL of 2 mM dNTP, 100 pmole primer (SEQ ID NO:10 and SEQ ID NO:11), and 5 units AMPLITAQ. Amplifications were performed using the GENEAMP PCR system 9600 (Perkin-Elmer) programmed with the following thermal profile: 96° C. (1 min); [94° C. (30 sec), 60° C. (30 sec), and 72° C. (45 sec)] for twenty cycles; followed by 7 min at 72° C. The PCR product (SEQ ID NO:12) was purified using a CENTRICON-100 concentrator (Amicon, Beverly, Mass.) according to the manufacturer.

The PCR product was cloned into pBC phagemid, (Stratagene) prior to being inserted into pET-26b (Novagene). The 1024 bp fragment (SEQ ID NO:12) was blunt ended using T4 polymerase and ligated into the SmaI site of pBC phagemid vector as described herein. Ligations were then transformed into competent E. coli DH5α cells (Gibco BRL, Gaithersburg, Md.) according to the manufacturer and plated on LB agar containing 35 μg/mL chloramphenicol and 50 μg/mL Xgal. Transformants were grown overnight in 4 mL of TB at 37° C. and DNA extractions were performed using the alkaline lysis mini-prep method according to Sambrook et al (Molecular Cloning, A Laboratory Manual, $2^{nd}$ Ed. (1989) Cold Spring Harbor Laboratories Press). The desired DNA was digested with NdeI and XhoI for 1 h at 37° C., isolated on a 1% preparative agarose gel and extracted using QIAEX (Qiagen). The NdeI/Xho I fragment, corresponding to nucleotides 9 to 1016 of SEQ ID NO:12, was then ligated into previously digested pET-26b (Novagen) using the RAPID DNA LIGATION kit (Boehringer Mannheim) according to the manufacture. Competent E. coli DH5α cells (GIBCO-BRL) were transformed with the ligation mixture grown overnight at 37° C. on LB agar plates having 30 μg/mL kanamycin. Analysis revealed a pET-26b vector having a 1008 bp DNA insert corresponding to bases 9 to 1016 of SEQ ID NO:12, and thus designated pDAB378.

For expression, BL21/pLys-S E. coli cells (Novagen, Madison, Wis.) were transformed with plasmid pDAB378 and transformants were selected on LB agar plates containing 30 μg/mL kanamycin and 35 μg/mL chloramphenicol. After growing overnight at 37° C., cells were scraped and placed into 25 mL LB broth containing 30 μg/mL kanamycin and 35 μg/mL chloramphenicol and allowed to grow to $OD_{600nm}$=0.6. Isopropyl-beta-D-thiogalactopyranoside, hereinafter IPTG, was added to a final concentration of 1 mM, and cells were incubated at 37° C. with shaking for 2.5 to 5 h. Cells were then pelleted at 2000 ×g and frozen on dry ice, thawed for 5 min at 37° C., frozen, and thawed again. Afterwards, the cells were resuspended in 0.5 mL E. coli lysis buffer [10 mM Tris-HCl, pH 8.0; 150 mM NaCl, 1 mM EDTA, 0.1% (v/v) Triton X-100] containing freshly added DNase and RNase (50 μg/mL each). Cells were held at 37° C. for 30 min followed by centrifugation at 15000 ×g for 15 min at 4° C. Resulting supernatants were stored at −20° C. until further purification.

Purification was initiated by desalting on a PD-10 column (Pharmacia) using buffer A [20 mM Tris-HCl, pH 7.0, and 0.4 mM DTT] and application to a MonoQ HR10/10 column (Pharmacia) equilibrated with buffer A. Bound proteins were eluted using a 0 to 0.5 M linear NaCl gradient buffer A over 30 min. Fractions were assayed for activity as described below and active fractions were combined, desalted on PD-10 columns (Pharmacia), and applied to a 1 mL ACP-Sepharose affinity column. [The ACP-Sepharose affinity column was made by covalently attaching ACP (Sigma Chemical Co.) to cyanogen bromide activated Sepharose CL4B beads according to manufacturer(Pharmacia)]. After washing with 0.1 M NaCl in buffer A, maize PTE was eluted with 1 M NaCl in buffer A.

For enzymatic analysis of E coli expressed maize PTE, substrates were made as follows: ACP (Sigma Chemical Co.) was further purified by three cycles of precipitation at pH 4.0 using 10% (v/v) acetic acid followed by resolubilization in 50 mM Tris-HCl, pH 8.0. Carbon-14 or tritium-labeled fatty acids (lauric, 12:0; myristic, 14:0; palmitic, 16:0; stearic, 18:0; and oleic, 18:1) were obtained from Amersham (Arlington Heights, Ill.) or NEN Research Products. Acyl-ACPs were synthesized and purified according to Rock et al., ((1981) Methods in Enzymology, 72:397–403). Thioesterase assays were conducted according to Ohlrogge et al., ((1978) Arch. Biochem. Biophys. 189:382–391) with slight modifications. A standard reaction contained 100 μM Tris-HCl, pH 8.0, 10 μM radio-labeled acyl-ACP (50–58 μCi/μmol), and enzyme in 50 μL. Reactions were conducted at 30° C. for 5 min and terminated with 200 μL of 10% (v/v) acetic acid. Free fatty acids were extracted twice with 1 mL hexane and the organic phases were combined for liquid scintillation counting. Protein concentrations were determined according to Bradford ((1976) Anal. Biochem. 189:248–254). Linear regressions were used for determination of kinetic constants from double reciprocal plots.

The substrate specificity of maize PTE expressed in *E. coli* was determined (Table 1). Expressed maize PTE had the highest level of activity towards 16:0-ACP, and secondly to 18:0-ACP.

TABLE 1

Substrate specificity ot partially purified maize PTE expressed in *E. coli*.

| Enzyme Substrate | Percent Relative Activity* |
| --- | --- |
| 12:0-ACP (Laurate) | 0.0 |
| 14:0-ACP (Myristate) | 16.0 |
| 16:0-ACP (Palmitate) | 100.0 |
| 18:0-ACP (Stearate) | 61.2 |
| 18:1-ACP (Oleate) | 40.4 |

*100% relative activity is equivalent to a specific activity of 2.1 units/mg protein where a unit is defined as the cleavage of 1 μmol/h free fatty acid at 30° C.

EXAMPLE 3

Construction of Sense and Antisense Maize Palmitoyl-Acyl Carrier Protein Thioesterase Plant Transformation Constructs Maize expression vectors containing the ubiquitin promoter regulatory element driving maize PTE expression were based on the plasmid pDAB439. Plasmid pDAB439 is a 7040 base pairs double stranded plant transformation vector composed of the following sequences in clockwise order. The plasmid backbone was derived from pUC19 (Yanish-Perron et al., (1985) Gene 33:103–119). Nucleotides 1 to 2252 of pDAB439 correspond to the reverse complement of nucleotides 435 to 2686 of pUC19. Nucleotides 2272 to 4264 of pDAB439 are the maize ubiquitin promoter and first intron, and were PCR amplified from genomic DNA of maize genotype B73 (Christensen et al., (1992) Plant Mol. Biol. 18: 675–689). Nucleotides 4309 to 4576 of pDAB439 corresponds to nucleotides 4420 to 4687 of plasmid pBI101 (Clontech, Palo Alto, Calif.) followed by the linker GG as nucleotides 4577 and 4578 of pDAB439. Nucleotides 4579 to 4743 of pDAB439 are the reverse complement of nucleotides 238–402 of pUC19. Nucleotides 4808–5416 of pDAB439 comprise the double enhanced 35S promoter, with nucleotides 5070 to 5416 corresponding to nucleotides 7093 to 7439 of the Cauliflower Mosaic Virus genome (Franck et al., (1980) Cell 21:285–294). Nucleotides 4808 to 5061 of pDAB439 are a duplication of nucleotides 5068 to 5321. Nucleotides 5437 to 5547 of pDAB439 correspond to nucleotides 167 to 277 of the Maize Streak Virus genome (Mullineaux et al., (1984) EMBO J. 3:3063–3068). Nucleotides 5548 to 5764 of pDAB439 correspond to the modified first intron of the maize alcohol dehydrogenase gene (Adh1-S) (Dennis et al., (1984) Nucleic Acids Res. 12:3983–4000). The modification resulted in removal of 343 nucleotides (bases 1313 to 1656) with bases 1222 to 1312 (intron 5' end) and nucleotides 1657 to 1775 (intron 3' end) of the maize Adh1-S gene remaining. Nucleotides 5765 to 5802 of pDAB439 correspond to Maize Streak Virus (MSV) nucleotides 278 to 312, followed by the linker sequence CAG. Both sections of the Maize Streak Virus, hereinafter MSV, sequence comprise the untranslated leader of the MSV coat protein V2 gene, and are interrupted in plasmid pDAB439 by the modified Adh1 intron. Nucleotides 5803 to 6359 of plasmid pDAB439 corresponds to nucleotides 29 to 585 of the phosphinotricin acetyl transferase (BAR) gene of Streptomyces hygroscopicus (White et al., (1989) Nucleic Acids Res. 18:1062). To facilitate cloning, nucleotides 34 and 575 of the published sequence were changed from A to G and G to A, respectively. This sequence serves as the selectable marker in plant cells. Nucleotides 6365 to 6628 of pDAB439 correspond to nucleotides 4420 to 4683 of plasmid pBI101 (Clontech, Palo Alto, Calif.). Nucleotides 6640 to 7040 of pDAB439 correspond to nucleotides 284 to 684 of pUC19.

The plasmid pDAB374 is essentially plasmid pDAB439 with the maize PTE gene in the antisense orientation relative to the ubiquitin promoter. PCR primers according to SEQ ID NO:14 and SEQ ID NO:15 were used to add unique Sfi I sites to the 3' and 5' ends, respectively, of SEQ ID NO:5 as disclosed herein. The 1302 bp DNA fragment(SEQ ID NO:16), created by PCR techniques as described herein, was digested with Sfi I and ligated into pDAB439 between the two SfiI sites at nucleotides 4270 to 4301 to create pDAB374. The ligation reaction and transformation were performed as disclosed herein. Transformants were screened through restriction analysis for the 1286 bp insert corresponding to bases 9 to 1294 of SEQ ID NO:16, and an isolate was selected for sequencing. Sequencing was performed as disclosed herein.

The plasmid pDAB376 is essentially plasmid pDAB439 with a gene corresponding to maize PTE cDNA in the sense orientation relative to the ubiquitin promoter. Unique Sfi I sites were incorporated on the 5' and 3' end of the maize PTE cDNA (SEQ ID NO:5) using primers entered herein as SEQ ID NO:17 and SEQ ID NO:18, respectively. PCR amplification and DNA sequencing was performed as described previously with the new DNA sequence entered herein as SEQ ID NO:19. This fragment (SEQ ID NO:19) was digested with Sfi I and cloned into plasmid pDAB439, as previously described, to create plasmid pDAB376.

EXAMPLE 4

Isolation and Cloning of the Maize Globulin Promoter

The maize globulin promoter (Belanger et al., (1989) Plant Physiol. 91:636–643) was PCR amplified from genomic DNA isolated from lyophilized leaf tissue of six week old plants from two inbred lines, CS405 and OQ603 (Mycogen Seeds) as described by Saghai-Maroof et al. ((1984) Proceed. National Acad. Sci. USA 81:8014–8018). The forward PCR primer (SEQ ID NO:20) introduced 5' XbaI and HindIII restriction sites. The reverse primer (SEQ ID NO:21) introduced an NcoI site encoding an ATG start codon allowing gene fusion in the correct translational reading frame. PCR reactions were performed using the EXPAND Long Template PCR System (Boehringer Mannheim) as according to the manufacturer. Amplifications were cycled using the following profile: [94° C. (30 sec), 56° C. (2 min), 68° C. (3 min)] for 30 cycles. Maize genomic DNA was used as template. Amplification products were purified by electrophoresis on a 1.0% agarose gel, purified using QIAEX II (Qiagen), and ligated into vector pCR2.1 using the ORIGINAL TA Cloning Kit (Invitrogen Corporation, San Diego, Calif.). Recombinant plasmids were transformed into INVαF' *E. coli* competent cells (Invitrogen) and selected on Luria agar (Gibco-BRL) containing 75 mg/L Ampicillin and 40 μL/plate of X-gal (Boehringer Mannheim). Plasmid DNAs were purified using WIZARD PLUS Miniprep DNA Purification System (Promega, Madison, Wis.). The resultant plasmids, p58-6 and p59-6, contained globulin promoter DNA corresponding to SEQ ID NO:22 and SEQ ID NO:23, respectively.

The globulin promoter fragments were fused to the GUS coding region to create the plasmids pGGN61-1 and pGGN62-2. Plasmid pGGN62-2 is a 6321 base pair plasmid comprised of the following sequences: nucleotides 1 to 1257 correspond to nucleotides 4 to 1260 of SEQ ID NO:22; nucleotides 1258 to 3399 correspond to bases 898 to 3039 of pBI221 (Clontech) in which eight bases of the beta-glucuronidase gene, hereinafter GUS gene, were reengineered to contain an NcoI site at the ATG start codon to facilitate cloning and maintain sequences optimal for translation initiation. This results in the first eight base pairs of the GUS gene have the sequence CCATGGTC resulting in an amino acid sequence change from Met Leu to Met Val. The remaining nucleotides in pGGN62-2 (3400 to 6321) correspond to nucleotides 1 to 2916 of pBLUESCRIPT SK- (Stratagene) with nucleotide 1 being defined as the first A residue of the unique HindIII site and proceeding clockwise towards the XhoI site. The six base difference in the number of bases is due to base deletions in the published sequence from 232 to 235 and 663 to 664. Plasmid pGGN61-1 (6510 base pairs) was as described above except the globulin promoter corresponds to bases 4 to 1449 of SEQ ID NO:23.

EXAMPLE 5

Transient and Stable Testing of Globulin Constructs

The two plasmids, pGGN61-1 and pGGN62-2, were tested for transient expression in immature zygotic embryos using the proprietary inbred line, OQ414 (Mycogen Seeds). For testing expression, embryos 12–14 DAP were isolated and cultured on 15Ag10 medium (Chu, C. (1978) The N6 medium and its application to anther culture of cereal crops. Proc. Symp. Plant Tissue Culture, Peking Press, 43–56) for 1–2 days before DNA delivery. Medium 15Ag10 consisted of N6 basal salts and vitamins, Fe-EDTA, 20 g/L sucrose, 2.9 g/L L-proline, 100 mg/L enzymatic casein hydrolysate (ECH), 1 mg/L 2,4-dichloro-phenoxyacetic acid (2,4-D), 10 mg/L silver nitrate, and 2.5 g/L GELRITE (Schweizerhall, South Plainfield, N.J.) at pH 5.8. For blasting, ca. 12 embryos were arranged in ca. 1 cm$^2$ target area on blasting medium and covered with a 230 $\mu$m stainless steel screen. Blasting medium differed from 15Ag10 in that it contained 690 mg/L L-proline, 2% agar and no silver nitrate.

For blasting 140 $\mu$g of plasmid DNA was precipitated onto 60 mg of alcohol-rinsed, spherical gold particles (1.0 $\mu$m diameter) by adding 74 $\mu$L of 2.5M CaCl$_2$ and 30 $\mu$L of 0.1 M spermidine (free base) to 300 $\mu$L of plasmid DNA. The solution was immediately vortexed and the DNA-coated gold particles were allowed to settle. The resulting clear supernatant was removed and the gold particles were resuspended in 1 mL of absolute ethanol. This suspension was diluted with absolute ethanol to obtain 15 mg DNA-coated gold/ mL.

Helium blasting accelerated suspended DNA-coated gold particles towards and into the prepared tissue targets. The device used was an earlier prototype of that described in U.S. Pat. No. 5,141,131 which is incorporated herein by reference. Tissues were covered with a stainless steel screen (230 $\mu$m openings) and placed under a partial vacuum of 25 inches of Hg in the device chamber. The DNA-coated gold particles were further diluted 1:1 with absolute ethanol prior to blasting and were accelerated at the embryo target once using a helium pressure of 1500 psi, with each blast delivering 20 $\mu$L of the DNA/gold suspension.

One day after blasting, embryos were subjected to histochemical GUS analysis (Jefferson (1987) Plant Mol. Biol. Rep. 5:387–405). Briefly, tissues were placed in 24-well microtiter plates (Corning) containing 500 $\mu$L of assay buffer [0.1 M sodium phosphate, pH 8.0, 0.5 mM potassium ferricyanide, 0.5 mM potassium ferrocyanide, 10 mM sodium EDTA, 1.9 mM 5-bromo-4-chloro-3-indolyl-beta-D-glucuronide, and 0.06% TRITON X-100] per well and incubated in the dark for 1–2 days at 37° C. before analysis. GUS expression units, visualized as blue spots per target area, were counted under a microscope and are presented in the Table 2. A target area was defined as 1 cm$^2$ and equal to ca. 12 embryos. Both plasmids resulted in high levels of transient expression as shown in Table 2.

TABLE 2

| Transient GUS expression of two globulin constructs in immature embryos of maize. | | | |
|---|---|---|---|
| Construct | Corn Line | GUS Units/Target | Promoter SEQ ID |
| pGGN61-1 | OQ603 | 232 | SEQ ID NO:23 |
| pGGN62-2 | CS405 | 349 | SEQ ID NO:22 |

The globulin promoter from pGGN62-2 (SEQ ID NO:22) was chosen for stable maize analysis. Stably transformed maize lines were generated simultaneously blasting pDAB308 and pGGN62-2 into maize tissue.

Plasmid pDAB308 is a 4496 base pair plasmid having the following: position 1 corresponds to base 441 of pUC19 (Messing, J. (1983) in "Methods in Enzymology" (Wu, R. et al., Eds) 101:20–78) and is the base after the final C residue of the SphI site. Reading on the strand contiguous to the LacZ gene coding strand, which corresponds to nucleotides 4468 to 4496 and 1851 to 2105 of plasmid of pDAB308. Nucleotides 20 to 271 of plasmid pDAB308 correspond 7093 to 7344 of the Cauliflower Mosaic Virus CabbS strain, hereinafter CaMV, (Franck, et al., (1980) Cell 21:285–294); nucleotides 280 to 626 of plasmid pDAB308 correspond to nucleotides 7093 to 7439 of CaMV; nucleotides 647 to 666 of plasmid pDAB308 correspond to nucleotides 167 to 186 of Maize Streak Virus, hereinafter MSV, (Mullineaux, et al., (1984) EMBO J. 3:3063–3068); nucleotides 667 to 756 of plasmid pDAB308 correspond to nucleotides 188 to 277 of MSV; nucleotides 757 to 849 of plasmid pDAB308 correspond to bases CA followed by nucleotides 120 to 210 of maize alcohol dehydrogenase 1S, hereinafter Adh1, (Dennis, et al.,(1984) Nucl. Acids Res. 12:3983–4000) containing parts of exon 1 and intron 1; nucleotides 850 to 967 of plasmid pDAB308 correspond to nucleotides 555 to 672 of Adh1 containing parts of intron 1 and exon 2; nucleotides 978 to 1017 of plasmid pDAB308 correspond to nucleotides 278 to 317 of MSV; nucleotides 1018 to 1566 of plasmid pDAB308 correspond to a modified BAR coding region from pIJ4104 (White et al., (1990) Nucl. Acids. Res. 18:1062) having the AGC (serine) codon in the second position replaced by GCC (alanine) and nucleotide 546 changed from G to A; nucleotides 1591 to 1847 of plasmid pDAB308 correspond to nucleotides 1298 to 1554 of nopaline synthase (DePicker, et al.,(1982) J. Molec. Appl. Genet. 1:561–573); and nucleotides 1848 to 4496 of plasmid pDAB308 correspond to the base G followed by the rest of pUC 19.

Another plasmid was constructed to eliminate the need for cobombarding two plasmids. Plasmid pGGN367 contains both the globulin-GUS-NOS fusion as well as the BAR gene for BASTA resistance. The globulin promoter-GUS-NOS fusion from pGGN62-2 was liberated using HindIII and ligated into pDAB367 to create pGGN367.

A description of pDAB367, a 4565 bp plasmid, follows: nucleotides 1 of plasmid pDAB367 corresponds to base 441 of pUC 19 beginning with the base after the final C residue of the Sph I site (Messing, J. (1983) in "Methods in Enzymology" (Wu, R. et al., Eds) 101:20–78) and reading on the strand contiguous to the LacZ gene coding strand; nucleotides 90 to 341 of plasmid pDAB367 correspond to nucleotides 7093 to 7344 of CaMV DNA (Franck, et al., (1980) Cell 21:285–294.); nucleotides 350 to 696 of plasmid pDAB367 correspond to nucleotides 7093 to 7439 of CaMV; nucleotides 717 to 736 of plasmid pDAB367 correspond to nucleotides 167 to 186 of MSV (Mullineaux et al., (1984) EMBO J. 3:3063–3068); nucleotides 737 to 826 of plasmid pDAB367 correspond to nucleotides 188 to 277 of MSV (Mullineaux, et. al.); nucleotides 827 to 919 of plasmid pDAB367 correspond to bases CA, followed by nucleotides 120 to 210 of maize Adh 1S containing parts of exon 1 and intron 1 (Dennis et al., (1984) Nucl. Acids Res. 12:3983–4000); nucleotides 920 to 1037 of plasmid pDAB367 correspond to nucleotides 555 to 672 containing parts of Adh 1S intron 1 and exon 2; nucleotides 1048 to 1087 of plasmid pDAB367 correspond to nucleotides 278 to 317 of MSV. This promoter region, comprised of the 35S promoter with two enhancer fragments, MSV leader and modified Adh1 intron, is hereinafter referred to as 35T. Nucleotides 1088 to 1633 of plasmid pDAB367 correspond to a modified BAR coding region of pIJ4104 (White et al., (1990) Nucl. Acids. Res. 18:1062) having the Ser codon (AGC) in the second position replaced by an Ala codon (GCC), and nucleotide 546 of the coding region changed from G to A. Nucleotides 1661 to 1917 of plasmid pDAB367 correspond to nucleotides 1298 to 1554 of NOS [DePicker et al (1982) J. Molec. Appl. Genet. 1:561–573); and nucleotides 1918 to 4556 of plasmid pDAB367 correspond to a G base followed by the rest of the pUC19 sequence.

To produce stable transgenics callus targets were blasted as described above. Type II callus cultures were initiated from immature zygotic embryos of the genotype "Hi-II." (Armstrong et al, (1991) Maize Cooperation Newsletter, pp.92–93). Embryos were isolated from greenhouse-grown ears from crosses between Hi-II parent A and Hi-II parent B or F2 embryos derived from a self- or sib-pollination of a Hi-II plant. Immature embryos (1.5 to 3.5 mm) were cultured on initiation medium consisting of N6 salts and vitamins (Chu et al, (1978) The N6 medium and its application to anther culture of cereal crops. Proc. Symp. Plant Tissue Culture, Peking Press, 43–56) 1.0 mg/L 2,4-D, 25 mM L-proline, 100 mg/L casein hydrolysate, 10 mg/L $AgNO_3$, 2.5 g/L GELRITE, and 20 g/L sucrose, with a pH of 5.8. Selection for Type II callus took place for ca. 2–12 weeks. After four weeks callus was subcultured onto maintenance medium (initiation medium in which $AgNO_3$ was omitted and L-proline was reduced to 6 mM).

In some cases, callus were transferred to embryo maturation media with and without abscisic acid, hereafter ABA, for development of somatic embryos using the procedure described herein. After 14 days of culture, somatic embryos of different transgenic lines were shown to be positive for UGS expression when tested using the histochemical GUS assay (Jefferson, 1987 Plant Mol. Biol. Rep. 5:387–405). In some cases, high levels of expression, as indicated by the intense blue staining throughout the embryo, were observed For further analysis, plants were regenerated from the GUS-positive lines described herein. GUS positive callus tissue was divided into small pieces and transferred to selection medium (maintenance medium lacking casein hydrolysate and L-proline plus 30 mg/L BASTA (Agrevo, Inc.). Every 4 weeks for 3 months, the tissues were non-selectively transferred to fresh selection medium. After 6 weeks and up to 20 weeks, callus sectors found proliferating against a background of growth-inhibited tissue were removed and isolated. The resulting BASTA-resistant tissue was subcultured biweekly onto fresh selection medium.

Stably transformed callus lines positive for the gene of interest as determined by Southern analysis (described herein) were selected for regeneration (308/Glb1-11, 308/Glb1-85, GGN367-43, GGN367-59). R0 plants (defined as primary regenerates that were regenerated from the stably transformed callus tissue) were grown to maturity and controlled pollinations (self, sib, or cross with CQ806) were made. Histochemical analysis of leaf, root, anthers, pollen, and endosperm from said plants was negative. However, embryos from the seed produce by said plant exhibited high levels of GUS expression. Quantitative GUS expression in embryos at 20 DAP of these two events is shown below in Table 3.

Tissues were prepared for quantitative GUS analysis using the procedure that follows. Leaf tissue from two Southern-positive R1 transgenic plants at the six leaf stage were collected, frozen in liquid nitrogen and ground to a fine powder with a mortar and pestle. Samples were weighed and four-fold (v/w) GUS-LIGHT (Tropix, Bedford, Mass.) extraction buffer with 20% glycerol (v/v) was added to each sample. Samples were homogenized for 25 sec and maintained on ice throughout the extraction protocol. Samples were clarified by centrifugation 10,000×g for 10 min at 5° C. One mL of supernatant was transferred to sterile microfuge tubes, re-centrifuged at full speed (Eppendorf Centrifuge Model 5415; Brinkman Instrument Co., Westbury, N.Y.), and stored at −70° C. until analysis.

Embryos from plants self-crossed and out-crossed to CQ806 at 20 DAP were examined quantitatively for GUS expression. Samples were prepared as described herein except that histochemically positive(about 6 embryos) and negative tissues were pooled separately. Final supernatants of the positive samples were diluted 50-fold in extraction buffer. GUS activity in stably transformed plant tissues was measured using the GUS-LIGHT assay kit (Tropix) and an automatic luminescence photometer (Model 1251 Luminometer and Model 1291 Dispenser, Bio-Orbit, Finland). Five $\mu L$ of extract was added to 200 $\mu L$ of GUS-LIGHT reaction buffer (Tropix). Samples, which were prepared in duplicate, were incubated at 21° C. for 1 h in the dark. As each vial entered the measuring chamber, 300 $\mu L$ of GUS-LIGHT Light Emission Accelerator Buffer (Tropix) was added and luminescence was measured over a 5-sec integration period. Two blank reactions, which included 5 $\mu L$ of GUS extraction buffer, were run at the beginning and end of the series. Commercially available GUS (Sigma Chemical Co.) was used to confirm equipment sensitivity and reagents quality. GUS readings in relative light units, hereinafter RLU, were corrected for the blank average.

TABLE 3

Quantitative GUS analysis of R1 leaf tissue

| R1 Line | Average RLU/Leaves | Standard Deviation |
|---|---|---|
| GPN35[a] (negative control) | 50.9 | 0.2 |
| 35T07[b] (positive control) | 10630.0 | 254.5 |

TABLE 3-continued

Quantitative GUS analysis of R1 leaf tissue

| R1 Line | Average RLU/Leaves | Standard Deviation |
|---|---|---|
| 308/Glb1-11-10-27 | 66.5 | 0.7 |
| 308/Glb1-85-04-09 | 55.9 | 2.5 |

[a]GPN35 is a plant line transformed with a plasmid containing a seed specific maize globulin promoter driving the palmitoyl thioesterase gene (see Example 7). The GUS coding region is not on this plasmid and therefore transformants should be negative for GUS activity.
[b]35T07 is a plant line transformed with a plasmid that is essentially pDAB308 (see Example 5) with the addition of the GUS and Nos sequences from pBI221 (Clontech) driven by the CaMV promoter/MSV leader/Adh intron described previously.

No statistically significant expression was observed in the leaves of transgenic lines Glb1-11-10-27 or Glb1-85-04-09 (Table 3). In addition, seed embryos from lines Glb-11 and Glb1-85 has GUS activity levels that were on average 144-fold and 8087-fold higher, respectively, than negative controls, as shown in Table 4. These results further corroborated the fact that high embryo specific expression can be achieved in maize embryos when using the Globulin promoter (SEQ ID NO:22).

TABLE 4

Quantitative GUS analysis of 20 DAP embryos

| Transgenic Line[a] | Histocheznical Analysis | Relative Light Units | Fold Increase over Control |
|---|---|---|---|
| 308-Glb1-11-10[b] | neg | 1045 | — |
| 308-Glb1-11-10 | pos | 217188 | 207 |
| 308-Glb1-11-10 | pos | 118651 | 81 |
| 308-G1b1-85-02[b] | neg | 88 | — |
| 308-Glb1-85-02 | pos | 711726 | 8087 |

[a]Different plants from the segregating line were used.
[b]The plants were negative for the GUS gene due to segregation and were therefore used as negative controls for their respective transformed lines.

EXAMPLE 6

Southern Analysis of Transformed Callus and Plant Tissues

BASTA resistant lines transformed with various plasmids were characterized by Southern analysis to confirm the presence of the transgene using a DNA probe specific for the coding region of the gene of interest. DNA from both callus and leaf material was analyzed.

For callus, the material was soaked in distilled water for 30 min. and transferred to a new petri dish prior to lyophilization. Leaf material from plants was harvested at the 6–8 leaf stage. Genomic DNA was prepared from lyophilized tissue as described by Saghai-Maroof et. al. ((1984) Proceed. Nat. Acad. Sci. USA 81:8014–8018). Eight μg of each DNA was digested with the restriction enzyme(s) specific for each plasmid construct using conditions suggested by the manufacturer (Bethesda Research Laboratory) and separated by electrophoresis on a 0.8% agarose gel. The DNA was then blotted onto nylon membranes as described by Southern ((1975) J. Mol. Biol., 98:503–517). The radioactive probe was then hybridized to the genomic DNA on the blots in 45 mL of minimal hybridization buffer [10% polyethylene glycol, 7% sodium dodecyl sulfate, 0.6×SSC, 10 mM sodium phosphate, 5 mM EDTA and 100 μg/mL denatured salmon sperm DNA] overnight at 60° C. After hybridization, blots were washed at 60° C. in 0.25×SSC and 0.2% SDS for 45 min., blotted dry and exposed to XAR-5 film (Kodak) overnight on two intensifying screens (DuPont).

EXAMPLE 7

Cloning of the Maize PTE Gene with the Globulin Promoter

For cloning of the maize PTE gene 3' to the globulin promoter, an Nco I site within the maize PTE gene was removed and 5' Nco I and 3' Xho I sites were added. The internal Nco I site was removed using splice overlap extension, hereinafter SOEing, (Horton et al., (1989) Gene 77:61–68). Primers were designed to convert a cytosine (nt. 1239 of SEQ ID NO:5) to a guanine residue which would conserve the amino acid sequence of the protein but alter the restriction enzyme recognition site. The gene was amplified in two segments as follows: a primer (SEQ ID NO:24) was used to add an Nco I site to the 5' end of the gene and another primer (SEQ ID NO:25) was used as the sense primer to alter the internal Nco I site; another primer (SEQ ID NO:26) was also used to alter the internal Nco I site; and another primer (SEQ ID NO:11) was used to add an Xho I site onto the 3' end of the gene.

Using conditions described previously, two PCR reactions were performed. The first used 80 ng cDNA (SEQ ID NO:5) and primer identified as SEQ ID NO:24 and SEQ ID NO:26, with the DNA product entered herein as SEQ ID NO:27. The second reaction 80 ng cDNA (SEQ ID NO:5) with primers identified as SEQ ID NO:25 and SEQ ID NO:11 with the DNA product entered herein as SEQ ID NO:28. PCR products were purified on an agarose gel and the DNA extracted with QIAEX (Qiagen) as previously described. SOEing reactions were performed using the PCR products (SEQ ID NO:27 and SEQ ID NO:28) combined with flanking primers (SEQ ID NO:24 and SEQ ID NO:11) using reaction conditions described previously. The final PCR product (SEQ ID NO:29) was cloned directly into the TA CLONING vector (Invitrogen) according to manufacturers instructions. After ligation and transformation, colonies were selected and the plasmid having the insert disclosed as SEQ ID NO:29 was sequenced as described previously. The Nco I "cured" PTE sequence was liberated by restriction digest with Nco I and Xho I.

A Kpn I site was introduced onto the 5' end of the globulin promoter (SEQ ID NO: 22) by PCR amplification as described previously using a 5' primer (SEQ ID NO: 30) and a 3' primer (SEQ ID NO: 21). The DNA sequence generated is entered herein as SEQ ID NO: 31. The globulin promoter and the PTE coding region were assembled into a vector named pGPN88-1.

Plasmid pGPN88-1 and contains the following components: nucleotides 1 to 12 is a linker corresponding to bases 1–12 of pUC18 if nucleotide 1 of pUC18 is defined as the G residue of the restriction site EcoR1 and moving in a clockwise direction toward the sense strand coding for ampicillin resistance (Messing, J. et al (1983) Gene 26: 101–106); nucleotides 13 to 1263 are the globulin promoter corresponding to bases 5 to 1255 of SEQ ID NO:31; nucleotides 1264 to 2529 of plasmid pGPN88-1 encode the maize PTE gene corresponding to nucleotides 3 to 1268 of SEQ ID NO:29; nucleotides 2530 to 2545 comprise a linker; nucleotides 2546 to 2798 of plasmid pGPN88-1 are the NOS untranslated 3' region (DePicker et. al., (1982) J. Molec. Appl. Genet. 1:561–573); nucleotides 2799 to 2809 of plasmid pGPN88-1 comprise a linker nucleotides 2810 to 3213 of plasmid pGPN88-1 correspond to bases 1–404 of pUC18 ; nucleotides 3214 to 3223 of plasmid pGPN88-1 comprise a linker; and nucleotides 3224 to 5454 of plasmid pGPN88-1 correspond to nucleotides 405–2635 of pUC18.

EXAMPLE 8

Production and Regeneration of Transgenic PTE Maize Isolates

For the production of transgenic corn plants, Type II callus cultures were initiated as described herein. Particle preparation was performed as previously described. Afterwards, ca. 600 mg of embryogenic callus tissue was spread over the surface of Type II callus maintenance medium as described herein lacking casein hydrolysate and L-proline, but supplemented with 0.2 M sorbitol and 0.2 M mannitol as an osmoticum. Following a 4–16 h pre-treatment, tissue was transferred to culture dishes containing blasting medium (osmotic media solidified with 20 g/L tissue culture agar (JRH Biosciences, Lenexa, KS) instead of 7 g/L GELRITE (Schweizerhall). Helium blasting was performed as described herein. Immediately post-blasting, the tissue was transferred to osmotic media for a 16–24 h recovery period. Afterwards, the tissue was divided into small pieces and transferred to selection medium (maintenance medium lacking casein hydrolysate and L-proline but having 30 mg/L BASTA (Agrevo)). Every four weeks for 3 months, tissue pieces were non-selectively transferred to fresh selection medium. After 6 weeks and up to 20 weeks, callus sectors found proliferating against a background of growth-inhibited tissue were removed and isolated. The resulting BASTA-resistant tissue was subcultured biweekly onto fresh selection medium.

Regeneration was initiated by transferring callus tissue to cytokinin-based induction medium, which consisted of Murashige and Skoog salts, hereinafter MS salts, and vitamins (Murashige and Skoog, (1962) Physiol. Plant. 15: 473–497) 30 g/L sucrose, 100 mg/L myo-inositol, 30 g/L mannitol, 5 mg/L 6-benzylaminopurine, hereinafter BAP, 0.025 mg/L 2,4-D, 30 mg/L BASTA, and 2.5 g/L GELRITE (Schweizerhall) at pH 5.7. The cultures were placed in low light (125 ft-candles) for one week followed by one week in high light (325 ft-candles). Following a two week induction period, tissue was non-selectively transferred to hormone-free regeneration medium, which was identical to the induction medium except that it lacked 2,4-D and BAP, and was kept in high light. Small (1.5–3 cm) plantlets were removed and placed in 150×25 mm culture tubes containing SH medium (SH salts and vitamins (Schenk and Hildebrandt, (1972) Can. J. Bot. 50:199–204), 10 g/L sucrose, 100 mg/L myo-inositol, 5 mL/L FeEDTA, and 2.5 g/L GELRITE (Schweizerhall), pH 5.8). Plantlets were transferred to 10 cm pots containing approximately 0.1 kg of METRO-MIX 360 (The Scotts Co. Marysville, Ohio) in the greenhouse as soon as they exhibited growth and developed a sufficient root system. They were grown with a 16 h photoperiod supplemented by a combination of high pressure sodium and metal halide lamps, and were watered as needed with a combination of three independent Peters Excel fertilizer formulations (Grace-Sierra Horticultural Products Company, Milpitas, Calif.). At the 3–5 leaf stage, plants were transferred to five gallon pots containing approximately 4 kg METRO-MIX 360.

Primary regenerants (R1 plants) were self- or sib-pollinated when possible after an additional 6–10 weeks in five gallon pots, and R1 seed was collected at 40–45 days post-pollination. When self- or sib-pollinations were not possible, plants were outcrossed to elite inbreds. $R_1$ seed were analyzed to identify kernels having the phenotype of interest. This was accomplished by sampling a small piece of the embryo and salvaging the remaining seed for planting. These kernels were then planted in five gallon pots to obtain R1 plants which were either selfed or outcrossed to elite inbreds to produce $R_2$ seed. R2 seed was analyzed for presence of the desired trait. In all cases segregation of the trait was observed. This can be explained by segregation of the gene of interest in this generation. Most R1 lines are hemizygous for the transgene and therefore do not transmit the transgene to all progeny. In analyses of R2 seed for fatty acid modification, alterations of enzyme activity or mRNA levels, seed from untransformed lines , or transformed lines not carrying the gene of interest (identified by Southern analysis of the R1 plants) were included in the analysis as controls. When appropriate controls were not available, seed segregating for the trait of interest was compared. Seeds showing alterations of the fatty acid phenotype were compared to seeds displaying normal fatty acid profile from the same experiment.

Modification of fatty acid composition was achieved using different promoter-gene fusions. The ubiquitin promoter was used to achieve constitutive changes in fatty acid composition and thus saturate levels. Two ubiquitin-PTE plasmids described previously, plasmids pDAB374 and pDAB376, were blasted into embryogenic Type II callus cultures. BASTA-resistant isolates were recovered from selection, although additional isolates could have been recovered if multiple isolates would have been selected per plate.

Following Southern and gas chromatography/fatty acid methyl ester, hereinafter GC/FAME, analyses, as described herein, positive transgenic lines were identified and transferred to regeneration media. R0 plants were produced from the above mentioned lines, pollinations were made and produced seed. Some total pollinations involved self- or sib-pollinations and others were crosses using donor pollen from elite inbreds. $R_1$ seed from different $R_0$ lines was collected.

Seed specific modification of the fatty acid composition was achieved using the globulin promoter. The globulin PTE plasmid was co-bombarded with plasmid pDAB308 into embryogenic Type II callus, placed in selection, and BASTA-resistant isolates were obtained. Southern and GC/FAME analysis was used to identify transgenic lines of interest. These were transferred to regeneration media and R0 plants. R0 plants were then pollinated to produce $R_1$ seed.

$R_1$ seed was analyzed for levels of saturated fatty acids, palmitate (16:0) and stearate (18:0), using GC/FAME as described herein. Several kernels from one of the lines showed reduced 16:0 levels compared to control. Kernels showing reduced 16:0 levels were pre-germinated on moistened seed paper in the presence of a fungicide seed treatment. Germinated seedlings were transplanted in five gallon pots and allowed to grow in the greenhouse. Within 10 weeks, the plants were self pollinated and/or out-crossed to elite inbreds to produce $R_2$ seed. The $R_2$ seed was analyzed to identify those of interest.

EXAMPLE 9

Gas Chromatography-Fatty Acid Methyl Ester Analysis (GC/Fame) of Maize Tissues

The procedure for extraction and esterification of fatty acids from plant tissue was a modification of Browse et. al.

((1986) Anal. Biochem. 152:141–145). One to 20 mg of plant tissue was placed in a test tube. After addition of 1 mL of methanolic-HCL (Supelco, Bellefonte, Pa.), the tubes were purged with nitrogen gas and sealed. Tubes were then heated at 80° C. for 1 h and allowed to cool. Fatty acid methyl esters were removed from the reaction mixture by extraction with hexane, which involved adding 1 mL of hexane and 1 mL of 0.9% (w/v) NaCl followed by vigorous shaking. After centrifugation at 16,000×g for 5 min the top hexane layer was used for FAME.

Analysis was performed by injection of 1 μL of sample on a Hewlett-Packard (Wilmington, Del.) Series II model 5890 gas chromatograph equipped with a flame ionization detector and a J&W Scientific (Folsom, Calif.) DB-23 column. The oven temperature was maintained at 150° C. throughout the run (20 min) and the flow of the carrier gas (helium) was 80 cm/sec. Conditions allowed separation of the five fatty acid methyl esters of interest having varying carbon lengths: 16:0, palmityl methyl ester; 18:0, stearyl methyl ester; 18:1, oleoyl methyl ester; 18:2, linoleoyl methyl ester; and 18:3, linolenyl methyl ester. Data collection and analysis was performed with a Hewlett-Packard Series II Model 3396 integrator and a PE Nelson (Perkin-Elmer) data collection system. The percentage of each fatty acid methyl ester in the sample was taken directly as indicated by the data collection system. Quantitative amounts of each fatty acid methyl ester were calculated using peak areas of a standard (Matreya, Pleasant Gap, Pa.) having known amounts of the five fatty acid methyl esters of interest. The amount determined was used to estimate the percentage of each fatty acid per total fresh weight. Adjustments were not made for loss of fatty acids during the extraction and esterification procedure since recoveries typically ranged from 90 to 100% depending on the original amount of the sample. The presence of plant tissue in the extraction mixture had no effect on the recovery of known quantities of standard.

EXAMPLE 10

Method for Production of Maize Somatic Embryos and Analysis of Fatty Acids Therein Embryogenic callus material containing the genes of interest was maintained as described herein. Continuous production of somatic embryos, which make up a large portion of embryogenic callus, was performed by transferring the callus tissue every two weeks. While the somatic embryos continued to proliferate, they usually remained in an early stage of embryo development because of the continued presence of 2,4-D in the culture medium. Somatic embryos could be regenerated into plantlets when callus was subjected to the regeneration procedure described herein. During regeneration, somatic embryos formed roots and a shoot, subsequently ceasing development as an embryo.

Somatic embryos were made to develop as seed embryos by growing embryogenic callus on MS medium containing 6% (w/v) sucrose. The callus was grown for 7 days and then somatic embryos were individually transferred to MS medium with 6% sucrose and 10 μM abscisic acid, hereinafter ABA.

Somatic embryos were assayed for fatty acid composition using GC/FAME 3 to 7 days after growth on MS medium containing 6% sucrose and 10 μM ABA. Their fatty acid composition was compared to the fatty acid composition of embryogenic callus and to maize zygotic embryos 12 DAP (Table 5). Fatty acid composition of embryogenic callus differed from that of somatic embryos in that the callus had higher percentages of 16:0 and 18:3 while having lower percentages of 18:1 and 18:2. In addition, the percentage of lipid by fresh weight for the embryogenic callus was low (0.4%) compared to the somatic embryos (4.0%). The fatty acid composition of the zygotic embryos and somatic embryos were very similar and their percentage of lipid by fresh weight were nearly identical. These data validated the use of the somatic embryo culture system as an in vitro system for testing the effect of certain genes on lipid synthesis in developing embryos of maize.

TABLE 5

A comparison of the fatty acid composition of embryogenic callus, somatic embryos and zygotic embryos.

| Fatty Acid Methyl Ester | Percent Fatty Acid Composition | | |
|---|---|---|---|
| | Embryogenic Callus[a] | Somatic Embryo[a,b] | Zygotic Embryo[a,c] |
| 16:0 | 19.4 ± 0.9 | 12.6 ± 0.7 | 14.5 ± 0.4 |
| 18:0 | 1.1 ± 0.1 | 1.6 ± 0.8 | 1.1 ± 0.1 |
| 18:1 | 6.2 ± 2.0 | 18.2 ± 4.9 | 18.5 ± 1.0 |
| 18:2 | 55.7 ± 3.1 | 60.7 ± 5.1 | 60.2 ± 1.5 |
| 18:3 | 8.8 ± 2.0 | 1.9 ± 0.3 | 1.4 ± 0.2 |

[a]The percentage of lipid by fresh weight of tissue was 0.4 ± 0.1, 4.0 ± 1.1, and 3.9 ± 0.6 for embryogenic callus, somatic embryo, and zygotic embryo, respectively.
[b]Somatic embryos were grown on MS medium containing 6% sucrose and 10 mM ABA.
[c]Zygotic embryo were tested 12 DAP.

EXAMPLE 11

Alteration of Fatty Acid Composition in Maize Tissues by Transforming with Plasmids Containing Antisense (pDAB374) and Sense (pDAB376) Maize PTE Under Control of the Ubiquitin Constitutive Promoter Regulatory Element Somatic embryos transformed with pDAB374 were produced from embryogenic callus using the methods described herein. Control somatic embryos were produced from untransformed lines having backgrounds identical to that of the transformed lines. The 16:0 content of the control somatic embryos ranged from ca. 10 to 16%. A reduction in 16:0 was evident in many of the transgenic lines when levels were compared to the specific control for that line. Table 6 shows the total fatty acid composition of somatic embryos produced from lines 374-11 and 374-59, in which the average reduction in 16:0 content compared to control somatic embryos, was 13% and 14% respectively.

Fatty acid analysis was performed on leaf tissue from plants transformed with pDAB374 (Table 7). A significant number of these plants had 16:0 levels in leaf tissue that were lower than the lowest level observed in the control leaves. Three lines, 374-11, 374-14 and 374-59, had significant decreases in 16:0 content. It was determined by Southern analysis using a PTE probe as described herein that all the lines described above having lowered 16:0 content contained at least one intact copy of the gene of interest. The results described herein indicate that the 16:0 levels and saturate levels of transgenic maize somatic embryo tissues and leaf tissues can be altered by introduction of the PTE gene or fragments thereof in the antisense orientation under control of a promoter regulatory element.

TABLE 6

Fatty acid composition of somatic embryos produced from transgenic containing PTE antisense (pDAB374).

| Culture Line | Average Fatty Acid Content (Percent of Total Fatty Acids ± SE) | | | | | Total Fatty Acid Content (% of fresh weight) |
| --- | --- | --- | --- | --- | --- | --- |
|  | 16:0 | 18:0 | 18:1 | 18:2 | 18:3 |  |
| 374-11 | 12.0 | 1.5 | 19.6 | 64.2 | 1.7 | 4.4 |
|  | (± 0.8) | (± 0.5) | (± 2.6) | (± 2.9) | (± 0.4) | (± 0.8) |
| control | 13.8 | 1.7 | 17.4 | 62.9 | 2.7 | 3.0 |
|  | (± 0.5) | (± 0.2) | (± 1.5) | (± 2.1) | (± 0.5) | (± 0.7) |
| 374-59 | 11.9 | 1.6 | 19.4 | 64.6 | 1.3 | 5.2 |
|  | (± 0.6) | (± 1.0) | (± 7.7) | (± 8.9) | (± 0.2) | (± 1.9) |
| control | 14.5 | 0.8 | 15.6 | 67.7 | 1.4 | 4.3 |
|  | (± 0.8) | (± 0.1) | (± 1.4) | (± 1.3) | (± 0.4) | (± 1.0) |

Somatic embryos were produced using the method described herein from embryogenic callus transformed with PTE in the sense orientation (pDAB376). Some of the embryos analyzed had 16:0 contents greater than 2-fold that found in the control (Table 8). Fatty acid analysis of leaf tissues from plants transformed with pDAB376 was also performed. Some of the plant lines had 16:0 levels which were significantly higher than that of the controls. The fatty acid composition of leaves from these plants are illustrated in Table 9. It was determined by Southern analysis using a PTE probe as described herein that all the lines described herein having increased 16:0 content contained at least one intact copy of the gene of interest. The results described herein indicate that the 16:0 levels and saturate levels of transgenic maize somatic embryo tissue and leaf tissue can be altered by introduction of the PTE gene or fragments thereof in the sense orientation under control of a promoter regulatory element.

TABLE 7

Fatty acid composition of leaves from plants regenerated from lines 374-11 and 374-14.

| Culture Line | Average Fatty Acid Content Percent of Total Fatty Acids (± SE) | | | | | Total Fatty Acid content (% fresh weight) |
| --- | --- | --- | --- | --- | --- | --- |
|  | 16:0 | 18:0 | 18:1 | 18:2 | 18:3 |  |
| 374-11 | 13.7 | 1.8 | 1.6 | 14.8 | 61.0 | 0.8 |
|  | (± 2.9) | (± 0.4) | (± 0.5) | (± 3.0) | (± 6.6) | (± 0.2) |
| 374-14 | 13.2 | 2.3 | 1.1 | 13.9 | 63.3 | 0.7 |
|  | (± 0.9) | (± 0.2) | (± 0.5) | (± 1.2) | (± 2.4) | (± 0.1) |
| control | 16.9 | 1.5 | 1.2 | 16.5 | 53.2 | 0.8 |
|  | (± 1.3) | (± 0.3) | (± 0.4) | (± 2.5) | (± 4.9) | (± 0.1) |

TABLE 8

Fatty acid composition of somatic embryos produced from transgenic culture lines transformed with PTE sense (pDAB376)

| Culture Line | Average Fatty Acid Content (Percent of Total Fatty Acids ± SE) | | | | | Total Fatty Acid Content (% fresh weight) |
| --- | --- | --- | --- | --- | --- | --- |
|  | 16:0 | 18:0 | 18:1 | 18:2 | 18:3 |  |
| 376-06 | 23.4 | 5.5 | 28.2 | 39.2 | 2.6 | 3.0 |
|  | (± 5.0) | (± 1.7) | (± 8.6) | (± 5.5) | (± 0.5) | (± 1.0) |
| control | 12.8 | 0.9 | 15.8 | 69.0 | 1.5 | 4.7 |
|  | (± 0.4) | (± 0.1) | (± 1.1) | (± 1.2) | (± 0.2) | (± 0.5) |
| 376-18 | 20.0 | 0.9 | 11.8 | 63.4 | 3.0 | 2.3 |
|  | (± 2.1) | (± 0.2) | (± 1.3) | (± 2.2) | (± 0.5) | (± 0.4) |
| control | 13.3 | 1.3 | 19.1 | 63.5 | 1.3 | 5.1 |
|  | (± 0.5) | (± 0.2) | (± 1.7) | (± 2.1) | (± 0.1) | (± 1.0) |

TABLE 9

Fatty acid cotnposition of leaves from plants regenerated from lines having PTE in the sense orientation (PDAB376)

| Culture Line | Average Fatty Acid Content (Percent of Total Fatty Acids ± SE) | | | | | Total Fatty Acid Content (% of fresh weight) |
| --- | --- | --- | --- | --- | --- | --- |
|  | 16:0 | 18:0 | 18:1 | 18:2 | 18:3 |  |
| 376-38 | 18.7 | 2.3 | 0.7 | 11.7 | 55.6 | 1.1 |
|  | (± 3.7) | (± 0.8) | (± 0.5) | (± 3.1) | (± 6.5) | (± 0.2) |
| 376-40 | 20.2 | 2.8 | 0.9 | 15.3 | 54.8 | 0.8 |
|  | (± 1.2) | (± 0.3) | (± 0.3) | (± 3.4) | (± 4.0) | (± 0.2) |
| control | 16.9 | 1.5 | 1.2 | 16.5 | 53.2 | 0.8 |
|  | (± 1.3) | (± 0.3) | (± 0.4) | (± 2.5) | (± 4.9) | (± 0.1) |

EXAMPLE 12

Alteration of Fatty Acid Composition in Maize Embryos by Transformation with Plasmid pGPN88-1 Containing Maize PTE (Sense) Expressed in a Seed Specific Manner Lines transformed with pGPN88-1 were tested for fatty acid composition using the embryo culture system described herein. Somatic embryos of lines GPN-23 and GPN-103, shown here for example purposes, were found to have decreased 16:0 levels compared to controls (Table 10). The average 16:0 level for the somatic embryos from line GPN-23 was 20% lower than the average of the control culture. The average reduction in 16:0 for line GPN-103 was 24%.

TABLE 10

Fatty acid composition of somatic embryos transformed with PTE (Sense) with the Globulin promoter

| Culture Line | Average Fatty Acid Content (Percent of Total Fatty Acids ± SE) | | | | | Total Fatty Acid Content (% of fresh wt) |
| --- | --- | --- | --- | --- | --- | --- |
|  | 16:0 | 18:0 | 18:1 | 18:2 | 18:3 |  |
| GPN-23 | 9.4 | 1.6 | 20.7 | 66.8 | 1.2 | 5.3 |
|  | (± 0.8) | (± 0.5) | (± 3.8) | (± 4.8) | (± 0.2) | (± 0.8) |

TABLE 10-continued

Fatty acid composition of somatic embryos transformed with PTE (Sense) with the Globulin promoter

| Culture | Average Fatty Acid Content (Percent of Total Fatty Acids ± SE) | | | | | Total Fatty Acid Content |
|---|---|---|---|---|---|---|
| Line | 16:0 | 18:0 | 18:1 | 18:2 | 18:3 | (% of fresh wt) |
| control | 12.0 (± 0.5) | 1.2 (± 0.4) | 17.5 (± 3.1) | 67.1 (± 3.2) | 1.3 (± 0.2) | 6.1 (± 1.2) |
| GPN-103 | 11.0 (± 1.1) | 1.1 (± 0.2) | 17.5 (± 3.7) | 69.2 (± 3.8) | 1.3 (± 0.3) | 4.4 (± 1.5) |
| control | 14.5 (± 0.4) | 0.9 (± 0.1) | 15.6 (± 1.6) | 67.7 (± 1.5) | 1.4 (± 0.2) | 4.3 (± 0.7) |

Embryogenic callus from lines GPN-22, GPN-23, and GPN-24 was used to regenerate plants as described herein. Pollinations were made, seed were obtained as described herein, and fatty acid methyl ester analysis was performed on a small portion (0.5 to 1.5 mg) of each seed embryo. A comparison of the fatty acid composition of seed from two of the three lines is shown in Table 11. All of the lines described above showing reduced 16:0 levels contained at least one intact copy of the gene of interest, as determined by Southern analysis. Those seed showing reduced 16:0 had levels that were ca. 40% lower than that seen for the controls. Seed having lowered levels of 16:0 had concomitant small increases in 18:1 and 18:2 content. The seed with the lowest levels of 16:0 had the following profile: 4.8% of 16:0; 2.0% of 18:0; 18.8% of 18:1; 73.9% of 18:2 and 0.4% of 18:3, with total fatty acid content of 27.4 percent fresh weight. The data described herein demonstrate that a reduction in the levels of saturated fatty acids, particularly palmitate (16:0), in somatic embryos and seeds of maize, can be obtained by transformation with a gene construct composed of a PTE gene in a sense orientation relative to a seed-specific promoter.

An increase in 16:0 levels in somatic embryos of lines was also observed when transformed with pGPN88-1. The average 16:0 content of somatic embryos from lines with increased 16:0 ranged from 15 to 35% above that of the control. The fatty acid composition of somatic embryos of two lines showing increases in 16:0 levels is shown in Table 12.

TABLE 11

The fatty acid composition of seed embryos from GPN-22 and GPN-23.

| Embryos From Plant | Average Fatty Acid Content (as Percent of Total Fatty Acid ± SE) | | | | | Total Fatty Acid Content (% Fresh Wt) |
|---|---|---|---|---|---|---|
| Line: | 16:0 | 18:0 | 18:1 | 18:2 | 18:3 | |
| GPN-22 Reduced 16:0 | 6.5 (± 0.7) | 1.3 (± 0.2) | 17.2 (± 1.4) | 74.2 (± 1.1) | 0.5 (± 0.1) | 31.1 ± 6.5 |
| GPN-23 Reduced 16:0 | 7.3 (± 1.0) | 1.3 (± 0.3) | 17.5 (± 1.3) | 73.3 (± 1.7) | 0.6 (± 0.2) | 24.1 ± 4.5 |
| Control[a] | 11.9 (± 0.8) | 1.4 (± 0.2) | 16.3 (± 1.4) | 69.3 (± 1.2) | 0.7 (± 0.1) | 30.0 ± 4.5 |

[a]Control seed ernbryos were from plants regenerated from cultures transformed with a gene not involved in oil biosynthesis.

TABLE 12

Fatty acid composition of somatic embryos produced from transgenic lines GPN-55 and GPN-124.

| Line | Average Fatty Acid Content (as Percent of Total Fatty Acids ± SE) | | | | | Total Fatty Acid Content (% of fresh wt) |
|---|---|---|---|---|---|---|
| | 16:0 | 18:0 | 18:1 | 18:2 | 18:3 | |
| GPN-55 | 20.7 (± 1.0) | 1.8 (± 0.2) | 14.6 (± 0.9) | 60.9 (± 1.3) | 1.3 (± 0.3) | 5.5 (± 1.3) |
| control | 12.0 (± 0.5) | 1.2 (± 0.4) | 17.5 (± 3.1) | 67.1 (± 3.2) | 1.3 (± 0.2) | 6.1 (± 1.2) |
| GPN-124 | 23.2 (± 2.0) | 1.4 (± 0.2) | 16.4 (± 1.8) | 57.5 (± 2.6) | 1.2 (± 0.2) | 6.2 (± 0.9) |
| control | 12.3 (± 0.3) | 1.3 (± 0.3) | 19.1 (± 2.9) | 65.7 (± 3.1) | 1.4 (± 0.1) | 6.0 (± 1.0) |

BASTA resistant callus from lines having increased 16:0 content in somatic embryos, was used to regenerate plants as described herein. Pollinations were made and seed was obtained from these plants as described herein. Fatty acid methyl ester analysis was performed on a small portion (0.5 to 1.5 mg) of the seed embryos produced by said plants. The fatty acid composition of seed from two of the lines with increased 16:0 content was compared to the fatty acid composition of seeds with normal 16:0 levels (Table 13). The increase in 16:0 was

TABLE 13

The fatty acid composition of seed embryos from GPN-49 and GPN-55 and GPN-63.

| Embryos From Plant | Average Fatty Acid Content (as Percent of Total Fatty Acid ± SE) | | | | | Total Fatty Acid Content (% of Fresh Weight) |
|---|---|---|---|---|---|---|
| Line: | 16:0 | 18:0 | 18:1 | 18:2 | 18:3 | |
| GPN-49 High 16:0 | 18.0 (± 2.5) | 1.9 (± 0.2) | 15.4 (± 1.1) | 63.8 (± 2.7) | 0.6 (± 0.1) | 31.1 ± 6.5 |
| GPN-55 High 16:0 | 18.0 (± 1.1) | 1.7 (± 0.2) | 15.9 (± 1.2) | 63.3 (± 1.9) | 0.6 (± 0.1) | 22.6 ± 3.0 |
| Control[a] | 11.9 (± 0.8) | 1.4 (± 0.2) | 16.3 (± 1.4) | 69.3 (± 1.2) | 0.7 (± 0.1) | 30.0 ± 4.5 |

[a]Control seed embryos were from plants regenerated from cultures transformed with a gene not involved in oil biosynthesis.

accompanied by an increase in 18:0 and a decrease in 18:2. Southern analysis using the PTE gene, was performed as described herein and the lines having increased 16:0 levels as described above contained at least one intact copy of the gene of interest.

The data described herein indicate that transformation of maize with a DNA construct comprised of the PTE gene in a sense orientation under the control of the seed specific globulin promoter, can alter saturate levels therein. Seed with increased saturate levels, palmitate (16:0) and stearate (18:0), can be produced. Furthermore, it is possible to produce transgenic plant lines having decreased saturate and 16:0 levels as well as plant lines having increased saturate and 16:0 levels by transforming different plants with the same construct.

EXAMPLE 13

Biochemical Analysis of R2 Seed Embryos from Plants Transformed with the Plasmid pGPN88-1

As described herein, plants were produced which were transformed with maize PTE gene in the sense orientation relative to the globulin promoter (pGPN88-1). R1 lines having seed embryos demonstrating reductions in 16:0 levels were further analyzed for PTE acyl-ACP hydrolysis activity. Transgenic plants representing selected R1 seeds were grown under standard greenhouse conditions. Each plant was self-pollinated by hand and between 24 to 27 DAP, the husks were peeled back partially in order to remove kernels. The embryos were dissected out of the kernels, and a small section (2 to 3 mg) of the embryo was analyzed for fatty acid composition by the method described herein. The remainder was frozen at −80° C. until further analysis was performed.

PTE activity, assayed as described herein, was performed on extracted proteins from each individual zygotic embryo of R2 seed normalized for protein concentrations (BioRAD Protein assay, Hercules, Calif.).

TABLE 14

Changes in PTE activity in R2 seed embryos of maize lines transformed with plasmid pGPN88-1.

| Plant | Embryos Tested | 16:0 Content[a] | Thioesterase Activity[b] | Percent Control[c] |
|---|---|---|---|---|
| HiII Control | 12 | 11.9 ± 0.8 | 2425 ± 71.4 | 100 |
| GPN-23.02 Low 16:0 | 20 | 8.5 ± 1.2 | 1886 ± 170.5 | 78 |
| GPN88.04/05 High 16:0 | 20 | 16.0 ± 1.7 | 2881 ± 381.8 | 119 |

[a]16:0 content is expressed as percent of total fatty acids.
[b]Thioesterase activity was determined using radio-labeled 16:0-ACP as the substrate, and are expressed as counts per minute (cpm) radio-labeled 16:0, released per minute.
[c]Percent change of thioesterase activity relative to the control.

Analysis was performed using C-14 labeled 16:0-ACP (the preferred substrate for PTE), as described previously, and is shown in Table 14. Natural variations in thioesterase activity were determined using the nontransformed line HiII as a control.

A significant correlation was observed between the average palmitate (16:0) content and PTE thioesterase activity of R2 seed embryos tested. All material analyzed above for GPN23.02 was derived from R1 seed showing reductions in 16:0 content. However most of these lines were still hemizygous for the transgene. Variations were observed when examining 16:0 content in the progeny of R2 seed embryos which can be explained by the expected segregation of the globulin sense PTE transgene in this generation. The data in Table 14 summarizes the results for R2 seed embryos of line GPN23.02 displaying a reduced 16:0 content (characterized as below 11.0%).

Other transformed plant lines demonstrated increases in 16:0 levels, a result of over-expression of the palmitoyl-ACP thioesterase. R2 seed embryos from two plants derived from a single transformed line (GPN-88) were analyzed as described above and are also presented in Table 14. Controls were as described above. The average 16:0 content of R2 seed embryos from lines GPN-88.04/05 was significantly greater than the control seed embryos. The average thioesterase activity was also greater than the control. Again, a good correlation was observed between 16:0 content and thioesterase activity.

The results described above clearly demonstrate that transformation of maize plants with a PTE gene under control of the globulin promoter, can result in heritable changes in the fatty acid composition of seeds. Furthermore a strong correlation is observed between decreases in 16:0 content and PTE thioesterase activity, and increases in 16:0 content and PTE thioesterase activity respectively.

EXAMPLE 14

Demonstration of Reduced PTE mRNA Levels in R2 Seed of Plants Transformed with pGPN88-1

Changes in PTE mRNA levels in R2 seed embryos from lines GPN23.02 transformed with plasmid pGPN88-1 were determined as follows. Seed embryos were harvested and analyzed for fatty acid composition as described herein. For RNA isolation the frozen embryo was pulverized using a Bessman Tissue Pulverizer (SPECTRUM Medical Industries, Houston, Tex.). RNA was extracted from the frozen powder using RNEASY Plant Mini Kits (QIAGEN, Inc) according to the manufacturers instructions. For expression analysis 5 µg RNA per sample was fractionated by electrophoresis in non- denaturing 10 mM $NaPO_4$ pH 6.8, 1.0% agarose gels. The volume of sample containing 5 µg of RNA was lyophilized, resuspended in 8 µL water, and denatured with an equal volume of 2×sample buffer [40 mM $NaHPO_4$ pH6.8, 10 mM EDTA, 6% formaldehyde, 50% formamide] and heated to 68° C. for 15 min. The denatured sample was chilled on ice and 4 µL loading buffer [50% glycerol, 10 mM EDTA, 5 mM $NaPO_4$, pH 6.8, 0.25% bromophenol blue] was added. The samples were loaded on the gel and electrophoresed for 3 h at 60 V in 10 mM phosphate buffer. RNA was transferred from the gel to GENESCREEN PLUS membrane (NEN Research Products) by capillary transfer with sterile water as the transfer medium. Following transfer the RNA was crosslinked to the membrane using a UV STRATALINKER (Stratagene). The RNA blot was prehybridized for 3 h at 42° C. in hybridization buffer [50 mM sodium phosphate pH6.5, 0.8 M NaCl, 1 mM EDTA, 0.2% SDS, 0.05% bovine serum albumin, 0.05% Ficoll Type40, 10% dextran sulfate]. A hybridization probe specific for the PTE coding region was obtained by digestion of plasmid pDAB376 with the enzyme Sfi I, followed by gel purification gel of 1280 bp PTE fragment. Two-hundred nanogram of gel-purified fragment was labeled with 50 µCi [$\alpha$-$^{32}$P] -dCTP (NEN Research Products) using READY-TO-GO labeling beads (Pharmacia) according to the manufacturer and purified over NUCTRAP push columns (Stratagene). The labeled probe was denatured by boiling for 5 min, chilled on ice for 5 min, and added directly to the prehybridized blots. Hybridization was done in SEAL-A-MEAL bags (DAZEY Corp., Industrial Airport, KA), at 42° C. for 16 h. Blots were washed six times for 30 min in large excess (500 mL) of pre-warmed washing solution [20 mM sodium phosphate pH6.5, 50 mM NaCl, 1 mM EDTA, and 0.1% SDS] at 60° C. The blot was exposed to a phosphor storage screen, scanned on a Molecular Dynamics Personal PHOSPHORIMAGER and examined using IMAGEQUANT Software (Molecular Dynamics).

An intact PTE transcript could always be observed in transgenic samples with normal 16:0 content or in HiII controls. Analyses of HiII embryos were included to serve as positive controls in the hybridization. In contrast, transgenic samples with reduced 16:0 content also had reduced intact transcript levels as well as the presence of degraded PTE transcripts. Degraded transcripts were observed as a smear of hybridization signals having a much smaller size range than the intact transcript. In Table 15 the average PTE mRNA levels in R2 seed of transgenic line GPN-23.02 showing reductions in 16:0 content, is compared to thioesterase mRNA levels in transgenic seeds having normal 16:0 content.

Statistical analysis was performed on the two groups of seed to demonstrate that the measured changes in PTE mRNA levels were significant. These data is summarized in Table 16. Variance analysis demonstrates that the control group shows greater variations in the reduction of the PTE mRNA signal, than the 'low 16:0' group. However, the differences between the mean PTE mRNA reductions of the two groups is highly significant, as determine by the t-Test (P=0.0013). These data described herein indicate that decreases in PTE mRNA levels are observed in R2 seeds of line GPN-23.02, which was obtained by transformation with construct pGPN88-1.

TABLE 15

Reduction in PTE mRNA levels and reductions in 16:0 content in maize R2 seed embryos transformed with construct pGPN88-1.

| line | Embryos Tested | 16:0 Content | Thioesterase mRNA Levels[c] | Percent of Control[d] |
| --- | --- | --- | --- | --- |
| GPN-23.02 Low 16:0[a] | 19 | 8.5 ± 1.1 | 12,133 | 44.1 |
| GPN-23.02 Normal 16:0[d] | 7 | 12.3 ± 0.7 | 27,531 | 100 |

[a]The group of transgenic seeds having 16:0 content below 11.0%.
[b]16:0 content is expressed as the average 16:0 content of total fatty acid composition, with standard deviation.
[c]Thioesterase levels were quantified using IMAGEQUANT software, and are expressed as light units in the intact PTE signal adjusted by subtracting the background in each lane.
[d]The control group of transgenic seeds having 16:0 content between 11.0 and 13.1% of total. The percent control was calculated based on the average thioesterase mRNA level of the control group.

TABLE 16

Relationship between 16:0 content and reduction in PTE mRNA levels in R2 transgenic seeds transformed with pGPN88-1.

| Group | Total seed | Range of 16:0% | Variance in change in PTE levels[a] | Mean of change in PTE levels[b] |
| --- | --- | --- | --- | --- |
| Normal 16:0 | 7 | 11.0–13.1 | 1974.69 | +12.51% |
| Low 16:0 | 19 | 7.0–10.9 | 397.13 | −67.32% |

[a]Variance was determined using the F-test Two Sample for Variances.
[b]Application of the t-Test: Two-Sample Assuming Unequal Variances showed that the difference between the means of the two groups is highly significant (P = 0.0013)

EXAMPLE 15

Isolation and Cloning of a cDNA Encoding Maize Oleoyl-Acyl Carrier Protein Thioesterase A cDNA clone encoding maize OTE was obtained from a cDNA library derived from kernels of maize inbred CS608 (Mycogen Seeds, San Diego, Calif.) as described herein. To isolate said clone, a DNA fragment for use as a probe to isolate the full length cDNA was amplified by PCR. A 5' primer with 384-fold degeneracy, entered herein as SEQ ID NO:32, and a 3' primer entered previously as SEQ ID NO:2, were synthesized as described previously herein. PCR reactions were performed as described previously and the 324 bp PCR product was gel purified on a 1% preparative SEAKEM GTG agarose gel (FMC) in TAE. The DNA was then extracted from the gel using QIAEX (Qiagen) according to the manufacturer. The purified PCR product was sequenced as described herein using the primers utilized in the original PCR amplification. The sequence of said PCR amplification product is entered herein as SEQ ID NO:33.

Analysis of the DNA sequence was performed using MACVECTOR v. 4.1.4 (Oxford Molecular, Campbell, Ky.), which gave theoretical translations and alignments to generate the amino acid sequence entered herein as SEQ ID NO:34.

The DNA fragment (SEQ ID NO:33) was used as a probe for screening the maize CS608 embryo cDNA library for full length OTE clones as described herein, except where noted. The labeled probe was prepared using the random primer labeling kit REDIPRIME (Amersham) according to manufacturer. Unincorporated nucleotides were removed using NUCTRAP push columns (Stratagene) as described previously. Plating of the library and screening with the generated probe (SEQ ID NO:33) was performed as described herein.

A positive plaque containing the maize OTE clone was fully characterized and determined to contained an insert of 1287 bp, entered herein as SEQ ID NO:35. Translation in all three reading frames revealed an 1098 bp open reading frame encoding a pre-protein having 366 amino acids, entered herein as SEQ ID NO:36 and SEQ ID NO:37, respectively. The protein was determined to have a transit peptide and the DNA and amino acid sequence of the mature protein were entered herein as SEQ ID NO 38 and SEQ ID NO:39, respectively. The DNA sequence of the transit peptide is entered herein as SEQ ID NO: 49. The N-terminus of OTE purified from maize seed was determined as described from purified maize OTE.

EXAMPLE 16

Purification of Maize Oleoyl-Acyl Carrier Protein Thioesterase from Kernels

Maize OTE was purified from kernels of genotype CQ806 (Mycogen Seeds) that were harvested 20 DAP. Typically, 200 g of maize kernels were harvested and stored at −70° C. until used. These kernels were then homogenized in 400 mL of 100 mM potassium phosphate buffer, pH 7.0, containing 10% glycerol (v/v), 0.01% TRITON X-100, 2 mM DTT, and 40 g of polyvinylpolypyrrolidone. The homogenate was filtered through four layers of cheesecloth followed by centrifugation at 27,500×g for 40 min. To the recovered supernatant, a 50% (w/v) PEG 8000 solution in water was slowly added while stirring continuously to create a final 5% (w/v) PEG solution. The suspension was allowed to stand for 2 h, and then was centrifuged at 27,500×g for 30 min at 4° C. The supernatant was adjusted to a final PEG concentration of 25% (w/v), and after 2 h was centrifuged at 27,500×g for 30 min. The recovered pellet was dissolved in 100 mL of 20 mM potassium phosphate buffer, pH 7.0, 0.4 mM DTT (buffer A). Any insoluble material was removed by centrifugation at 45,440×g for 10 min.

The resolubilized PEG-precipitated material was applied to hydroxyapatite (HA-Ultrogel, Sigma Chemical Co.) which had been previously loaded into a 2.5×20 cm column equilibrated with buffer A. After loading, the column was washed with 300 mL of buffer A and maize OTE activity was eluted with buffer A having 1 M NaCl. Enzymatic activity was followed using $C^{14}$ labeled 18:1-ACP as substrate. Production of substrate and biochemical assays were performed as described herein. Fractions having thioesterase activity were pooled and desalted to 20 mM Tris, pH 7.0, 0.4 mM DTT (buffer B) on PD-10 columns (Pharmacia). The desalted fraction was then applied to a MonoQ HR 10/10 column (Pharmacia) and the enzyme was eluted using a linear gradient of 0–0.5 M NaCl in buffer B over 30 min. at a flow rate of 4 mL/min. Fractions were assayed for activity and active fractions were pooled and desalted on PD-10 columns (Pharmacia) equilibrated with buffer A.

The MonoQ purified fraction which had been desalted was applied at a flow rate of 0.5 mL/min to the ACP-Sepharose column which had been equilibrated with buffer A. The column was washed with 7 mL of buffer A, 7 mL of 0.05% TRITON X-100 in buffer A, followed by 7 mL of 0.2 M NaCl in buffer A. The enzyme was then eluted with 1 M NaCl in buffer A.

The ACP-Sepharose purified fraction was desalted on a PD-10 column (Pharmacia) which had been previously equilibrated in 25 $\mu$M bis-Tris buffer, pH 7.1 (buffer C). The enzyme was then applied onto a MonoP HR5/20 chromatofocusing column (Pharmacia) that had been equilibrated with buffer C followed by washing with 20 mL to remove unbound protein. Elution was achieved with 10% polybuffer 74-iminodiacetic acid, pH 4.0 (Pharmacia), containing 0.4 mM DTT at a flow rate of 1 mL/min. Biochemical and SDS-PAGE analysis of the eluted protein fraction indicated that all maize OTE activity corresponded to a single band of 38 kDa.

The purified maize OTE protein was electrophoresed on a 10% SDS-PAGE gel (Integrated Separation Systems) and blotted to PROBLOTT membrane (Applied Biosystems) using a LKB 2117 MULTIPHOR II (Pharmacia) according to the manufacturers instructions. The protein band was identified by staining with a 0.1% amido black solution (Sigma Chemical Co) for 1 min followed by destaining in $H_2O$ for 5 min. Protein sequencing was performed by Harvard Microchemistry Facility or Cambridge Prochem (Cambridge, Mass.) and the derived amino-terminal sequence entered herein as SEQ ID NO:40. These data, in conjunction with those obtained from the cDNA clone, indicated that the maize OTE has a 34 amino acid transit peptide.

The substrate specificity of purified maize OTE was analyzed using several $C^{14}$-labeled acyl-ACPs as described herein. It was observed that OTE had a strong preference to the substrate 18:1-ACP. Low activities (less than 10% of that observed with 18:1-ACP) were observed when using 12:0-ACP, 14:0-ACP, 16:0-ACP, 18:0-ACP. The Km values of maize OTE to 18:1-ACP and 16:0-ACP were determined to be 0.75 $\mu$M and 25 $\mu$M, respectively, as determined using double reciprocal plots.

EXAMPLE 17

Expression, Purification and Analysis of E. coli Produced Maize Oleoyl-Acyl Carrier Protein Thioesterase An expression vector was constructed to express mature maize OTE protein upon induction in E. coli. The expression plasmid pDAB371 was constructed by the insertion of the DNA sequence encoding the mature maize OTE peptide (SEQ ID NO:38) into the NcoI and SacI sites of the vector pET-9d (Novagen). A 5' primer and 3' primer, entered herein as SEQ ID NO:41 and SEQ ID NO:42, respectively, were designed such that a 5' NcoI and a 3' Sac I site were added to SEQ ID NO:38 by PCR amplification. PCR reaction conditions and cycling were as those described previously. The resulting reactions were purified over a Centricon 100 column (Amicon) to remove unincorporated nucleotides and primers, and then digested with Nco I and Sac I (New England Biolabs). The digested fragment was further purified on an 1% agarose gel followed by DNA extracted using QIAEX (Qiagen). The E. coli expression vector pET-9d had been modified previously by conversion of a BamHI cloning site to Sac I by the ligation of a BamHI to SacI adapter. The modified pET-9d plasmid DNA was digested with Nco I and Sac I, purified on a 0.8% agarose gel, and extracted using QIAEX (Qiagen). Ligations were performed as described herein using 100 ng each of vector and insert in a 10 $\mu$L ligation reaction. Competent E. coli DH5$\alpha$ cells (GIBCO-BRL) were transformed with the ligation mix, plated on LB agar containing 30 $\mu$g/mL kanamycin, and incubated overnight at 37° C. DNA was extracted from selected isolates and analyzed for the presence of the desired insert. The modified pET-9d vector with the DNA insert having the sequence entered herein as SEQ ID NO:43 (and the corresponding amino acid sequence entered herein as SEQ ID NO:44), was designated pDAB371.

For expression, competent BL21/DE3 (Novagen) cells were transformed with pDAB371, plated on LB agar containing 30 $\mu$g/mL kanamycin and grown overnight at 37° C. Afterwards, these cells were scraped off the plates and used to inoculate 25 mL LB containing 30 $\mu$g/mL kanamycin and 3 mM IPTG (used for induction). Induced cultures were grown at 37° C. with shaking for 2.5 hours. Cells were spun down and frozen on dry ice. Proteins extracts were prepared as described herein with the following exceptions: lysozyme was added to the lysis buffer to a final concentration of 1 mg/mL and the two freeze-thaw cycles described previously were omitted.

Crude protein extracts from E. coli cells harboring the expression vector pDAB371 were tested for thioesterase activity using 12:0-ACP, 14:0-ACP, 16:0-ACP, 18:0-ACP, and 18:1-ACP substrates as described previously. Cells harboring the pET-9d plasmid were used as a negative control. Biochemical analysis revealed that the cell extracts from E. coli which had been transformed with pDAB371 had high levels of 18:1 thioesterase activity compared to the negative control as shown in Table 17.

TABLE 17

| Substrate specificity of partially purified maize OTE expressed in E. coli. | |
|---|---|
| Enzyme Substrate | Percent Relative Activity* |
| 12:0-ACP (Laurate) | 0.7 |
| 14:0-ACP (Myristate) | 6.3 |
| 16:0-ACP (Palmitate) | 14.1 |
| 18:0-ACP (Stearate) | 25.2 |
| 18:1-ACP (Oleate) | 100.0 |

ª100% relative activity is equivalent to a specific activity of 2.1 units/mg protein where a unit is defined as the cleavage of 1 $\mu$mol/h free fatty acid at 3° C.

EXAMPLE 18

Construction of Antisense Maize Oleoyl-Acyl Carrier Protein Thioesterase Plant Transformation Constructs A plasmid (pDAB382) containing the full length maize OTE cDNA (SEQ ID NO:47) in an antisense orientation relative to the maize ubiquitin promoter was constructed for transformation of maize plants. The cDNA previously identified as SEQ ID NO:36 was PCR amplified with primers to incorporate unique Sfi I sites into the 5' and 3' ends of the gene to facilitate subsequent cloning into vector pDAB439, as decribed herein. Primer sequences for the 5' and 3' ends are entered herein as SEQ ID NO:45 and SEQ ID NO:46, respectively. This DNA was recalcitrant to PCR amplification due to its high melting temperature. Therefore, template DNA was denatured using the following conditions: 10 μg DNA was added to 4 μL of denaturing solution [2M NaOH, 2 mM EDTA] in a volume of 20 μL. After 5 minutes on ice, the mixture was neutralized and precipitated simultaneously at −20° C. for 30 min by the addition of 88 μL of buffer [8 mL of 1 M Tris, pH 8.0, 3 mL of 3M sodium acetate pH 5.3, and 75 mL 100% ethanol]. The DNA was pelleted for 30 min at 16,000×g, followed by washing with 70% ethanol. In addition, possible secondary structure interfering with amplification was diminished by using 7-deaza-dGTP in the nucleotide mixture at a ratio of 3:1 (150 mM 7-deaza dGTP/50 mM dGTP). The amplification reaction included the following components: 100 ng of denatured cDNA (SEQ ID NO:36), 10 μL of 10×RB, 10 μL 2 mM dNTP mix containing 7-deaza dGTP, 200 pmoles each of primer (SEQ ID NO:45 and SEQ ID NO:6), 5 units AMPLITAQ polymerase (Perkin-Elmer) in a final volume of 100 μL. The reactions were performed as previously described. The PCR product of 1140 base pairs having the sequence entered herein as SEQ ID NO:47 was digested with Sfi I, gel purified and cloned into the Sfi I sites of pDAB439 as described herein. This plasmid was designated pDAB382.

EXAMPLE 19

Alterations of Fatty Acid Compostion in Maize Tissues as a Result of Transformation with the Plasmid Containing Antisense (pDAB382) Maize OTE The plasmid pDAB382 was blasted into Type II callus as described previously. Following Southern and GC/FAME analyses as described herein, callus was transferred to regeneration media and transgenic plants were regenerated as described herein. R0 plants from the regenerations were self- or sib-pollinated, to produce R1 seed.

The R1 seed obtained from the crosses made above were analyzed for fatty acid composition using GC-FAME as described herein. Sublines were selected to be further propagated based on the progeny (R1 seed) from these sublines having elevated 16:0 levels. The seed was planted in five gallon pots and were self-pollinated ca. 10 weeks later to produce $R_2$ seed. This seed was then analyzed to determine saturate levels as described below.

Somatic embryos from lines transformed with pDAB382 were assayed for fatty acid composition as described herein. Lines transformed with pDAB382 had increased 16:0 levels when compared to the nontransformed controls. The total fatty acid composition of somatic embryos of two of these lines is shown in Table 18. Southern analysis revealed that those lines showing increased 16:0 content contained at least one copy of the gene of interest.

TABLE 18

Fatty acid composition of somatic embryos produced from transgenic culture lines 382-13 and 382-29.

| Culture | Average Fatty Acid Content (as Percent of Total Fatty Acids ± SE) | | | | | Total Fatty Acid Content |
|---|---|---|---|---|---|---|
| Line | 16:0 | 18:0 | 18:1 | 18:2 | 18:3 | (% of fresh wt) |
| 382-13 | 16.1 | 0.8 | 14.3 | 66.4 | 1.8 | 4.8 |
|  | (± 0.4) | (± 0.1) | (± 1.2) | (± 1.3) | (± 0.2) | (± 0.7) |
| control | 13.3 | 1.3 | 19.1 | 63.5 | 1.3 | 5.1 |
|  | (± 0.5) | (± 0.2) | (± 1.7) | (± 2.1) | (± 0.1) | (± 1.0) |

TABLE 18-continued

Fatty acid composition of somatic embryos produced from transgenic culture lines 382-13 and 382-29.

| Culture | Average Fatty Acid Content (as Percent of Total Fatty Acids ± SE) | | | | | Total Fatty Acid Content |
|---|---|---|---|---|---|---|
| Line | 16:0 | 18:0 | 18:1 | 18:2 | 18:3 | (% of fresh wt) |
| 382-29 | 14.4 | 1.1 | 16.8 | 65.7 | 1.5 | 4.4 |
|  | (± 1.0) | (± 0.2) | (± 1.5) | (± 2.3) | (± 0.3) | (± 0.8) |
| control | 12.5 | 1.3 | 18.2 | 65.8 | 1.5 | 4.9 |
|  | (± 0.6) | (± 0.4) | (± 4.3) | (± 4.3) | (± 0.2) | (± 0.6) |

BASTA resistant lines transformed with pDAB382 were regenerated to plants as described previously and GC/FAME was performed on their leaf tissue. As shown in Table 19, leaves of plants transformed with pDAB382 had increased 16:0 levels when compared to control plants which were transformed with a gene not related to fatty acid synthesis. Southern analysis revealed that those lines showing increased 16:0 content contained at least one copy of the gene of interest.

TABLE 19

Fatty acid composition of leaves from plants regenerated from lines 382-13 and 382-44.

| Line | Average Leaf Fatty Acid Content (as Percent of Total Fatty Acids ± SE) | | | | | Total Fatty Acid Content |
|---|---|---|---|---|---|---|
|  | 16:0 | 18:0 | 18:1 | 18:2 | 18:3 | (% of fresh wt) |
| 382-13 | 23.4 | 2.1 | 2.0 | 13.7 | 48.1 | 0.7 |
|  | (± 1.6) | (± 0.4) | (± 0.9) | (± 2.2) | (± 3.5) | (± 0.1) |
| 382-44 | 21.3 | 2.0 | 2.6 | 17.0 | 45.4 | 0.6 |
|  | (± 1.4) | (± 0.2) | (± 0.7) | (± 1.8) | (± 4.7) | (± 0.1) |
| control | 16.9 | 1.5 | 1.2 | 16.5 | 53.2 | 0.8 |
|  | (± 1.3) | (± 0.3) | (± 0.4) | (± 2.5) | (± 4.9) | (± 0.1) |

R0 plants regenerated from embryogenic lines transformed with pDAB382 were pollinated and fatty acid analysis was performed on the mature R1 seed embryos. The fatty acid composition of seed embryos from two lines is shown in Table 20. Southern analysis revealed that those lines showing increased 16:0 content contained at least one copy of the gene of interest.

The data described above indicate that maize plants with altered fatty acid composition can be obtained by transformation with a OTE gene construct, having the gene in the antisense orientation relative to the promoter. The changes measured above indicate that increases in the level of the saturated fatty acid palmitate (16:0) are obtained, concomitant with a decrease in unsaturated fatty acids. This observation is consistent with the fact that the OTE enzyme has substrate preference for 18:1-ACP.

TABLE 20

Fatty acid composition of seed embryos from seed produced from crosses of 382-13 and 382-44. The average fatty acid content of seed embryos with increased[a] 16:0 compared to those with normal[b] 16:0 content.

| Plant Line | Average Fatty Acid Content (as Percent of Total Fatty Acids ± SE) | | | | | Total Fatty Acid Content |
|---|---|---|---|---|---|---|
| | 16:0 | 18:0 | 18:1 | 18:2 | 18:3 | (% fresh wt) |
| Increased 16:0[a] | 17.4 (± 1.3) | 0.7 (± 0.2) | 11.8 (± 2.3) | 68.9 (± 2.9) | 0.9 (± 0.3) | 16.0 (± 4.4) |
| Increased 16:0[a] | 14.8 (± 0.7) | 1.5 (± 0.4) | 21.8 (± 3.5) | 60.8 (± 3.9) | 0.7 (± 0.1) | 29.3 (± 5.8) |
| Control[c] | 11.9 (± 0.8) | 1.4 (± 0.2) | 16.3 (± 1.4) | 69.3 (± 1.2) | 0.7 (± 0.1) | 30.0 (± 4.5) |

[a]Increased 16:0 levels were all 16:0 percentages higher than 14%.
[b]Control seed embryos were from plants regenerated from cultures transformed with a gene that was not related to this study.

EXAMPLE 20

Biochemical Analysis of Embryos from Plants Transformed with the Plasmid pDAB382

As described previously, plants were produced which were transformed with the maize OTE gene in the antisense orientation relative to the ubiquitin promoter (pDAB382). Individual zygotic embryos were dissected from R2 seed 20 to 22 days after pollination and analyzed for fatty acid composition as described herein. For OTE analysis, protein was extracted from each individual zygotic embryo of R2 seed normalized for protein concentrations (BioRAD), and analyzed using $C^{14}$ labeled 18:1-ACP. The natural variation of thioesterase activity was determined for a nontransformed line HiII. In addition, transformed lines which did not contain the gene of interest were also used as controls.

For Western analysis total proteins were separated on SDS-PAGE as described (Laemmli, (1970), Nature, 227:680–685). Proteins were electrophoretically transferred to ECL nitrocellulose membranes (Amersham) using a Pharmacia Semi-Dry Blotter with buffer (Towbin et al., (1979), Proc. Natl. Acad. Sci. USA, 76:4350–4354). The nonspecific binding sites were blocked with 5% (w/v) dry milk in phosphate buffer saline for 1 h. Immunoreactive polypeptides were detected using the ECL Western Blotting Detection Reagent (Amersham) with rabbit antiserum raised against a synthetic peptide, entered herein as SEQ ID NO:48, which was specific to amino acids 304–323 of the protein sequence previously entered herein as SEQ ID NO:37. The domain-specific antibodies were produced by (Genemed Biotechnologies Inc., San Francisco, Calif.). The secondary antibody was goat anti-rabbit serum conjugated to horseradish peroxidase (BioRAD). Autoradiograms were scanned with a Molecular Dynamics Scanner as described previously and quantified using IMAGEQUANT software (Molecular Dynamics). The results are shown in Table 21.

TABLE 21

Decreased OTE activity and OTE protein levels in R2 seed embryos of maize plants transformed with plasmid pDAB382.

| Plant code | GOI[a] | 16:0 Content[b] | Enzyme Activity[c] | Protein Level[d] |
|---|---|---|---|---|
| HiII control | – | 13.4 ± 0.8 | 4472 ± 127.0 | 100 |
| 382-13 control | – | 13.9 ± 0.6 | 4506 ± 246.2 | 98 |
| 382-13 With GOI | + | 17.4 ± 2.1 | 2665 ± 1041 | 61 |

[a]GOI = gene of interest, referring to whether or not the antisense OTE gene is present or absent based on Southern Analysis of the R1 plants which produced the seeds analyzed in this study;
[b]16:0 content is percentage of total fatty acids.
[c]Thioesterase activity were determined using radio-labeled 18:1-ACP as the substrate. Numbers listed are counts per minute of radiolabeled 18:1 released per minute; and
[d]OTE protein levels determined as a percentage relative to controls by Western Analysis.

As shown in Table 21, the average 16:0 content of R2 seed embryos of plants containing the gene of interest was significantly greater than that of the control embryos. The average 16:0 content of R2 seed embryos of the plants not containing the gene of interest was similar to that of the control. An average 46.6% reduction in OTE enzyme activity was observed in seeds of plants containing the gene of interest, with enzyme activity reduction ranging from 22.0% to 70.1%. No reduction in OTE levels were observed in R2 seeds of plants not containing the gene of interest.

The results presented above indicate that transformation of maize plants with a gene construct comprised of the OTE gene in the antisense orientation will cause modification of seed OTE enzyme levels and enzyme activity. Furthermore a strong correlation exists between enzyme levels, enzyme activity levels and 16:0 content.

EXAMPLE 21

Demonstration of Reduced OTE mRNA Levels in R2 Seed Embryos of Plants Transformed with pDAB382

Changes in OTE mRNA levels in R2 seed embryos of plants derived from transformation with plasmid pDAB382 was determined as follows. Transgenic plants were grown under standard greenhouse conditions. Embryos were harvested and analyzed for fatty acid composition, and RNA was extracted for analysis as described herein. However, for OTE expression analysis only 1.5 μg RNA per sample was fractionated by electrophoresis. RNA electrophoresis, blotting and hybridization, probe labeling, washing of the blots, and exposure and quantitation of mRNA signals, were done as described herein. The hybridization probe specific for the OTE coding region was obtained by digestion of plasmid pDAB382 with the enzyme Sfi I, followed by purification through agarose gel of the 1124 bp OTE fragment.

A summary of the quantified OTE mRNA levels in transgenic R2 seed embryos is shown in Table 22. R2 seed from three transgenic lines derived from 382-13, showing an increase 16:0 content is compared to R2 seed from the same line having 16:0 content in the normal range.

TABLE 22

Changes in 16:0 content and OTE mRNA levels in R2 seed embryos of maize lines transformed with plasmid pDAB382.

| Line[a] | Embryos Tested | 16:0 Content[b] | Thioesterase mRNA Levels[c] | Percent of Control[d] |
|---|---|---|---|---|
| 382-13 Normal 16:0 | 11 | 13.5 ± 0.8 | 21230 ± 10367 | 94 ± 46 |
| 382-13 High 16:0 | 15 | 17.2 ± 0.8 | 3489 ± 1916 | 15 ± 8 |

[a]Transgenic seed with higher than normal 16:0 content was compared to control transgenic seed with normal 16:0 content.
[b]Indicates the average 16:0 content for each group, expressed as a percentage of total fatty acids, with standard deviation.
[c]Indicates the OTE signal measured in light units, after subtraction of background.
[d]OTE signals were expressed as percentage of OTE mRNA levels in control seeds of line 382-13.03.02, which are transformed but due to segregation no longer carry the gene of interest.

Statistical analysis was performed to demonstrate that the reduction of OTE mRNA levels in the high 16:0 group was significantly different from the change in OTE mRNA level in the control group, having normal 16:0 content. The results are summarized in Table 23. Variance analysis indicates that the variability in changes in OTE mRNA levels in the control group is much higher than the 'high 16:0' grouping. However, despite the high variability in the control group, the difference between the mean reduction in OTE mRNA levels in the high group, compared to that of the control group, is highly significant (P=0.000139).

The data presented herein indicate that increased 16:0 content in tissues of plants transformed with pDAB382 correlated with reductions in OTE enzyme activity, protein levels, and mRNA levels. Furthermore, the data described herein demonstrates that an alteration in fatty acid composition can be obtained in seeds derived from plants transformed with a gene construct consisting of the OTE gene in the antisense orientation relative to the promoter.

TABLE 23

Relationship between 16:0 content and reduction in OTE mRNA levels in R2 transgenic seeds carrying the gene of interest.

| Group | Number of seeds | Range of 16:0% | Variance in change in OTE levels[a] | Mean of change in OTE levels[b] |
|---|---|---|---|---|
| Normal 16:0 | 7 | 12.3–13.7 | 963.619 | +3.57% |
| High 16:0 | 15 | 14.4–18.7 | 33.124 | −85.86% |

[a]Variance was determined using the F-test Two Sample for Variances.
[b]Appiication of the t-Test: Two-Sample Assuming Unequal Variances showed that the difference between the means of the two groups is highly significant (P = 0.000139).

What is claimed is:

1. An isolated DNA molecule comprising a nucleic acid selected from the group consisting of SEQ ID NO:3, SEQ ID NO:5, SEQ ID NO:6, SEQ ID NO:8, SEQ ID NO:12, SEQ ID NO:16, SEQ ID NO:19, SEQ ID NO:22, SEQ ID NO:23, SEQ ID NO:27, SEQ ID NO:28, SEQ ID NO:29, SEQ ID NO:31, SEQ ID NO:33, SEQ ID NO:35, SEQ ID NO:36, SEQ ID NO:38, SEQ ID NO:43, SEQ ID NO:47, and SEQ ID NO:49.

2. An isolated DNA sequence encoding an amino acid sequence selected from the group consisting of SEQ ID NO:4, SEQ ID NO:7, SEQ ID NO:9, SEQ ID NO:13, SEQ ID NO:34, SEQ ID NO:37, SEQ ID NO:39, SEQ ID NO:44 and SEQ ID NO:48.

3. A chimeric DNA construct comprising operably linked in the 5' to 3' direction: a promoter regulatory element; an acyl-ACP thioesterase nucleic acid isolated from maize selected from the group consisting of SEQ ID NO:3, SEQ ID NO:5, SEQ ID NO:6, SEQ ID NO:8, SEQ ID NO:12, SEQ ID NO:16, SEQ ID NO:19, SEQ ID NO:27, SEQ ID NO:28, SEQ ID NO:29, SEQ ID NO:33, SEQ ID NO:35, SEQ ID NO:36, SEQ ID NO:38, SEQ ID NO:43, and SEQ ID NO:47; and a transcriptional terminator sequence.

4. The DNA construct of claim 3 wherein the promoter regulatory element is selected from the group consisting of SEQ ID NO:22, SEQ ID NO:23, and SEQ ID NO:31.

5. The DNA construct of claim 3 wherein said acyl-ACP thioesterase nucleic acid isolated from maize is in the antisense orientation and is selected from the group consisting of SEQ ID NO:16 and SEQ ID NO:47.

6. A plant cell comprising the DNA construct of claim 3.

7. The plant cell of claim 6 wherein said acyl-ACP thioesterase nucleic acid isolated from maize is in the antisense orientation and is selected from the group consisting of SEQ ID NO:16 and SEQ ID NO:47.

8. The plant cell of claim 6 wherein said cell is selected from the group consisting of soybean, Brassicaceae sp., canola, rape, sunflower, flax, safflower, coconut, palm, olive, peanut, cotton, castor bean, coriander, Crambe sp., Cuphea sp., Euphorbia sp., Oenothera sp., jojoba, Lesquerella sp., marigold, Limnanthes sp., Vernonia sp., *Sinapis alba*, cocoa, and maize.

9. The plant cell of claim 8 wherein said cell is a seed embryo cell.

10. A transgenic plant regenerated from the plant cell of claim 8 or progeny of said transgenic plant wherein said progeny comprise the DNA construct of claim 1.

11. A method of producing a plant oil having an altered level of palmitic acid comprising: growing a plant cell having integrated into its genome the DNA construct according to claim 3 wherein said acyl-ACP thioesterase nucleic acid isolated from maize is selected from the group consisting of SEQ ID NO:5, SEQ ID NO:6, SEQ ID NO:8, SEQ ID NO:12, SEQ ID NO:16, SEQ ID NO:19, SEQ ID NO:27, SEQ ID NO:29, SEQ ID NO:35, SEQ ID NO:36, SEQ ID NO:38, SEQ ID NO:43, and SEQ ID NO:47, and isolating the oil from said plant cell.

12. The method of claim 11 wherein said plant cell is selected from the group consisting of soybean, Brassicaceae sp., canola, rape, sunflower, flax, safflower, coconut, palm, olive, peanut, cotton, castor bean, coriander, Crambe sp., Cuphea sp., Euphorbia sp., Oenothera sp., jojoba, Lesquerella sp., marigold, Limnanthes sp., Vernonia sp., *Sinapis alba*, cocoa, and maize.

13. A method of producing plant oil having altered levels of palmitic acid comprising growing a plant cell having integrated into its genome the DNA construct of claim 3 wherein said acyl-ACP thioesterase nucleic acid isolated from maize is selected from the group consisting of SEQ ID NO:5, SEQ ID NO:6, SEQ ID NO:8, SEQ ID NO:12, SEQ ID NO:16, SEQ ID NO:19, SEQ ID NO:27, SEQ ID NO:29, SEQ ID NO:35, SEQ ID NO:36, SEQ ID NO:38, SEQ ID NO:43, and SEQ ID NO:47, regenerating a transgenic plant from said plant cell, and isolating the oil from said transgenic plant.

14. A method of producing plant oil having altered levels of palmitic acid comprising growing a plant cell having integrated into its genome the DNA construct of claim 3 wherein said acyl-ACP thioesterase nucleic acid isolated from maize is selected from the group consisting of SEQ ID NO:5, SEQ ID NO:6, SEQ ID NO:8, SEQ ID NO:12, SEQ ID NO:16, SEQ ID NO:19, SEQ ID NO:27, SEQ ID NO:29, SEQ ID NO:35, SEQ ID NO:36, SEQ ID NO:38, SEQ ID NO:43, and SEQ ID NO:47, regenerating a transgenic plant from said plant cell, obtaining progeny of said transgenic plant wherein said progeny comprise the DNA construct of claim 3, and isolating the oil from said progeny.

15. The method of claim 11 wherein said acyl-ACP thioesterase nucleic acid isolated from maize is in the antisense orientation and is selected from the group consisting of SEQ ID NO:16 and SEQ ID NO:47.

16. A composition comprising an amino acid sequence selected from the group consisting of SEQ ID NO:4, SEQ ID NO:7, SEQ ID NO:9, SEQ ID NO:13, SEQ ID NO:34, SEQ ID NO:37, SEQ ID NO:39, SEQ ID NO:44 and SEQ ID NO:48.

* * * * *